(12) United States Patent
Carmeli et al.

(10) Patent No.: US 7,524,929 B2
(45) Date of Patent: Apr. 28, 2009

(54) OPTOELECTRONIC DEVICE AND METHOD OF FABRICATING THE SAME

(75) Inventors: Chanoch Carmeli, Tel-Aviv (IL); Itai Carmeli, Tel-Aviv (IL); Shachar Richter, Mazkeret Batia (IL); Ludmila Frolov, Rishon-LeZion (IL)

(73) Assignee: Ramot At Tel Aviv University Ltd., Tel-Aviv (IL)

( * ) Notice: Subject to any disclaimer, the term of this patent is extended or adjusted under 35 U.S.C. 154(b) by 0 days.

(21) Appl. No.: 11/507,628

(22) Filed: Aug. 22, 2006

(65) Prior Publication Data

US 2008/0305471 A1    Dec. 11, 2008

Related U.S. Application Data

(63) Continuation-in-part of application No. PCT/IL2006/000241, filed on Feb. 22, 2006.

(51) Int. Cl.
*C07K 14/00* (2006.01)
*C12M 1/00* (2006.01)
(52) U.S. Cl. .................................. 530/350; 435/292.1
(58) Field of Classification Search ................ 530/350; 435/292.1
See application file for complete search history.

(56) References Cited

U.S. PATENT DOCUMENTS

| | | | |
|---|---|---|---|
| 6,231,983 | B1 | 5/2001 | Lee et al. |
| 6,558,448 | B2 * | 5/2003 | Hu .............................. 75/252 |
| 2003/0100127 | A1 * | 5/2003 | Corn et al. ................... 436/518 |
| 2003/0141498 | A1 | 7/2003 | Stasiak |
| 2005/0098726 | A1 | 5/2005 | Peumans et al. |

FOREIGN PATENT DOCUMENTS

| | | |
|---|---|---|
| JP | 04-009400 | 1/1992 |
| WO | WO 96/18645 | 6/1996 |
| WO | WO 2004/013915 | 2/2004 |
| WO | WO 2006/060017 | 6/2006 |
| WO | WO 2006/090381 | 8/2006 |
| WO | WO 2008/018982 | 2/2008 |
| WO | WO 2008/023372 | 2/2008 |
| WO | WO 2008/023373 | 2/2008 |

OTHER PUBLICATIONS

Sun et al, Topography of the photosystem I core proteins of the Cyanobacterium Synechocystis sp. PCC 6803, 1997, J biol Chem, vol. 272, p. 27193-802.*
Sun et al, Oxidizing side of the cyanobacterial Photosystem I: Mutational analysis of the luminal H loop of the PsaB subunit, 1999, Photosynthesis Research, vol. 62, p. 241-250.*
Navarro et al, Negatively charged residues in the H loop of PsaB subunit in Photosystem I from Synechocystis sp. PCC 6803 appear to be responsible for electrostatic repulsions with plastocyanin2000, Photosynthesis Research, vol. 65, p. 63-8.*
Sun et al. "Oxidizing Side of the Cyanobacterial Photosystem I", The Journal of Biological Chemistry, 274(27): 19048-19054, 1999.
Lee et al. "Platinization: A Novel Technique to Anchor Photosystem I Reaction Centres Onto a Metal Surface at Biological Temperature and pH", Biosensors & Bioelectronics, 11(4): 375-387, 1996.
Zeng et al. "Stabilization of Iron-Sulfur Cluster Fx by Intra-Subunit Interactions Unraveled by Suppressor and Second Site-Directed Mutations in PsaB of Photosystem I", Biochimica et Biophysica Acta, 1556(2-3): 254-264, 2002.
Das et al. "Integration of Photosynthetic Protein Molecular Complexes in Solid-State Electronic Devices", Nano Letters, 4(6): 1079-1083, 2004.
Trammell et al. "Oriented Binding of Photosynthetic Reaction Centers on Gold Using Ni-NTA Self-Assembled Monolayers", Biosensors and Bioelectronics, 19(12): 1649-1655, 2004.
Nakamura et al. "Self-Assembling Photosynthetic Reaction Centers on Electrodes for Current Generation", Applied Biochemistry and Biotechnology, 84-86: 401-408, 2000.
Frolov et al. "Fabrication of A Photoelectronic Device by Direct Chemical Binding of the Photosynthetic Reaction Center Protein to Metal Surfaces", Advanced Materials, 17(2): 2434-2437, 2005.
Radziemska "Thermal Performance of Si and GaAs Based Solar Cells and Modules: A Review", Progress in Energy and Combustion Science, 29: 407-424, 2003. Abstract.
Millsaps et al. "Nanoscale Photosynthesis: Photocatalytic Production of Hydrogen by Platinized Photosystems I Reaction Centers", Photochemistry and Photobiology, 73(6): 630-635, 2001.
Meshulam et al. "Construction of Dithiol-Based Nanotstructures by A Layer-Exchange Process", Small, XP002474763, 1(8-9): 848-851, Aug. 2005. p. 850, col. 2, Lines 5-22, Fig. 4.
Sarikaya et al. "Molecular Biomimetics: Nanotechnology Through Biology", Nature Materials, XP002478257, 2(9): 28-36, Feb. 2005, p. 578, col. 3-p. 580, col. 2.
Yue et al. "Understanding Interfacial Electron Transfer to Monolayer Protein Assemblies", Current Opinion in Solid State and Materials Science, XP005482034, 9(1-2): 28-36, Feb. 2005. p. 2, 3.
Haick et al. "Effect of Molecular Binding to A Semiconductor on Metal/Molecule/Semiconductor Junction Behavior", Journal of Physical Chemistry B, ACS, XP002474764, 109(19): 9622-9630, May 19, 2005. p. 9622, col. 1, Lines 20-22, p. 9623, col. 1, Lines 24-26, 31-34, 50-53.
Whaley et al. "Selection of Peptides With Semiconductor Binding Specificity for Directed Nanocrystal Assembly", Nature, XP002342143, 405: 665-668, Jun. 8, 2000. p. 665, col. 1, Lines 1-24, col. 2, Lines 5-6, p. 667, col. 2, Lines 51-53.

* cited by examiner

*Primary Examiner*—Mark Navarro

(57) ABSTRACT

A modified isolated polypeptide comprising an amino acid sequence encoding a photocatalytic unit of a photosynthetic organism being capable of covalent attachment to a solid surface and having a photocatalytic activity when attached thereto is disclosed.

4 Claims, 18 Drawing Sheets
(10 of 18 Drawing Sheet(s) Filed in Color)

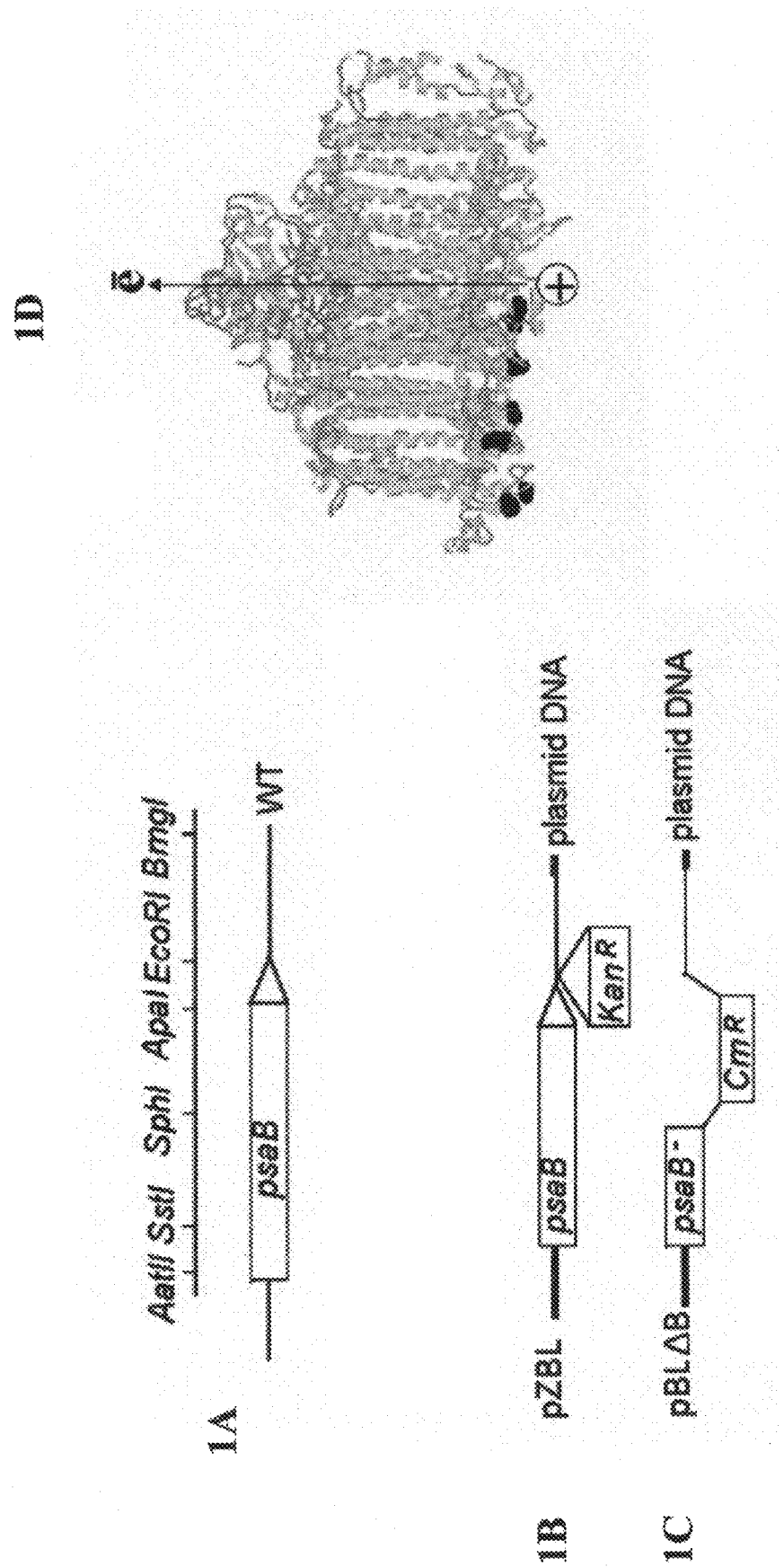
FIGs. 1A-D

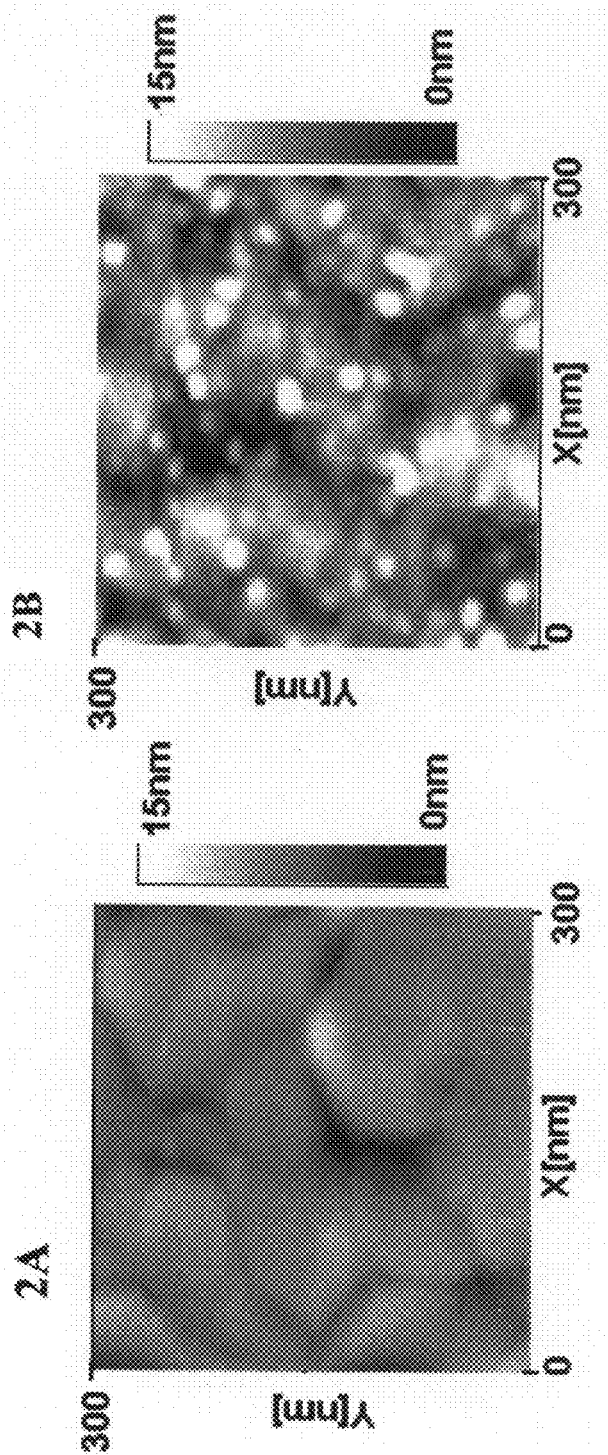
FIGs. 2A-B

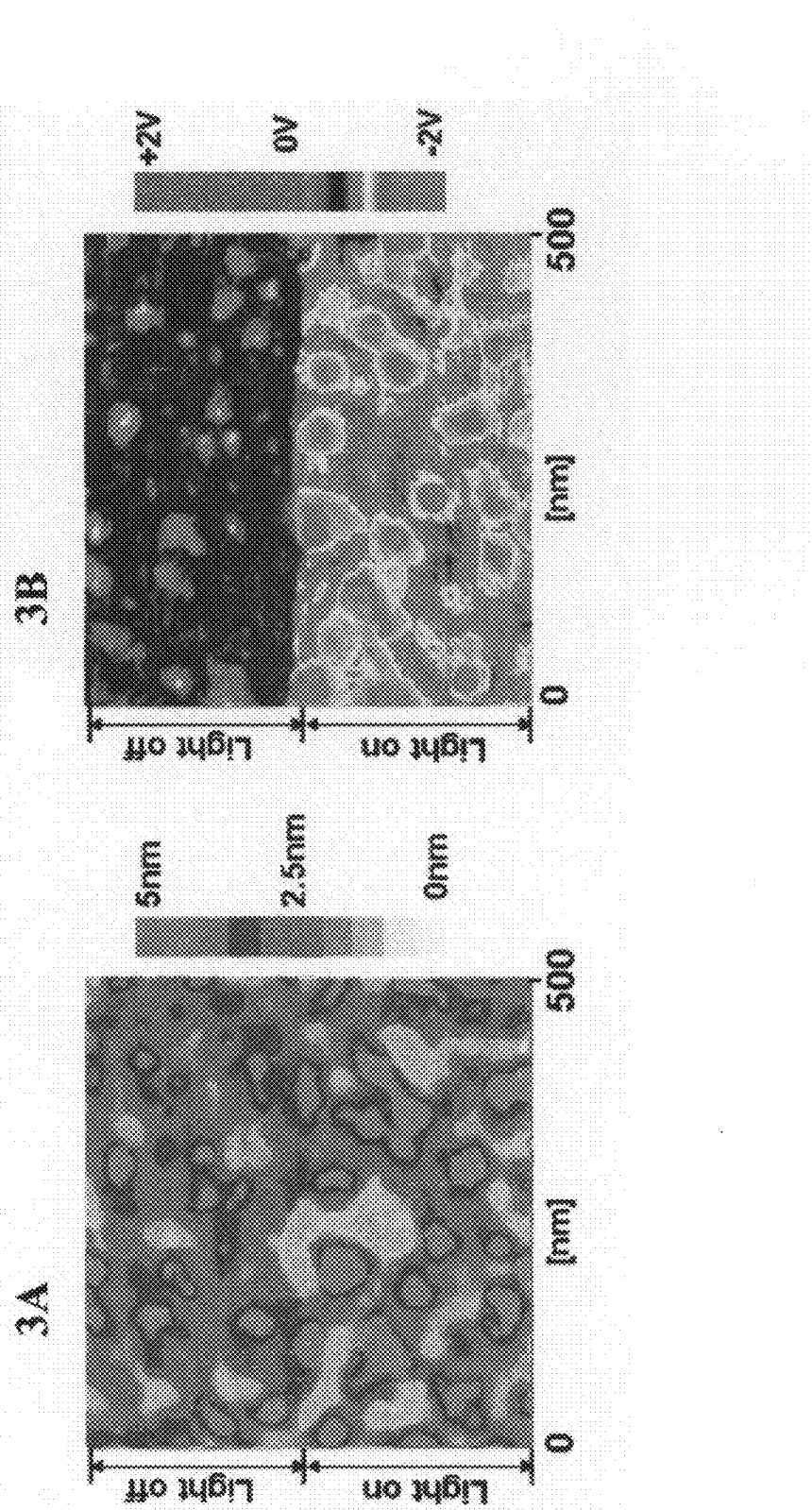
FIGs. 3A-B

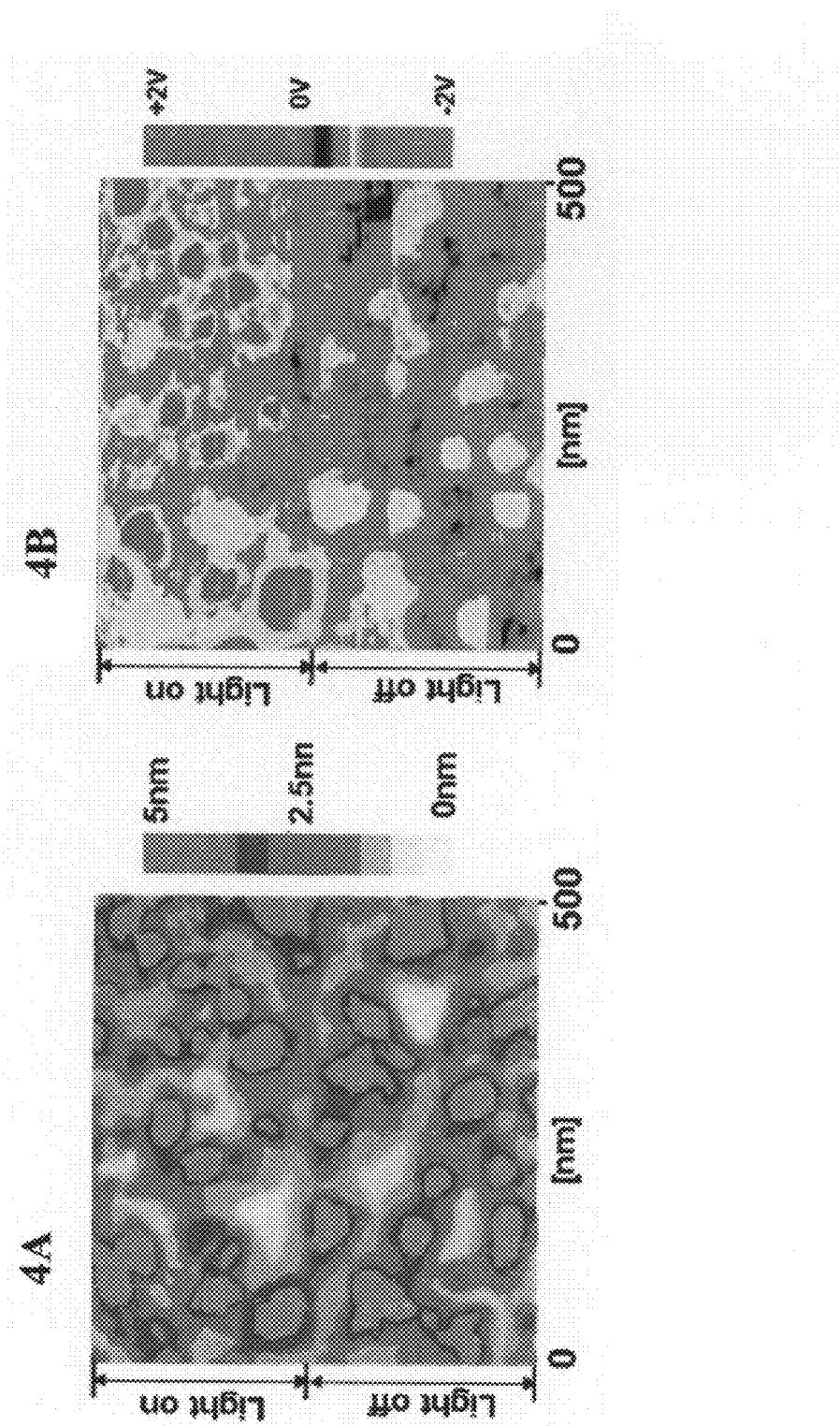
FIGs. 4A-B

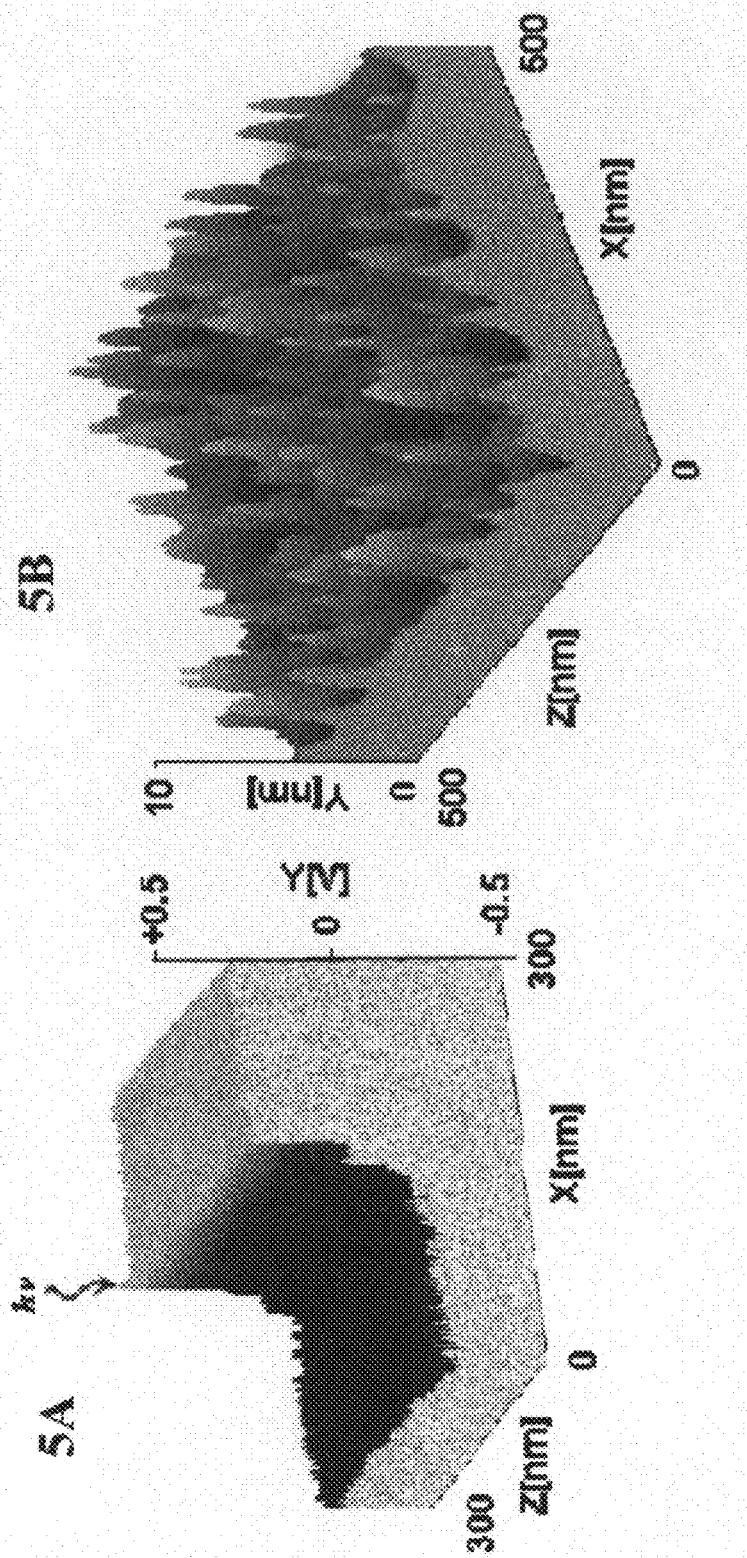
FIGs. 5A-B

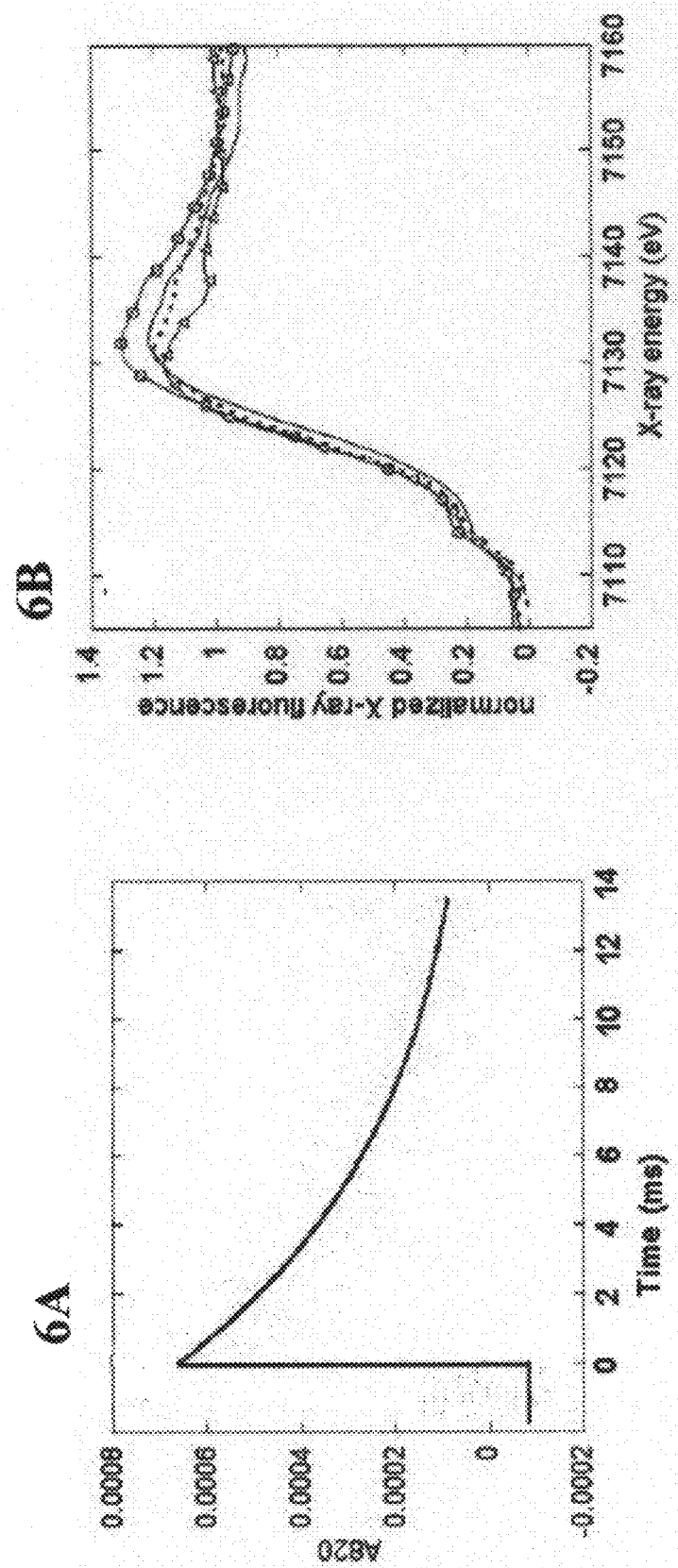
FIGs. 6A-B

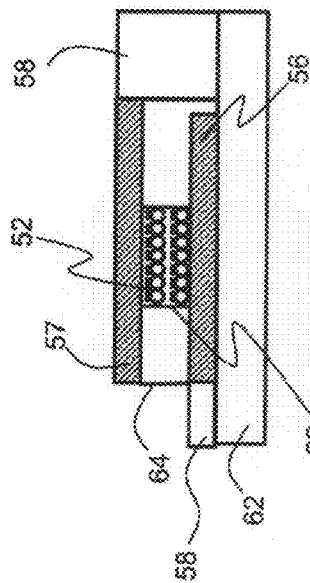
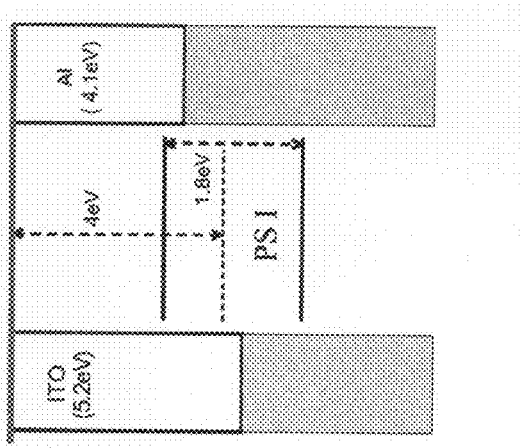
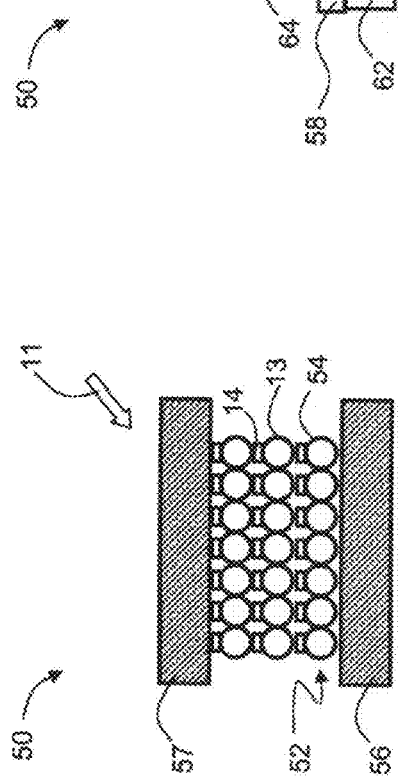
Fig. 11a
Fig. 11b
Fig. 12

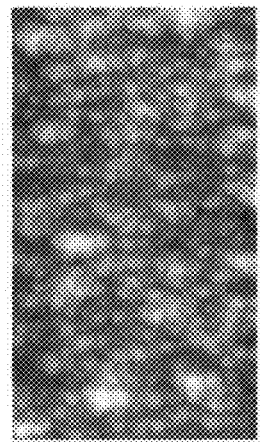
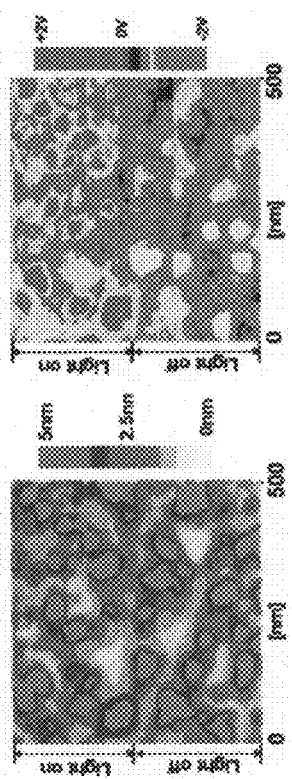
Fig. 17c
Fig. 17b
Fig. 17a

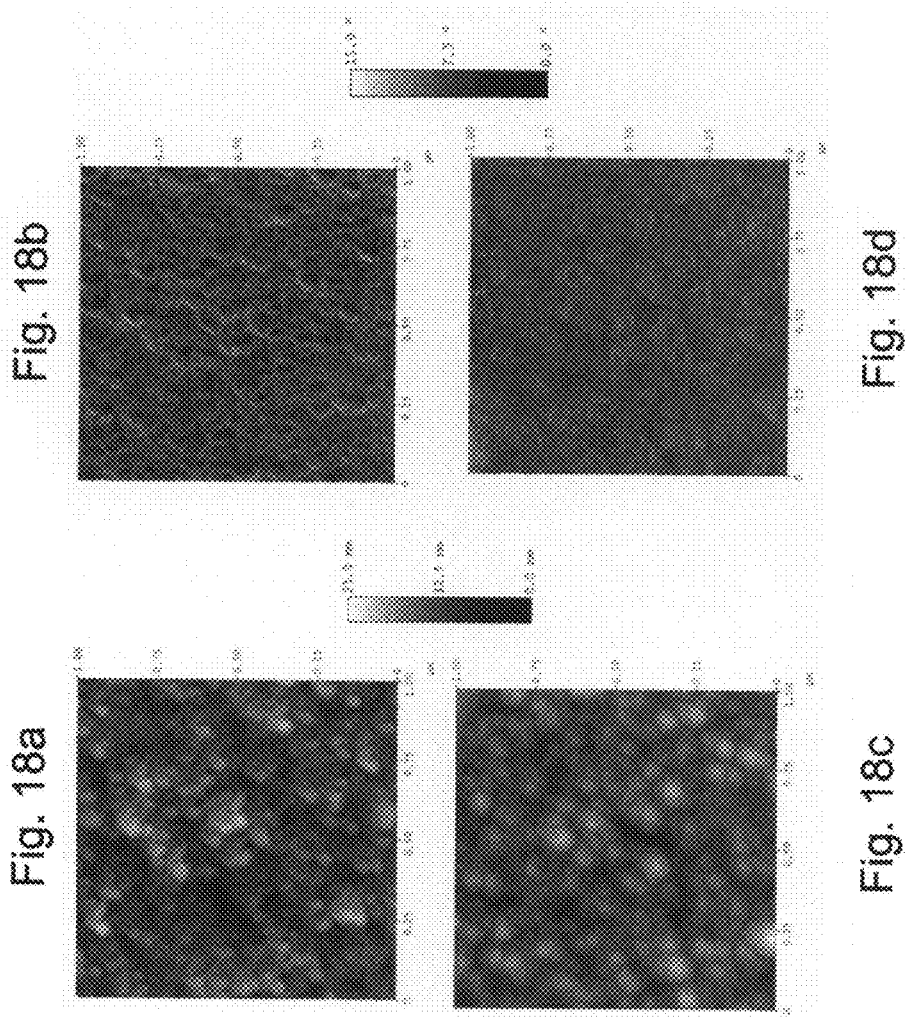

SEQUENCE LISTING

```
<160> NUMBER OF SEQ ID NOS: 38

<210> SEQ ID NO 1
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 1
gtgtatgcgg cgtgtcccga cactgctggc                                     30

<210> SEQ ID NO 2
<211> LENGTH: 30
```

```
<212> TYPE: DNA
<213> ORGANISM: Artificial sequence
<220> FEATURE:
<223> OTHER INFORMATION: Single strand DNA oligonucleotide

<400> SEQUENCE: 2
agcagtgtcg ggacacgccg catacacgcc                                              30

<210> SEQ ID NO 3
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 3 cacattttg gttgttctga aggtgctggt                                               30

<210> SEQ ID NO 4
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 4
agcaccttca gaacaaccaa aaatgtggcc                                              30

<210> SEQ ID NO 5
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 5
ctctccaatc cttgcagcat tgcttccacc                                              30

<210> SEQ ID NO 6
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 6
ggaagcaatg ctgcaaggat tggagagcaa                                              30

<210> SEQ ID NO 7
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 7
gatgctatca actgcggcac caactctctg                                              30

<210> SEQ ID NO 8
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 8
```
agagttggtg ccgcagttga tagcatccaa                                         30

<210> SEQ ID NO 9
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 9
ctcggtgttt ggtgcggtaa cgttgctcag                                         30

<210> SEQ ID NO 10
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 10
agcaacgtta ccgcaccaaa caccgaggtg                                         30

<210> SEQ ID NO 11
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 11
ggttacaacc cctgcggtgt caacaatctg                                         30

<210> SEQ ID NO 12
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 12
attgttgaca ccgcaggggt tgtaaccatt                                         30

<210> SEQ ID NO 13
<211> LENGTH: 60
<212> TYPE: DNA
<213> ORGANISM: Artificial sequence
<220> FEATURE:
<223> OTHER INFORMATION: Single strand DNA oligonucleotide

<400> SEQUENCE: 13
gtgtatgcgg cgtgtcccga cactgctggc ggttacaacc cctgcggtgt caacaatctg         60

<210> SEQ ID NO 14
<211> LENGTH: 60
<212> TYPE: DNA
<213> ORGANISM: Artificial sequence
<220> FEATURE:
<223> OTHER INFORMATION: Single strand DNA oligonucleotide

<400> SEQUENCE: 14
agcagtgtcg ggacacgccg catacacgcc attgttgaca ccgcaggggt tgtaaccatt         60

<210> SEQ ID NO 15
<211> LENGTH: 60
<212> TYPE: DNA
<213> ORGANISM: Artificial sequence

```
-continued

<220> FEATURE:
<223> OTHER INFORMATION: Single strand DNA oligonucleotide

<400> SEQUENCE: 15 cacattttg gttgttctga aggtgctggt ggttacaacc cctgcggtgt caacaatctg    60

<210> SEQ ID NO 16
<211> LENGTH: 60
<212> TYPE: DNA
<213> ORGANISM: Artificial sequence
<220> FEATURE:
<223> OTHER INFORMATION: Single strand DNA oligonucleotide

<400> SEQUENCE: 16
agcaccttca gaacaaccaa aaatgtggcc attgttgaca ccgcaggggt tgtaaccatt    60

<210> SEQ ID NO 17
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 17
gaaatggtgc cctggtgtgg ttgtaaagcc                                    30

<210> SEQ ID NO 18
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 18
agcggcttta caaccacacc agggcaccat                                    30

<210> SEQ ID NO 19
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 19
agatctttag tggtggtggt ggtggtggta agctaaaccc at                      42

<210> SEQ ID NO 20
<211> LENGTH: 731
<212> TYPE: PRT
<213> ORGANISM: Synechocystis sp.
<220> FEATURE:
<221> NAME/KEY: misc_feature
<223> OTHER INFORMATION: D479C mutant polypeptide

<400> SEQUENCE: 20
```

Met Ala Thr Lys Phe Pro Lys Phe Ser Gln Asp Leu Ala Gln Asp Pro
1               5                   10                  15

Thr Thr Arg Arg Ile Trp Tyr Gly Ile Ala Thr Ala His Asp Phe Glu
            20                  25                  30

Thr His Asp Gly Met Thr Glu Glu Asn Leu Tyr Gln Lys Ile Phe Ala
        35                  40                  45

Ser His Phe Gly His Ile Ala Ile Ile Phe Leu Trp Thr Ser Gly Thr
    50                  55                  60

Leu Phe His Val Ala Trp Gln Gly Asn Phe Glu Gln Trp Ile Lys Asp

-continued

```
                65                  70                  75                  80
            Pro Leu Asn Ile Arg Pro Ile Ala His Ala Ile Trp Asp Pro His Phe
                            85                  90                  95
            Gly Glu Gly Ala Val Asn Ala Phe Thr Gln Ala Gly Ala Ser Asn Pro
                        100                 105                 110
            Val Asn Ile Ala Tyr Ser Gly Val Tyr His Trp Phe Tyr Thr Ile Gly
                        115                 120                 125
            Met Thr Thr Asn Gln Glu Leu Tyr Ser Gly Ala Val Phe Leu Leu Val
                        130                 135                 140
            Leu Ala Ser Leu Phe Leu Phe Ala Gly Trp Leu His Leu Gln Pro Lys
            145                 150                 155                 160
            Phe Arg Pro Ser Leu Ala Trp Phe Lys Asn Ala Glu Ser Arg Leu Asn
                            165                 170                 175
            His His Leu Ala Gly Leu Phe Gly Val Ser Ser Leu Ala Trp Ala Gly
                        180                 185                 190
            His Leu Val His Val Ala Ile Pro Glu Ala Arg Gly Gln His Val Gly
                        195                 200                 205
            Trp Asp Asn Phe Leu Ser Thr Pro Pro His Pro Ala Gly Leu Met Pro
                    210                 215                 220
            Phe Phe Thr Gly Asn Trp Gly Val Tyr Ala Ala Asp Pro Asp Thr Ala
            225                 230                 235                 240
            Gly His Ile Phe Gly Thr Ser Glu Gly Ala Gly Thr Ala Ile Leu Thr
                            245                 250                 255
            Phe Leu Gly Gly Phe His Pro Gln Thr Glu Ser Leu Trp Leu Thr Asp
                        260                 265                 270
            Ile Ala His His His Leu Ala Ile Ala Val Ile Phe Ile Ile Ala Gly
                        275                 280                 285
            His Met Tyr Arg Thr Asn Trp Gly Ile Gly His Ser Ile Lys Glu Ile
                    290                 295                 300
            Leu Asn Ala His Lys Gly Pro Leu Thr Gly Ala Gly His Thr Asn Leu
            305                 310                 315                 320
            Tyr Asp Thr Ile Asn Asn Ser Leu His Phe Gln Leu Gly Leu Ala Leu
                            325                 330                 335
            Ala Ser Leu Gly Val Ile Thr Ser Leu Val Ala Gln His Met Tyr Ser
                        340                 345                 350
            Leu Pro Ser Tyr Ala Phe Ile Ala Gln Asp His Thr Thr Gln Ala Ala
                        355                 360                 365
            Leu Tyr Thr His His Gln Tyr Ile Ala Gly Phe Leu Met Val Gly Ala
                    370                 375                 380
            Phe Ala His Gly Ala Ile Phe Phe Val Arg Asp Tyr Asp Pro Val Ala
            385                 390                 395                 400
            Asn Lys Asp Asn Val Leu Ala Arg Met Leu Glu His Lys Glu Ala Leu
                            405                 410                 415
            Ile Ser His Leu Ser Trp Val Ser Leu Phe Leu Gly Phe His Thr Leu
                        420                 425                 430
            Gly Leu Tyr Val His Asn Asp Val Val Val Ala Phe Gly Thr Pro Glu
                        435                 440                 445
            Lys Gln Ile Leu Ile Glu Pro Val Phe Ala Gln Trp Ile Gln Ala Thr
                    450                 455                 460
            Ser Gly Lys Ala Leu Tyr Gly Phe Asp Val Leu Leu Ser Asn Pro Cys
            465                 470                 475                 480
            Ser Ile Ala Ser Thr Thr Gly Ala Ala Trp Leu Pro Gly Trp Leu Asp
                            485                 490                 495
```

```
Ala Ile Asn Ser Gly Thr Asn Ser Leu Phe Leu Thr Ile Gly Pro Gly
            500                 505                 510

Asp Phe Leu Val His His Ala Ile Ala Leu Gly Leu His Thr Thr Ala
            515                 520                 525

Leu Ile Leu Ile Lys Gly Ala Leu Asp Ala Arg Gly Ser Lys Leu Met
            530                 535                 540

Pro Asp Lys Lys Asp Phe Gly Tyr Ser Phe Pro Cys Asp Gly Pro Gly
545                 550                 555                 560

Arg Gly Gly Thr Cys Asp Ile Ser Ala Trp Asp Ala Phe Tyr Leu Ala
                565                 570                 575

Met Phe Trp Met Leu Asn Thr Leu Gly Trp Leu Thr Phe Tyr Trp His
            580                 585                 590

Trp Lys His Leu Gly Val Trp Ser Gly Asn Val Ala Gln Phe Asn Glu
            595                 600                 605

Asn Ser Thr Tyr Leu Met Gly Trp Phe Arg Asp Tyr Leu Trp Ala Asn
            610                 615                 620

Ser Ala Gln Leu Ile Asn Gly Tyr Asn Pro Tyr Gly Val Asn Asn Leu
625                 630                 635                 640

Ser Val Trp Ala Trp Met Phe Leu Phe Gly His Leu Val Trp Ala Thr
                645                 650                 655

Gly Phe Met Phe Leu Ile Ser Trp Arg Gly Tyr Trp Gln Glu Leu Ile
            660                 665                 670

Glu Thr Ile Val Trp Ala His Glu Arg Thr Pro Leu Ala Asn Leu Val
            675                 680                 685

Arg Trp Lys Asp Lys Pro Val Ala Leu Ser Ile Val Gln Ala Arg Leu
690                 695                 700

Val Gly Leu Ala His Phe Thr Val Gly Tyr Val Leu Thr Tyr Ala Ala
705                 710                 715                 720

Phe Leu Ile Ala Ser Thr Ala Gly Lys Phe Gly
                725                 730

<210> SEQ ID NO 21
<211> LENGTH: 731
<212> TYPE: PRT
<213> ORGANISM: Synechocystis sp.
<220> FEATURE:
<221> NAME/KEY: misc_feature
<223> OTHER INFORMATION: S499C mutant polypeptide

<400> SEQUENCE: 21

Met Ala Thr Lys Phe Pro Lys Phe Ser Gln Asp Leu Ala Gln Asp Pro
1               5                   10                  15

Thr Thr Arg Arg Ile Trp Tyr Gly Ile Ala Thr Ala His Asp Phe Glu
            20                  25                  30

Thr His Asp Gly Met Thr Glu Glu Asn Leu Tyr Gln Lys Ile Phe Ala
        35                  40                  45

Ser His Phe Gly His Ile Ala Ile Ile Phe Leu Trp Thr Ser Gly Thr
    50                  55                  60

Leu Phe His Val Ala Trp Gln Gly Asn Phe Glu Gln Trp Ile Lys Asp
65                  70                  75                  80

Pro Leu Asn Ile Arg Pro Ile Ala His Ala Ile Trp Asp Pro His Phe
                85                  90                  95

Gly Glu Gly Ala Val Asn Ala Phe Thr Gln Ala Gly Ala Ser Asn Pro
            100                 105                 110

Val Asn Ile Ala Tyr Ser Gly Val Tyr His Trp Phe Tyr Thr Ile Gly
```

```
                        115                 120                 125
Met Thr Thr Asn Gln Glu Leu Tyr Ser Gly Ala Val Phe Leu Val
    130                 135                 140
Leu Ala Ser Leu Phe Leu Phe Ala Gly Trp Leu His Leu Gln Pro Lys
145                 150                 155                 160
Phe Arg Pro Ser Leu Ala Trp Phe Lys Asn Ala Glu Ser Arg Leu Asn
                165                 170                 175
His His Leu Ala Gly Leu Phe Gly Val Ser Ser Leu Ala Trp Ala Gly
            180                 185                 190
His Leu Val His Val Ala Ile Pro Glu Ala Arg Gly Gln His Val Gly
            195                 200                 205
Trp Asp Asn Phe Leu Ser Thr Pro His Pro Ala Gly Leu Met Pro
    210                 215                 220
Phe Phe Thr Gly Asn Trp Gly Val Tyr Ala Ala Asp Pro Asp Thr Ala
225                 230                 235                 240
Gly His Ile Phe Gly Thr Ser Glu Gly Ala Gly Thr Ala Ile Leu Thr
                245                 250                 255
Phe Leu Gly Gly Phe His Pro Gln Thr Glu Ser Leu Trp Leu Thr Asp
            260                 265                 270
Ile Ala His His His Leu Ala Ile Ala Val Ile Phe Ile Ala Gly
            275                 280                 285
His Met Tyr Arg Thr Asn Trp Gly Ile Gly His Ser Ile Lys Glu Ile
    290                 295                 300
Leu Asn Ala His Lys Gly Pro Leu Thr Gly Ala Gly His Thr Asn Leu
305                 310                 315                 320
Tyr Asp Thr Ile Asn Asn Ser Leu His Phe Gln Leu Gly Leu Ala Leu
                325                 330                 335
Ala Ser Leu Gly Val Ile Thr Ser Leu Val Ala Gln His Met Tyr Ser
            340                 345                 350
Leu Pro Ser Tyr Ala Phe Ile Ala Gln Asp His Thr Thr Gln Ala Ala
    355                 360                 365
Leu Tyr Thr His His Gln Tyr Ile Ala Gly Phe Leu Met Val Gly Ala
    370                 375                 380
Phe Ala His Gly Ala Ile Phe Phe Val Arg Asp Tyr Asp Pro Val Ala
385                 390                 395                 400
Asn Lys Asp Asn Val Leu Ala Arg Met Leu Glu His Lys Glu Ala Leu
                405                 410                 415
Ile Ser His Leu Ser Trp Val Ser Leu Phe Leu Gly Phe His Thr Leu
            420                 425                 430
Gly Leu Tyr Val His Asn Asp Val Val Ala Phe Gly Thr Pro Glu
            435                 440                 445
Lys Gln Ile Leu Ile Glu Pro Val Phe Ala Gln Trp Ile Gln Ala Thr
    450                 455                 460
Ser Gly Lys Ala Leu Tyr Gly Phe Asp Val Leu Leu Ser Asn Pro Asp
465                 470                 475                 480
Ser Ile Ala Ser Thr Thr Gly Ala Ala Trp Leu Pro Gly Trp Leu Asp
                485                 490                 495
Ala Ile Asn Cys Gly Thr Asn Ser Leu Phe Leu Thr Ile Gly Pro Gly
            500                 505                 510
Asp Phe Leu Val His His Ala Ile Ala Leu Gly Leu His Thr Thr Ala
    515                 520                 525
Leu Ile Leu Ile Lys Gly Ala Leu Asp Ala Arg Gly Ser Lys Leu Met
530                 535                 540
```

```
Pro Asp Lys Lys Asp Phe Gly Tyr Ser Phe Pro Cys Asp Gly Pro Gly
545                 550                 555                 560

Arg Gly Gly Thr Cys Asp Ile Ser Ala Trp Asp Ala Phe Tyr Leu Ala
                565                 570                 575

Met Phe Trp Met Leu Asn Thr Leu Gly Trp Leu Thr Phe Tyr Trp His
            580                 585                 590

Trp Lys His Leu Gly Val Trp Ser Gly Asn Val Ala Gln Phe Asn Glu
        595                 600                 605

Asn Ser Thr Tyr Leu Met Gly Trp Phe Arg Asp Tyr Leu Trp Ala Asn
610                 615                 620

Ser Ala Gln Leu Ile Asn Gly Tyr Asn Pro Tyr Gly Val Asn Asn Leu
625                 630                 635                 640

Ser Val Trp Ala Trp Met Phe Leu Phe Gly His Leu Val Trp Ala Thr
                645                 650                 655

Gly Phe Met Phe Leu Ile Ser Trp Arg Gly Tyr Trp Gln Glu Leu Ile
            660                 665                 670

Glu Thr Ile Val Trp Ala His Glu Arg Thr Pro Leu Ala Asn Leu Val
        675                 680                 685

Arg Trp Lys Asp Lys Pro Val Ala Leu Ser Ile Val Gln Ala Arg Leu
690                 695                 700

Val Gly Leu Ala His Phe Thr Val Gly Tyr Val Leu Thr Tyr Ala Ala
705                 710                 715                 720

Phe Leu Ile Ala Ser Thr Ala Gly Lys Phe Gly
                725                 730
```

<210> SEQ ID NO 22
<211> LENGTH: 731
<212> TYPE: PRT
<213> ORGANISM: Synechocystis sp.
<220> FEATURE:
<221> NAME/KEY: misc_feature
<223> OTHER INFORMATION: S599C mutant polypeptide

<400> SEQUENCE: 22

```
Met Ala Thr Lys Phe Pro Lys Phe Ser Gln Asp Leu Ala Gln Asp Pro
1               5                   10                  15

Thr Thr Arg Arg Ile Trp Tyr Gly Ile Ala Thr Ala His Asp Phe Glu
                20                  25                  30

Thr His Asp Gly Met Thr Glu Glu Asn Leu Tyr Gln Lys Ile Phe Ala
            35                  40                  45

Ser His Phe Gly His Ile Ala Ile Phe Leu Trp Thr Ser Gly Thr
        50                  55                  60

Leu Phe His Val Ala Trp Gln Gly Asn Phe Glu Gln Trp Ile Lys Asp
65                  70                  75                  80

Pro Leu Asn Ile Arg Pro Ile Ala His Ala Ile Trp Asp Pro His Phe
                85                  90                  95

Gly Glu Gly Ala Val Asn Ala Phe Thr Gln Ala Gly Ala Ser Asn Pro
            100                 105                 110

Val Asn Ile Ala Tyr Ser Gly Val Tyr His Trp Phe Tyr Thr Ile Gly
        115                 120                 125

Met Thr Thr Asn Gln Glu Leu Tyr Ser Gly Ala Val Phe Leu Leu Val
    130                 135                 140

Leu Ala Ser Leu Phe Leu Phe Ala Gly Trp Leu His Leu Gln Pro Lys
145                 150                 155                 160

Phe Arg Pro Ser Leu Ala Trp Phe Lys Asn Ala Glu Ser Arg Leu Asn
```

-continued

```
              165                 170                 175
His His Leu Ala Gly Leu Phe Gly Val Ser Ser Leu Ala Trp Ala Gly
            180                 185                 190

His Leu Val His Val Ala Ile Pro Glu Ala Arg Gly Gln His Val Gly
            195                 200                 205

Trp Asp Asn Phe Leu Ser Thr Pro Pro His Pro Ala Gly Leu Met Pro
210                 215                 220

Phe Phe Thr Gly Asn Trp Gly Val Tyr Ala Ala Asp Pro Asp Thr Ala
225                 230                 235                 240

Gly His Ile Phe Gly Thr Ser Glu Gly Ala Gly Thr Ala Ile Leu Thr
                245                 250                 255

Phe Leu Gly Gly Phe His Pro Gln Thr Glu Ser Leu Trp Leu Thr Asp
            260                 265                 270

Ile Ala His His His Leu Ala Ile Ala Val Ile Phe Ile Ile Ala Gly
            275                 280                 285

His Met Tyr Arg Thr Asn Trp Gly Ile Gly His Ser Ile Lys Glu Ile
            290                 295                 300

Leu Asn Ala His Lys Gly Pro Leu Thr Gly Ala Gly His Thr Asn Leu
305                 310                 315                 320

Tyr Asp Thr Ile Asn Asn Ser Leu His Phe Gln Leu Gly Leu Ala Leu
                325                 330                 335

Ala Ser Leu Gly Val Ile Thr Ser Leu Val Ala Gln His Met Tyr Ser
            340                 345                 350

Leu Pro Ser Tyr Ala Phe Ile Ala Gln Asp His Thr Thr Gln Ala Ala
            355                 360                 365

Leu Tyr Thr His His Gln Tyr Ile Ala Gly Phe Leu Met Val Gly Ala
            370                 375                 380

Phe Ala His Gly Ala Ile Phe Phe Val Arg Asp Tyr Asp Pro Val Ala
385                 390                 395                 400

Asn Lys Asp Asn Val Leu Ala Arg Met Leu Glu His Lys Glu Ala Leu
                405                 410                 415

Ile Ser His Leu Ser Trp Val Ser Leu Phe Leu Gly Phe His Thr Leu
            420                 425                 430

Gly Leu Tyr Val His Asn Asp Val Val Val Ala Phe Gly Thr Pro Glu
            435                 440                 445

Lys Gln Ile Leu Ile Glu Pro Val Phe Ala Gln Trp Ile Gln Ala Thr
            450                 455                 460

Ser Gly Lys Ala Leu Tyr Gly Phe Asp Val Leu Leu Ser Asn Pro Asp
465                 470                 475                 480

Ser Ile Ala Ser Thr Thr Gly Ala Ala Trp Leu Pro Gly Trp Leu Asp
                485                 490                 495

Ala Ile Asn Ser Gly Thr Asn Ser Leu Phe Leu Thr Ile Gly Pro Gly
            500                 505                 510

Asp Phe Leu Val His His Ala Ile Ala Leu Gly Leu His Thr Thr Ala
            515                 520                 525

Leu Ile Leu Ile Lys Gly Ala Leu Asp Ala Arg Gly Ser Lys Leu Met
            530                 535                 540

Pro Asp Lys Lys Asp Phe Gly Tyr Ser Phe Pro Cys Asp Gly Pro Gly
545                 550                 555                 560

Arg Gly Gly Thr Cys Asp Ile Ser Ala Trp Asp Ala Phe Tyr Leu Ala
                565                 570                 575

Met Phe Trp Met Leu Asn Thr Leu Gly Trp Leu Thr Phe Tyr Trp His
            580                 585                 590
```

Trp Lys His Leu Gly Val Trp Cys Gly Asn Val Ala Gln Phe Asn Glu
            595                 600                 605

Asn Ser Thr Tyr Leu Met Gly Trp Phe Arg Asp Tyr Leu Trp Ala Asn
            610                 615                 620

Ser Ala Gln Leu Ile Asn Gly Tyr Asn Pro Tyr Gly Val Asn Asn Leu
625                 630                 635                 640

Ser Val Trp Ala Trp Met Phe Leu Phe Gly His Leu Val Trp Ala Thr
            645                 650                 655

Gly Phe Met Phe Leu Ile Ser Trp Arg Gly Tyr Trp Gln Glu Leu Ile
            660                 665                 670

Glu Thr Ile Val Trp Ala His Glu Arg Thr Pro Leu Ala Asn Leu Val
            675                 680                 685

Arg Trp Lys Asp Lys Pro Val Ala Leu Ser Ile Val Gln Ala Arg Leu
            690                 695                 700

Val Gly Leu Ala His Phe Thr Val Gly Tyr Val Leu Thr Tyr Ala Ala
705                 710                 715                 720

Phe Leu Ile Ala Ser Thr Ala Gly Lys Phe Gly
            725                 730

<210> SEQ ID NO 23
<211> LENGTH: 731
<212> TYPE: PRT
<213> ORGANISM: Synechocystis sp.
<220> FEATURE:
<221> NAME/KEY: misc_feature
<223> OTHER INFORMATION: Y634C mutant polypeptide

<400> SEQUENCE: 23

Met Ala Thr Lys Phe Pro Lys Phe Ser Gln Asp Leu Ala Gln Asp Pro
1               5                   10                  15

Thr Thr Arg Arg Ile Trp Tyr Gly Ile Ala Thr Ala His Asp Phe Glu
            20                  25                  30

Thr His Asp Gly Met Thr Glu Glu Asn Leu Tyr Gln Lys Ile Phe Ala
        35                  40                  45

Ser His Phe Gly His Ile Ala Ile Ile Phe Leu Trp Thr Ser Gly Thr
    50                  55                  60

Leu Phe His Val Ala Trp Gln Gly Asn Phe Glu Gln Trp Ile Lys Asp
65                  70                  75                  80

Pro Leu Asn Ile Arg Pro Ile Ala His Ala Ile Trp Asp Pro His Phe
                85                  90                  95

Gly Glu Gly Ala Val Asn Ala Phe Thr Gln Ala Gly Ala Ser Asn Pro
            100                 105                 110

Val Asn Ile Ala Tyr Ser Gly Val Tyr His Trp Phe Tyr Thr Ile Gly
        115                 120                 125

Met Thr Thr Asn Gln Glu Leu Tyr Ser Gly Ala Val Phe Leu Leu Val
130                 135                 140

Leu Ala Ser Leu Phe Leu Phe Ala Gly Trp Leu His Leu Gln Pro Lys
145                 150                 155                 160

Phe Arg Pro Ser Leu Ala Trp Phe Lys Asn Ala Glu Ser Arg Leu Asn
                165                 170                 175

His His Leu Ala Gly Leu Phe Gly Val Ser Ser Leu Ala Trp Ala Gly
            180                 185                 190

His Leu Val His Val Ala Ile Pro Glu Ala Arg Gly Gln His Val Gly
        195                 200                 205

Trp Asp Asn Phe Leu Ser Thr Pro Pro His Pro Ala Gly Leu Met Pro

-continued

```
                210                 215                 220
Phe Phe Thr Gly Asn Trp Gly Val Tyr Ala Ala Asp Pro Asp Thr Ala
225                 230                 235                 240

Gly His Ile Phe Gly Thr Ser Glu Gly Ala Gly Thr Ala Ile Leu Thr
                245                 250                 255

Phe Leu Gly Gly Phe His Pro Gln Thr Glu Ser Leu Trp Leu Thr Asp
                260                 265                 270

Ile Ala His His His Leu Ala Ile Ala Val Ile Phe Ile Ile Ala Gly
                275                 280                 285

His Met Tyr Arg Thr Asn Trp Gly Ile Gly His Ser Ile Lys Glu Ile
290                 295                 300

Leu Asn Ala His Lys Gly Pro Leu Thr Gly Ala Gly His Thr Asn Leu
305                 310                 315                 320

Tyr Asp Thr Ile Asn Asn Ser Leu His Phe Gln Leu Gly Leu Ala Leu
                325                 330                 335

Ala Ser Leu Gly Val Ile Thr Ser Leu Val Ala Gln His Met Tyr Ser
                340                 345                 350

Leu Pro Ser Tyr Ala Phe Ile Ala Gln Asp His Thr Thr Gln Ala Ala
                355                 360                 365

Leu Tyr Thr His His Gln Tyr Ile Ala Gly Phe Leu Met Val Gly Ala
                370                 375                 380

Phe Ala His Gly Ala Ile Phe Phe Val Arg Asp Tyr Asp Pro Val Ala
385                 390                 395                 400

Asn Lys Asp Asn Val Leu Ala Arg Met Leu Glu His Lys Glu Ala Leu
                405                 410                 415

Ile Ser His Leu Ser Trp Val Ser Leu Phe Leu Gly Phe His Thr Leu
                420                 425                 430

Gly Leu Tyr Val His Asn Asp Val Val Ala Phe Gly Thr Pro Glu
                435                 440                 445

Lys Gln Ile Leu Ile Glu Pro Val Phe Ala Gln Trp Ile Gln Ala Thr
450                 455                 460

Ser Gly Lys Ala Leu Tyr Gly Phe Asp Val Leu Leu Ser Asn Pro Asp
465                 470                 475                 480

Ser Ile Ala Ser Thr Thr Gly Ala Ala Trp Leu Pro Gly Trp Leu Asp
                485                 490                 495

Ala Ile Asn Ser Gly Thr Asn Ser Leu Phe Leu Thr Ile Gly Pro Gly
                500                 505                 510

Asp Phe Leu Val His His Ala Ile Ala Leu Gly Leu His Thr Thr Ala
                515                 520                 525

Leu Ile Leu Ile Lys Gly Ala Leu Asp Ala Arg Gly Ser Lys Leu Met
530                 535                 540

Pro Asp Lys Lys Asp Phe Gly Tyr Ser Phe Pro Cys Asp Gly Pro Gly
545                 550                 555                 560

Arg Gly Gly Thr Cys Asp Ile Ser Ala Trp Asp Ala Phe Tyr Leu Ala
                565                 570                 575

Met Phe Trp Met Leu Asn Thr Leu Gly Trp Leu Thr Phe Tyr Trp His
                580                 585                 590

Trp Lys His Leu Gly Val Trp Ser Gly Asn Val Ala Gln Phe Asn Glu
                595                 600                 605

Asn Ser Thr Tyr Leu Met Gly Trp Phe Arg Asp Tyr Leu Trp Ala Asn
                610                 615                 620

Ser Ala Gln Leu Ile Asn Gly Tyr Asn Pro Cys Gly Val Asn Asn Leu
625                 630                 635                 640
```

```
Ser Val Trp Ala Trp Met Phe Leu Phe Gly His Leu Val Trp Ala Thr
                645                 650                 655

Gly Phe Met Phe Leu Ile Ser Trp Arg Gly Tyr Trp Gln Glu Leu Ile
            660                 665                 670

Glu Thr Ile Val Trp Ala His Glu Arg Thr Pro Leu Ala Asn Leu Val
        675                 680                 685

Arg Trp Lys Asp Lys Pro Val Ala Leu Ser Ile Val Gln Ala Arg Leu
    690                 695                 700

Val Gly Leu Ala His Phe Thr Val Gly Tyr Val Leu Thr Tyr Ala Ala
705                 710                 715                 720

Phe Leu Ile Ala Ser Thr Ala Gly Lys Phe Gly
                725                 730

<210> SEQ ID NO 24
<211> LENGTH: 731
<212> TYPE: PRT
<213> ORGANISM: Synechocystis sp.
<220> FEATURE:
<221> NAME/KEY: misc_feature
<223> OTHER INFORMATION: D235C mutant polypeptide

<400> SEQUENCE: 24

Met Ala Thr Lys Phe Pro Lys Phe Ser Gln Asp Leu Ala Gln Asp Pro
1               5                   10                  15

Thr Thr Arg Arg Ile Trp Tyr Gly Ile Ala Thr Ala His Asp Phe Glu
            20                  25                  30

Thr His Asp Gly Met Thr Glu Glu Asn Leu Tyr Gln Lys Ile Phe Ala
        35                  40                  45

Ser His Phe Gly His Ile Ala Ile Ile Phe Leu Trp Thr Ser Gly Thr
    50                  55                  60

Leu Phe His Val Ala Trp Gln Gly Asn Phe Glu Gln Trp Ile Lys Asp
65                  70                  75                  80

Pro Leu Asn Ile Arg Pro Ile Ala His Ala Ile Trp Asp Pro His Phe
                85                  90                  95

Gly Glu Gly Ala Val Asn Ala Phe Thr Gln Ala Gly Ala Ser Asn Pro
            100                 105                 110

Val Asn Ile Ala Tyr Ser Gly Val Tyr His Trp Phe Tyr Thr Ile Gly
        115                 120                 125

Met Thr Thr Asn Gln Glu Leu Tyr Ser Gly Ala Val Phe Leu Leu Val
    130                 135                 140

Leu Ala Ser Leu Phe Leu Phe Ala Gly Trp Leu His Leu Gln Pro Lys
145                 150                 155                 160

Phe Arg Pro Ser Leu Ala Trp Phe Lys Asn Ala Glu Ser Arg Leu Asn
                165                 170                 175

His His Leu Ala Gly Leu Phe Gly Val Ser Ser Leu Ala Trp Ala Gly
            180                 185                 190

His Leu Val His Val Ala Ile Pro Glu Ala Arg Gly Gln His Val Gly
        195                 200                 205

Trp Asp Asn Phe Leu Ser Thr Pro Pro His Pro Ala Gly Leu Met Pro
    210                 215                 220

Phe Phe Thr Gly Asn Trp Gly Val Tyr Ala Ala Cys Pro Asp Thr Ala
225                 230                 235                 240

Gly His Ile Phe Gly Thr Ser Glu Gly Ala Gly Thr Ala Ile Leu Thr
                245                 250                 255

Phe Leu Gly Gly Phe His Pro Gln Thr Glu Ser Leu Trp Leu Thr Asp
```

-continued

```
                260                 265                 270
Ile Ala His His His Leu Ala Ile Ala Val Ile Phe Ile Ile Ala Gly
            275                 280                 285
His Met Tyr Arg Thr Asn Trp Gly Ile Gly His Ser Ile Lys Glu Ile
    290                 295                 300
Leu Asn Ala His Lys Gly Pro Leu Thr Gly Ala Gly His Thr Asn Leu
305                 310                 315                 320
Tyr Asp Thr Ile Asn Asn Ser Leu His Phe Gln Leu Gly Leu Ala Leu
                325                 330                 335
Ala Ser Leu Gly Val Ile Thr Ser Leu Val Ala Gln His Met Tyr Ser
            340                 345                 350
Leu Pro Ser Tyr Ala Phe Ile Ala Gln Asp His Thr Thr Gln Ala Ala
            355                 360                 365
Leu Tyr Thr His His Gln Tyr Ile Ala Gly Phe Leu Met Val Gly Ala
    370                 375                 380
Phe Ala His Gly Ala Ile Phe Phe Val Arg Asp Tyr Asp Pro Val Ala
385                 390                 395                 400
Asn Lys Asp Asn Val Leu Ala Arg Met Leu Glu His Lys Glu Ala Leu
                405                 410                 415
Ile Ser His Leu Ser Trp Val Ser Leu Phe Leu Gly Phe His Thr Leu
            420                 425                 430
Gly Leu Tyr Val His Asn Asp Val Val Ala Phe Gly Thr Pro Glu
    435                 440                 445
Lys Gln Ile Leu Ile Glu Pro Val Phe Ala Gln Trp Ile Gln Ala Thr
    450                 455                 460
Ser Gly Lys Ala Leu Tyr Gly Phe Asp Val Leu Leu Ser Asn Pro Asp
465                 470                 475                 480
Ser Ile Ala Ser Thr Thr Gly Ala Ala Trp Leu Pro Gly Trp Leu Asp
            485                 490                 495
Ala Ile Asn Ser Gly Thr Asn Ser Leu Phe Leu Thr Ile Gly Pro Gly
                500                 505                 510
Asp Phe Leu Val His His Ala Ile Ala Leu Gly Leu His Thr Thr Ala
            515                 520                 525
Leu Ile Leu Ile Lys Gly Ala Leu Asp Ala Arg Gly Ser Lys Leu Met
    530                 535                 540
Pro Asp Lys Lys Asp Phe Gly Tyr Ser Phe Pro Cys Asp Gly Pro Gly
545                 550                 555                 560
Arg Gly Gly Thr Cys Asp Ile Ser Ala Trp Asp Ala Phe Tyr Leu Ala
                565                 570                 575
Met Phe Trp Met Leu Asn Thr Leu Gly Trp Leu Thr Phe Tyr Trp His
            580                 585                 590
Trp Lys His Leu Gly Val Trp Ser Gly Asn Val Ala Gln Phe Asn Glu
    595                 600                 605
Asn Ser Thr Tyr Leu Met Gly Trp Phe Arg Asp Tyr Leu Trp Ala Asn
    610                 615                 620
Ser Ala Gln Leu Ile Asn Gly Tyr Asn Pro Tyr Gly Val Asn Asn Leu
625                 630                 635                 640
Ser Val Trp Ala Trp Met Phe Leu Phe Gly His Leu Val Trp Ala Thr
                645                 650                 655
Gly Phe Met Phe Leu Ile Ser Trp Arg Gly Tyr Trp Gln Glu Leu Ile
            660                 665                 670
Glu Thr Ile Val Trp Ala His Glu Arg Thr Pro Leu Ala Asn Leu Val
    675                 680                 685
```

```
Arg Trp Lys Asp Lys Pro Val Ala Leu Ser Ile Val Gln Ala Arg Leu
    690                 695                 700
Val Gly Leu Ala His Phe Thr Val Gly Tyr Val Leu Thr Tyr Ala Ala
705                 710                 715                 720
Phe Leu Ile Ala Ser Thr Ala Gly Lys Phe Gly
                725                 730

<210> SEQ ID NO 25
<211> LENGTH: 731
<212> TYPE: PRT
<213> ORGANISM: Synechocystis sp.
<220> FEATURE:
<221> NAME/KEY: misc_feature
<223> OTHER INFORMATION: S246C mutant polypeptide

<400> SEQUENCE: 25

Met Ala Thr Lys Phe Pro Lys Phe Ser Gln Asp Leu Ala Gln Asp Pro
1               5                   10                  15
Thr Thr Arg Arg Ile Trp Tyr Gly Ile Ala Thr Ala His Asp Phe Glu
                20                  25                  30
Thr His Asp Gly Met Thr Glu Glu Asn Leu Tyr Gln Lys Ile Phe Ala
            35                  40                  45
Ser His Phe Gly His Ile Ala Ile Ile Phe Leu Trp Thr Ser Gly Thr
        50                  55                  60
Leu Phe His Val Ala Trp Gln Gly Asn Phe Glu Gln Trp Ile Lys Asp
65                  70                  75                  80
Pro Leu Asn Ile Arg Pro Ile Ala His Ala Ile Trp Asp Pro His Phe
                85                  90                  95
Gly Glu Gly Ala Val Asn Ala Phe Thr Gln Ala Gly Ala Ser Asn Pro
            100                 105                 110
Val Asn Ile Ala Tyr Ser Gly Val Tyr His Trp Phe Tyr Thr Ile Gly
        115                 120                 125
Met Thr Thr Asn Gln Glu Leu Tyr Ser Gly Ala Val Phe Leu Leu Val
130                 135                 140
Leu Ala Ser Leu Phe Leu Phe Ala Gly Trp Leu His Leu Gln Pro Lys
145                 150                 155                 160
Phe Arg Pro Ser Leu Ala Trp Phe Lys Asn Ala Glu Ser Arg Leu Asn
                165                 170                 175
His His Leu Ala Gly Leu Phe Gly Val Ser Ser Leu Ala Trp Ala Gly
            180                 185                 190
His Leu Val His Val Ala Ile Pro Glu Ala Arg Gly Gln His Val Gly
        195                 200                 205
Trp Asp Asn Phe Leu Ser Thr Pro Pro His Pro Ala Gly Leu Met Pro
210                 215                 220
Phe Phe Thr Gly Asn Trp Gly Val Tyr Ala Ala Asp Pro Asp Thr Ala
225                 230                 235                 240
Gly His Ile Phe Gly Thr Cys Glu Gly Ala Gly Thr Ala Ile Leu Thr
                245                 250                 255
Phe Leu Gly Gly Phe His Pro Gln Thr Glu Ser Leu Trp Leu Thr Asp
            260                 265                 270
Ile Ala His His His Leu Ala Ile Ala Val Ile Phe Ile Ile Ala Gly
        275                 280                 285
His Met Tyr Arg Thr Asn Trp Gly Ile Gly His Ser Ile Lys Glu Ile
290                 295                 300
Leu Asn Ala His Lys Gly Pro Leu Thr Gly Ala Gly His Thr Asn Leu
```

-continued

```
                305                 310                 315                 320
Tyr Asp Thr Ile Asn Asn Ser Leu His Phe Gln Leu Gly Leu Ala Leu
                    325                 330                 335
Ala Ser Leu Gly Val Ile Thr Ser Leu Val Ala Gln His Met Tyr Ser
                    340                 345                 350
Leu Pro Ser Tyr Ala Phe Ile Ala Gln Asp His Thr Gln Ala Ala
                    355                 360                 365
Leu Tyr Thr His His Gln Tyr Ile Ala Gly Phe Leu Met Val Gly Ala
                370                 375                 380
Phe Ala His Gly Ala Ile Phe Phe Val Arg Asp Tyr Asp Pro Val Ala
385                 390                 395                 400
Asn Lys Asp Asn Val Leu Ala Arg Met Leu Glu His Lys Glu Ala Leu
                    405                 410                 415
Ile Ser His Leu Ser Trp Val Ser Leu Phe Leu Gly Phe His Thr Leu
                    420                 425                 430
Gly Leu Tyr Val His Asn Asp Val Val Ala Phe Gly Thr Pro Glu
                    435                 440                 445
Lys Gln Ile Leu Ile Glu Pro Val Phe Ala Gln Trp Ile Gln Ala Thr
                450                 455                 460
Ser Gly Lys Ala Leu Tyr Gly Phe Asp Val Leu Leu Ser Asn Pro Asp
465                 470                 475                 480
Ser Ile Ala Ser Thr Thr Gly Ala Ala Trp Leu Pro Gly Trp Leu Asp
                    485                 490                 495
Ala Ile Asn Ser Gly Thr Asn Ser Leu Phe Leu Thr Ile Gly Pro Gly
                    500                 505                 510
Asp Phe Leu Val His His Ala Ile Ala Leu Gly Leu His Thr Thr Ala
                    515                 520                 525
Leu Ile Leu Ile Lys Gly Ala Leu Asp Ala Arg Gly Ser Lys Leu Met
                530                 535                 540
Pro Asp Lys Lys Asp Phe Gly Tyr Ser Phe Pro Cys Asp Gly Pro Gly
545                 550                 555                 560
Arg Gly Gly Thr Cys Asp Ile Ser Ala Trp Asp Ala Phe Tyr Leu Ala
                    565                 570                 575
Met Phe Trp Met Leu Asn Thr Leu Gly Trp Leu Thr Phe Tyr Trp His
                    580                 585                 590
Trp Lys His Leu Gly Val Trp Ser Gly Asn Val Ala Gln Phe Asn Glu
                    595                 600                 605
Asn Ser Thr Tyr Leu Met Gly Trp Phe Arg Asp Tyr Leu Trp Ala Asn
                610                 615                 620
Ser Ala Gln Leu Ile Asn Gly Tyr Asn Pro Tyr Gly Val Asn Asn Leu
625                 630                 635                 640
Ser Val Trp Ala Trp Met Phe Leu Phe Gly His Leu Val Trp Ala Thr
                    645                 650                 655
Gly Phe Met Phe Leu Ile Ser Trp Arg Gly Tyr Trp Gln Glu Leu Ile
                    660                 665                 670
Glu Thr Ile Val Trp Ala His Glu Arg Thr Pro Leu Ala Asn Leu Val
                    675                 680                 685
Arg Trp Lys Asp Lys Pro Val Ala Leu Ser Ile Val Gln Ala Arg Leu
                690                 695                 700
Val Gly Leu Ala His Phe Thr Val Gly Tyr Val Leu Thr Tyr Ala Ala
705                 710                 715                 720
Phe Leu Ile Ala Ser Thr Ala Gly Lys Phe Gly
                    725                 730
```

<210> SEQ ID NO 26
<211> LENGTH: 81
<212> TYPE: PRT
<213> ORGANISM: Synechocystis sp.
<220> FEATURE:
<221> NAME/KEY: misc_feature
<223> OTHER INFORMATION: W31C mutant polypeptide

<400> SEQUENCE: 26

```
Met Ser His Ser Val Lys Ile Tyr Asp Thr Cys Ile Gly Cys Thr Gln
1               5                   10                  15

Cys Val Arg Ala Cys Pro Leu Asp Val Leu Glu Met Val Pro Cys Asp
            20                  25                  30

Gly Cys Lys Ala Ala Gln Ile Ala Ser Ser Pro Arg Thr Glu Asp Cys
        35                  40                  45

Val Gly Cys Lys Arg Cys Glu Thr Ala Cys Pro Thr Asp Phe Leu Ser
    50                  55                  60

Ile Arg Val Tyr Leu Gly Ala Glu Thr Thr Arg Ser Met Gly Leu Ala
65                  70                  75                  80

Tyr
```

<210> SEQ ID NO 27
<211> LENGTH: 812
<212> TYPE: PRT
<213> ORGANISM: Synechocystis sp.
<220> FEATURE:
<221> NAME/KEY: misc_feature
<223> OTHER INFORMATION: W31C/D235C/Y634 mutant polypeptide

<400> SEQUENCE: 27

```
Met Ser His Ser Val Lys Ile Tyr Asp Thr Cys Ile Gly Cys Thr Gln
1               5                   10                  15

Cys Val Arg Ala Cys Pro Leu Asp Val Leu Glu Met Val Pro Cys Asp
            20                  25                  30

Gly Cys Lys Ala Ala Gln Ile Ala Ser Ser Pro Arg Thr Glu Asp Cys
        35                  40                  45

Val Gly Cys Lys Arg Cys Glu Thr Ala Cys Pro Thr Asp Phe Leu Ser
    50                  55                  60

Ile Arg Val Tyr Leu Gly Ala Glu Thr Thr Arg Ser Met Gly Leu Ala
65                  70                  75                  80

Tyr Met Ala Thr Lys Phe Pro Lys Phe Ser Gln Asp Leu Ala Gln Asp
            85                  90                  95

Pro Thr Thr Arg Arg Ile Trp Tyr Gly Ile Ala Thr Ala His Asp Phe
        100                 105                 110

Glu Thr His Asp Gly Met Thr Glu Glu Asn Leu Tyr Gln Lys Ile Phe
    115                 120                 125

Ala Ser His Phe Gly His Ile Ala Ile Ile Phe Leu Trp Thr Ser Gly
130                 135                 140

Thr Leu Phe His Val Ala Trp Gln Gly Asn Phe Glu Gln Trp Ile Lys
145                 150                 155                 160

Asp Pro Leu Asn Ile Arg Pro Ile Ala His Ala Ile Trp Asp Pro His
            165                 170                 175

Phe Gly Glu Gly Ala Val Asn Ala Phe Thr Gln Ala Gly Ala Ser Asn
        180                 185                 190

Pro Val Asn Ile Ala Tyr Ser Gly Val Tyr His Trp Phe Tyr Thr Ile
    195                 200                 205
```

```
Gly Met Thr Thr Asn Gln Glu Leu Tyr Ser Gly Ala Val Phe Leu Leu
    210                 215                 220

Val Leu Ala Ser Leu Phe Leu Phe Ala Gly Trp Leu His Leu Gln Pro
225                 230                 235                 240

Lys Phe Arg Pro Ser Leu Ala Trp Phe Lys Asn Ala Glu Ser Arg Leu
                245                 250                 255

Asn His His Leu Ala Gly Leu Phe Gly Val Ser Ser Leu Ala Trp Ala
                260                 265                 270

Gly His Leu Val His Val Ala Ile Pro Glu Ala Arg Gly Gln His Val
                275                 280                 285

Gly Trp Asp Asn Phe Leu Ser Thr Pro Pro His Pro Ala Gly Leu Met
    290                 295                 300

Pro Phe Phe Thr Gly Asn Trp Gly Val Tyr Ala Ala Cys Pro Asp Thr
305                 310                 315                 320

Ala Gly His Ile Phe Gly Thr Ser Glu Gly Ala Gly Thr Ala Ile Leu
                325                 330                 335

Thr Phe Leu Gly Gly Phe His Pro Gln Thr Glu Ser Leu Trp Leu Thr
                340                 345                 350

Asp Ile Ala His His His Leu Ala Ile Ala Val Ile Phe Ile Ile Ala
                355                 360                 365

Gly His Met Tyr Arg Thr Asn Trp Gly Ile Gly His Ser Ile Lys Glu
    370                 375                 380

Ile Leu Asn Ala His Lys Gly Pro Leu Thr Gly Ala Gly His Thr Asn
385                 390                 395                 400

Leu Tyr Asp Thr Ile Asn Asn Ser Leu His Phe Gln Leu Gly Leu Ala
                405                 410                 415

Leu Ala Ser Leu Gly Val Ile Thr Ser Leu Val Ala Gln His Met Tyr
                420                 425                 430

Ser Leu Pro Ser Tyr Ala Phe Ile Ala Gln Asp His Thr Thr Gln Ala
                435                 440                 445

Ala Leu Tyr Thr His His Gln Tyr Ile Ala Gly Phe Leu Met Val Gly
    450                 455                 460

Ala Phe Ala His Gly Ala Ile Phe Phe Val Arg Asp Tyr Asp Pro Val
465                 470                 475                 480

Ala Asn Lys Asp Asn Val Leu Ala Arg Met Leu Glu His Lys Glu Ala
                485                 490                 495

Leu Ile Ser His Leu Ser Trp Val Ser Leu Phe Leu Gly Phe His Thr
                500                 505                 510

Leu Gly Leu Tyr Val His Asn Asp Val Val Val Ala Phe Gly Thr Pro
    515                 520                 525

Glu Lys Gln Ile Leu Ile Glu Pro Val Phe Ala Gln Trp Ile Gln Ala
    530                 535                 540

Thr Ser Gly Lys Ala Leu Tyr Gly Phe Asp Val Leu Leu Ser Asn Pro
545                 550                 555                 560

Asp Ser Ile Ala Ser Thr Thr Gly Ala Ala Trp Leu Pro Gly Trp Leu
                565                 570                 575

Asp Ala Ile Asn Ser Gly Thr Asn Ser Leu Phe Leu Thr Ile Gly Pro
                580                 585                 590

Gly Asp Phe Leu Val His His Ala Ile Ala Leu Gly Leu His Thr Thr
                595                 600                 605

Ala Leu Ile Leu Ile Lys Gly Ala Leu Asp Ala Arg Gly Ser Lys Leu
    610                 615                 620

Met Pro Asp Lys Lys Asp Phe Gly Tyr Ser Phe Pro Cys Asp Gly Pro
```

-continued

```
                625                 630                 635                 640
Gly Arg Gly Gly Thr Cys Asp Ile Ser Ala Trp Asp Ala Phe Tyr Leu
                    645                 650                 655

Ala Met Phe Trp Met Leu Asn Thr Leu Gly Trp Leu Thr Phe Tyr Trp
                    660                 665                 670

His Trp Lys His Leu Gly Val Trp Ser Gly Asn Val Ala Gln Phe Asn
                    675                 680                 685

Glu Asn Ser Thr Tyr Leu Met Gly Trp Phe Arg Asp Tyr Leu Trp Ala
                    690                 695                 700

Asn Ser Ala Gln Leu Ile Asn Gly Tyr Asn Pro Cys Gly Val Asn Asn
705                 710                 715                 720

Leu Ser Val Trp Ala Trp Met Phe Leu Phe Gly His Leu Val Trp Ala
                    725                 730                 735

Thr Gly Phe Met Phe Leu Ile Ser Trp Arg Gly Tyr Trp Gln Glu Leu
                    740                 745                 750

Ile Glu Thr Ile Val Trp Ala His Glu Arg Thr Pro Leu Ala Asn Leu
                    755                 760                 765

Val Arg Trp Lys Asp Lys Pro Val Ala Leu Ser Ile Val Gln Ala Arg
                    770                 775                 780

Leu Val Gly Leu Ala His Phe Thr Val Gly Tyr Val Leu Thr Tyr Ala
785                 790                 795                 800

Ala Phe Leu Ile Ala Ser Thr Ala Gly Lys Phe Gly
                    805                 810

<210> SEQ ID NO 28
<211> LENGTH: 731
<212> TYPE: PRT
<213> ORGANISM: Synechocystis sp.
<220> FEATURE:
<221> NAME/KEY: misc_feature
<223> OTHER INFORMATION: D235C/Y634 mutant polypeptide

<400> SEQUENCE: 28

Met Ala Thr Lys Phe Pro Lys Phe Ser Gln Asp Leu Ala Gln Asp Pro
1               5                   10                  15

Thr Thr Arg Arg Ile Trp Tyr Gly Ile Ala Thr Ala His Asp Phe Glu
                20                  25                  30

Thr His Asp Gly Met Thr Glu Glu Asn Leu Tyr Gln Lys Ile Phe Ala
            35                  40                  45

Ser His Phe Gly His Ile Ala Ile Ile Phe Leu Trp Thr Ser Gly Thr
        50                  55                  60

Leu Phe His Val Ala Trp Gln Gly Asn Phe Glu Gln Trp Ile Lys Asp
65                  70                  75                  80

Pro Leu Asn Ile Arg Pro Ile Ala His Ala Ile Trp Asp Pro His Phe
                85                  90                  95

Gly Glu Gly Ala Val Asn Ala Phe Thr Gln Ala Gly Ala Ser Asn Pro
            100                 105                 110

Val Asn Ile Ala Tyr Ser Gly Val Tyr His Trp Phe Tyr Thr Ile Gly
        115                 120                 125

Met Thr Thr Asn Gln Glu Leu Tyr Ser Gly Ala Val Phe Leu Leu Val
    130                 135                 140

Leu Ala Ser Leu Phe Leu Phe Ala Gly Trp Leu His Leu Gln Pro Lys
145                 150                 155                 160

Phe Arg Pro Ser Leu Ala Trp Phe Lys Asn Ala Glu Ser Arg Leu Asn
                165                 170                 175
```

```
His His Leu Ala Gly Leu Phe Gly Val Ser Ser Leu Ala Trp Ala Gly
            180                 185                 190

His Leu Val His Val Ala Ile Pro Glu Ala Arg Gly Gln His Val Gly
        195                 200                 205

Trp Asp Asn Phe Leu Ser Thr Pro Pro His Pro Ala Gly Leu Met Pro
    210                 215                 220

Phe Phe Thr Gly Asn Trp Gly Val Tyr Ala Ala Cys Pro Asp Thr Ala
225                 230                 235                 240

Gly His Ile Phe Gly Thr Ser Glu Gly Ala Gly Thr Ala Ile Leu Thr
                245                 250                 255

Phe Leu Gly Gly Phe His Pro Gln Thr Glu Ser Leu Trp Leu Thr Asp
            260                 265                 270

Ile Ala His His His Leu Ala Ile Ala Val Ile Phe Ile Ile Ala Gly
        275                 280                 285

His Met Tyr Arg Thr Asn Trp Gly Ile Gly His Ser Ile Lys Glu Ile
    290                 295                 300

Leu Asn Ala His Lys Gly Pro Leu Thr Gly Ala Gly His Thr Asn Leu
305                 310                 315                 320

Tyr Asp Thr Ile Asn Asn Ser Leu His Phe Gln Leu Gly Leu Ala Leu
                325                 330                 335

Ala Ser Leu Gly Val Ile Thr Ser Leu Val Ala Gln His Met Tyr Ser
            340                 345                 350

Leu Pro Ser Tyr Ala Phe Ile Ala Gln Asp His Thr Thr Gln Ala Ala
        355                 360                 365

Leu Tyr Thr His His Gln Tyr Ile Ala Gly Phe Leu Met Val Gly Ala
    370                 375                 380

Phe Ala His Gly Ala Ile Phe Phe Val Arg Asp Tyr Asp Pro Val Ala
385                 390                 395                 400

Asn Lys Asp Asn Val Leu Ala Arg Met Leu Glu His Lys Glu Ala Leu
                405                 410                 415

Ile Ser His Leu Ser Trp Val Ser Leu Phe Leu Gly Phe His Thr Leu
            420                 425                 430

Gly Leu Tyr Val His Asn Asp Val Val Val Ala Phe Gly Thr Pro Glu
        435                 440                 445

Lys Gln Ile Leu Ile Glu Pro Val Phe Ala Gln Trp Ile Gln Ala Thr
    450                 455                 460

Ser Gly Lys Ala Leu Tyr Gly Phe Asp Val Leu Leu Ser Asn Pro Asp
465                 470                 475                 480

Ser Ile Ala Ser Thr Thr Gly Ala Ala Trp Leu Pro Gly Trp Leu Asp
                485                 490                 495

Ala Ile Asn Ser Gly Thr Asn Ser Leu Phe Leu Thr Ile Gly Pro Gly
            500                 505                 510

Asp Phe Leu Val His His Ala Ile Ala Leu Gly Leu His Thr Thr Ala
        515                 520                 525

Leu Ile Leu Ile Lys Gly Ala Leu Asp Ala Arg Gly Ser Lys Leu Met
    530                 535                 540

Pro Asp Lys Lys Asp Phe Gly Tyr Ser Phe Pro Cys Asp Gly Pro Gly
545                 550                 555                 560

Arg Gly Gly Thr Cys Asp Ile Ser Ala Trp Asp Ala Phe Tyr Leu Ala
                565                 570                 575

Met Phe Trp Met Leu Asn Thr Leu Gly Trp Leu Thr Phe Tyr Trp His
            580                 585                 590

Trp Lys His Leu Gly Val Trp Ser Gly Asn Val Ala Gln Phe Asn Glu
```

-continued

```
            595                 600                 605
Asn Ser Thr Tyr Leu Met Gly Trp Phe Arg Asp Tyr Leu Trp Ala Asn
        610                 615                 620

Ser Ala Gln Leu Ile Asn Gly Tyr Asn Pro Cys Gly Val Asn Asn Leu
625                 630                 635                 640

Ser Val Trp Ala Trp Met Phe Leu Phe Gly His Leu Val Trp Ala Thr
                645                 650                 655

Gly Phe Met Phe Leu Ile Ser Trp Arg Gly Tyr Trp Gln Glu Leu Ile
            660                 665                 670

Glu Thr Ile Val Trp Ala His Glu Arg Thr Pro Leu Ala Asn Leu Val
        675                 680                 685

Arg Trp Lys Asp Lys Pro Val Ala Leu Ser Ile Val Gln Ala Arg Leu
690                 695                 700

Val Gly Leu Ala His Phe Thr Val Gly Tyr Val Leu Thr Tyr Ala Ala
705                 710                 715                 720

Phe Leu Ile Ala Ser Thr Ala Gly Lys Phe Gly
                725                 730
```

<210> SEQ ID NO 29
<211> LENGTH: 731
<212> TYPE: PRT
<213> ORGANISM: Synechocystis sp.
<220> FEATURE:
<221> NAME/KEY: misc_feature
<223> OTHER INFORMATION: S246C/Y634C mutant polypeptide

<400> SEQUENCE: 29

```
Met Ala Thr Lys Phe Pro Lys Phe Ser Gln Asp Leu Ala Gln Asp Pro
1               5                   10                  15

Thr Thr Arg Arg Ile Trp Tyr Gly Ile Ala Thr Ala His Asp Phe Glu
            20                  25                  30

Thr His Asp Gly Met Thr Glu Glu Asn Leu Tyr Gln Lys Ile Phe Ala
        35                  40                  45

Ser His Phe Gly His Ile Ala Ile Ile Phe Leu Trp Thr Ser Gly Thr
    50                  55                  60

Leu Phe His Val Ala Trp Gln Gly Asn Phe Glu Gln Trp Ile Lys Asp
65                  70                  75                  80

Pro Leu Asn Ile Arg Pro Ile Ala His Ala Ile Trp Asp Pro His Phe
                85                  90                  95

Gly Glu Gly Ala Val Asn Ala Phe Thr Gln Ala Gly Ala Ser Asn Pro
            100                 105                 110

Val Asn Ile Ala Tyr Ser Gly Val Tyr His Trp Phe Tyr Thr Ile Gly
        115                 120                 125

Met Thr Thr Asn Gln Glu Leu Tyr Ser Gly Ala Val Phe Leu Leu Val
    130                 135                 140

Leu Ala Ser Leu Phe Leu Phe Ala Gly Trp Leu His Leu Gln Pro Lys
145                 150                 155                 160

Phe Arg Pro Ser Leu Ala Trp Phe Lys Asn Ala Glu Ser Arg Leu Asn
                165                 170                 175

His His Leu Ala Gly Leu Phe Gly Val Ser Ser Leu Ala Trp Ala Gly
            180                 185                 190

His Leu Val His Val Ala Ile Pro Glu Ala Arg Gly Gln His Val Gly
        195                 200                 205

Trp Asp Asn Phe Leu Ser Thr Pro Pro His Pro Ala Gly Leu Met Pro
    210                 215                 220
```

-continued

```
Phe Phe Thr Gly Asn Trp Gly Val Tyr Ala Ala Asp Pro Asp Thr Ala
225                 230                 235                 240

Gly His Ile Phe Gly Thr Cys Glu Gly Ala Gly Thr Ala Ile Leu Thr
            245                 250                 255

Phe Leu Gly Gly Phe His Pro Gln Thr Glu Ser Leu Trp Leu Thr Asp
                260                 265                 270

Ile Ala His His His Leu Ala Ile Ala Val Ile Phe Ile Ile Ala Gly
        275                 280                 285

His Met Tyr Arg Thr Asn Trp Gly Ile Gly His Ser Ile Lys Glu Ile
    290                 295                 300

Leu Asn Ala His Lys Gly Pro Leu Thr Gly Ala Gly His Thr Asn Leu
305                 310                 315                 320

Tyr Asp Thr Ile Asn Asn Ser Leu His Phe Gln Leu Gly Leu Ala Leu
                325                 330                 335

Ala Ser Leu Gly Val Ile Thr Ser Leu Val Ala Gln His Met Tyr Ser
            340                 345                 350

Leu Pro Ser Tyr Ala Phe Ile Ala Gln Asp His Thr Thr Gln Ala Ala
        355                 360                 365

Leu Tyr Thr His His Gln Tyr Ile Ala Gly Phe Leu Met Val Gly Ala
    370                 375                 380

Phe Ala His Gly Ala Ile Phe Phe Val Arg Asp Tyr Asp Pro Val Ala
385                 390                 395                 400

Asn Lys Asp Asn Val Leu Ala Arg Met Leu Glu His Lys Glu Ala Leu
                405                 410                 415

Ile Ser His Leu Ser Trp Val Ser Leu Phe Leu Gly Phe His Thr Leu
            420                 425                 430

Gly Leu Tyr Val His Asn Asp Val Val Ala Phe Gly Thr Pro Glu
        435                 440                 445

Lys Gln Ile Leu Ile Glu Pro Val Phe Ala Gln Trp Ile Gln Ala Thr
    450                 455                 460

Ser Gly Lys Ala Leu Tyr Gly Phe Asp Val Leu Leu Ser Asn Pro Asp
465                 470                 475                 480

Ser Ile Ala Ser Thr Thr Gly Ala Ala Trp Leu Pro Gly Trp Leu Asp
                485                 490                 495

Ala Ile Asn Ser Gly Thr Asn Ser Leu Phe Leu Thr Ile Gly Pro Gly
            500                 505                 510

Asp Phe Leu Val His His Ala Ile Ala Leu Gly Leu His Thr Thr Ala
        515                 520                 525

Leu Ile Leu Ile Lys Gly Ala Leu Asp Ala Arg Gly Ser Lys Leu Met
    530                 535                 540

Pro Asp Lys Lys Asp Phe Gly Tyr Ser Phe Pro Cys Asp Gly Pro Gly
545                 550                 555                 560

Arg Gly Gly Thr Cys Asp Ile Ser Ala Trp Asp Ala Phe Tyr Leu Ala
                565                 570                 575

Met Phe Trp Met Leu Asn Thr Leu Gly Trp Leu Thr Phe Tyr Trp His
            580                 585                 590

Trp Lys His Leu Gly Val Trp Ser Gly Asn Val Ala Gln Phe Asn Glu
    595                 600                 605

Asn Ser Thr Tyr Leu Met Gly Trp Phe Arg Asp Tyr Leu Trp Ala Asn
            610                 615                 620

Ser Ala Gln Leu Ile Asn Gly Tyr Asn Pro Cys Gly Val Asn Asn Leu
625                 630                 635                 640

Ser Val Trp Ala Trp Met Phe Leu Phe Gly His Leu Val Trp Ala Thr
```

-continued

```
                645                 650                 655
Gly Phe Met Phe Leu Ile Ser Trp Arg Gly Tyr Trp Gln Glu Leu Ile
            660                 665                 670

Glu Thr Ile Val Trp Ala His Glu Arg Thr Pro Leu Ala Asn Leu Val
        675                 680                 685

Arg Trp Lys Asp Lys Pro Val Ala Leu Ser Ile Val Gln Ala Arg Leu
    690                 695                 700

Val Gly Leu Ala His Phe Thr Val Gly Tyr Val Leu Thr Tyr Ala Ala
705                 710                 715                 720

Phe Leu Ile Ala Ser Thr Ala Gly Lys Phe Gly
                725                 730
```

<210> SEQ ID NO 30
<211> LENGTH: 2196
<212> TYPE: DNA
<213> ORGANISM: Synechocystis sp.
<220> FEATURE:
<221> NAME/KEY: misc_feature
<223> OTHER INFORMATION: D479C mutant polynucleotide

<400> SEQUENCE: 30

| | | | | |
|---|---|---|---|---|
| atggcaacta | aatttcctaa | atttagccag | gatctcgccc | aagacccgac tacacggcgt | 60 |
| atttggtacg | ggattgctac | ggcccacgac | tttgaaaccc | acgatgggat gactgaggag | 120 |
| aatctttacc | aaaagatttt | tgcctcccac | tttggacaca | tcgccatcat tttcctgtgg | 180 |
| acgtctggca | ccctttttcca | cgttgcgtgg | caaggtaatt | ttgaacaatg gattaaagat | 240 |
| cctttaaaca | ttcgcccgat | cgcccatgcg | atttgggacc | cccactttgg cgagggagct | 300 |
| gtcaatgctt | tcacccaagc | tggggcttct | aacccggtta | acattgctta ttccggggtt | 360 |
| taccactggt | tctacaccat | tggtatgacc | accaaccaag | agctctattc tggtgcggtc | 420 |
| ttcctattag | tgttagcttc | cctgttttta | tttgcaggct | ggttacacct caaccgaag | 480 |
| ttccgtccta | gcttagcctg | gttcaaaaat | gccgaatccc | gcttaaatca ccacctggct | 540 |
| ggtttgttcg | gggttagctc | cttggcttgg | gctggtcact | tggtccacgt tgcgattccc | 600 |
| gaagcccggg | gtcaacacgt | tggttgggat | aacttcctgt | ctactcctcc caccccgct | 660 |
| ggtttgatgc | ctttcttcac | cggcaactgg | ggcgtgtatg | cggcggatcc cgacactgct | 720 |
| ggccacattt | ttggtacttc | tgaaggtgct | ggtaccgcaa | tcctgacctt cctgggtggt | 780 |
| ttccatcccc | aaacggaatc | tctctggttg | acggacattg | cccaccacca tttggcgatc | 840 |
| gccgtgatct | tcatcattgc | tggtcacatg | tatcgcacca | actggggcat ggccacagc | 900 |
| atcaaagaaa | ttcttaatgc | ccataaaggt | cccctaaccg | gcgcaggcca taccaacctg | 960 |
| tacgacacca | tcaataactc | cctccacttc | caactcggct | tagccttggc aagcttaggg | 1020 |
| gttattactt | ccctggtggc | gcagcacatg | tactccctgc | cctcctacgc ctttattgcc | 1080 |
| caggaccaca | ccacccaggc | agccctctac | acccatcacc | agtacattgc tggattcttg | 1140 |
| atggttggtg | cttttgccca | cggtgccatc | ttctttgtcc | gggattacga tcccgtggcc | 1200 |
| aataaagata | acgtgctggc | ccgcatgctt | gaacacaaag | aggctctgat tcccacttta | 1260 |
| agctgggtgt | ccctcttctt | gggcttccac | accttggtc | tttatgtcca taacgatgtg | 1320 |
| gtggtggcct | tcggtactcc | cgaaaaacaa | attctgatcg | agcccgtttt tgcccaatgg | 1380 |
| attcaagcaa | cttccggtaa | agctctctat | ggctttgatg | ttttgctctc caatccttgc | 1440 |
| agcattgctt | ccaccactgg | agccgcttgg | ttacccggct | ggttggatgc tatcaacagc | 1500 |
| ggcaccaact | ctctgttctt | gaccattggc | cctggcgact | tcttggttca ccacgcgatc | 1560 |

```
gccctagggt tgcacaccac tgccctgatt ctaatcaaag gtgctttgga tgcccgtggt      1620
tctaagttga tgccggacaa aaaggacttc ggttactcct tccctgtga tggccccggc       1680 cgtggcggta cctgcgacat ctctgcttgg gatgccttct acctagccat gttctggatg      1740
ctgaacacct tgggttggtt gaccttctac tggcactgga acacctcgg tgtttggagc       1800 ggtaacgttg ctcagttcaa cgaaaactcc acctacctga tgggttggtt ccgggattac      1860
ctctgggcga actctgctca gttaatcaat ggttacaacc cctacggtgt caacaatctg      1920
tcagtttggg cttggatgtt ccttttcgga cacctggtct gggctactgg cttcatgttc      1980
ttgatctctt ggcggggtta ctggcaagag ttgattgaaa ccatcgtttg ggcccacgag      2040
cgcactcctt tggcgaactt ggttcgttgg aaagataagc ccgttgcgtt gtccattgtt      2100
caagcccgtt tggttggttt agcccacttc accgttggtt atgtgctcac ctatgcggca      2160
ttcctaattg cttccacagc cggtaagttc ggttaa                                2196

<210> SEQ ID NO 31
<211> LENGTH: 2196
<212> TYPE: DNA
<213> ORGANISM: Synechocystis sp.
<220> FEATURE:
<221> NAME/KEY: misc_feature
<223> OTHER INFORMATION: S499C mutant polynucleotide

<400> SEQUENCE: 31
atggcaacta aatttcctaa atttagccag gatctcgccc aagacccgac tacacggcgt        60
atttggtacg ggattgctac ggcccacgac tttgaaaccc acgatgggat gactgaggag       120
aatctttacc aaaagatttt tgcctcccac tttggacaca tcgccatcat tttcctgtgg       180
acgtctggca cccttttcca cgttgcgtgg caaggtaatt ttgaacaatg gattaaagat       240
cctttaaaca ttcgcccgat cgcccatgcg atttgggacc cccactttgg cgagggagct       300
gtcaatgctt tcacccaagc tggggcttct aacccggtta acattgctta ttccggggtt       360
taccactggt tctacaccat tggtatgacc accaaccaag agctctattc tggtgcggtc       420
ttcctattag tgttagcttc cctgttttta tttgcaggct ggttacacct ccaaccgaag       480
ttccgtccta gcttagcctg gttcaaaaat gccgaatccc gcttaaatca ccacctggct       540
ggtttgttcg gggttagctc cttggcttgg gctggtcact tggtccacgt tgcgattccc       600
gaagcccggg gtcaacacgt tggttgggat aacttcctgt ctactcctcc ccaccccgct       660
ggtttgatgc ctttcttcac cggcaactgg ggcgtgtatg cggcggatcc cgacactgct       720
ggccacattt tggtacttc tgaaggtgct ggtaccgcaa tcctgacctt cctgggtggt       780
ttccatcccc aaacggaatc tctctggttg acggacattg cccaccacca tttggcgatc       840
gccgtgatct tcatcattgc tggtcacatg tatcgcacca actggggcat tggccacagc       900
atcaaagaaa ttcttaatgc ccataaaggt cccctaaccg gcgcaggcca taccaacctg       960
tacgacacca tcaataactc cctccacttc caactcggct tagccttggc aagcttaggg      1020
gttattactt ccctggtggc gcagcacatg tactccctgc cctcctacgc ctttattgcc      1080
caggaccaca ccacccaggc agccctctac accatcacc agtacattgc tggattcttg       1140
atggttggtg cttttgccca cggtgccatc ttctttgtcc gggattacga tcccgtggcc      1200
aataaagata acgtgctggc ccgcatgctt gaacacaaag aggctctgat ttcccactta      1260
agctgggtgt ccctcttctt gggcttccac accttggtc tttatgtcca taacgatgtg       1320
gtggtggcct tcggtactcc cgaaaaacaa attctgatcg agcccgtttt tgcccaatgg      1380
```

-continued

```
attcaagcaa cttccggtaa agctctctat ggctttgatg ttttgctctc caatcctgac    1440
agcattgctt ccaccactgg agccgcttgg ttacccggct ggttggatgc tatcaactgc    1500
ggcaccaact ctctgttctt gaccattggc cctggcgact tcttggttca ccacgcgatc    1560
gccctagggt tgcacaccac tgccctgatt ctaatcaaag gtgctttgga tgcccgtggt    1620
tctaagttga tgccggacaa aaaggacttc ggttactcct tccctgtga tggcccggc     1680 cgtggcggta cctgcgacat ctctgcttgg gatgccttct acctagccat gttctggatg    1740
ctgaacacct tgggttggtt gaccttctac tggcactgga acacctcgg tgtttggagc     1800 ggtaacgttg ctcagttcaa cgaaaactcc acctacctga tgggttggtt ccgggattac    1860
ctctgggcga actctgctca gttaatcaat ggttacaacc cctacggtgt caacaatctg    1920
tcagtttggg cttggatgtt cctttttcgga cacctggtct gggctactgg cttcatgttc    1980
ttgatctctt ggcggggtta ctggcaagag ttgattgaaa ccatcgtttg ggcccacgag    2040
cgcactcctt tggcgaactt ggttcgttgg aaagataagc ccgttgcgtt gtccattgtt    2100
caagcccgtt tggttggttt agcccacttc accgttggtt atgtgctcac ctatgcggca    2160
ttcctaattg cttccacagc cggtaagttc ggttaa                              2196
```

<210> SEQ ID NO 32
<211> LENGTH: 2196
<212> TYPE: DNA
<213> ORGANISM: Synechocystis sp.
<220> FEATURE:
<221> NAME/KEY: misc_feature
<223> OTHER INFORMATION: S599C mutant polynucleotide

<400> SEQUENCE: 32

```
atggcaacta aatttcctaa atttagccag gatctcgccc aagacccgac tacacggcgt     60
atttggtacg ggattgctac ggcccacgac tttgaaaccc acgatgggat gactgaggag    120
aatctttacc aaaagatttt tgcctcccac tttggacaca tcgccatcat tttcctgtgg    180
acgtctggca cccttttcca cgttgcgtgg caaggtaatt ttgaacaatg gattaaagat    240
cctttaaaca ttcgcccgat cgcccatgcg atttgggacc ccacttggg cgagggagct    300 gtcaatgctt tcacccaagc tggggcttct aacccggtta acattgctta ttccgggggtt    360 taccactggt tctacaccat tggtatgacc accaaccaag agctctattc tggtgcggtc    420
ttcctattag tgttagcttc cctgttttta tttgcaggct ggttacacct ccaaccgaag    480
ttccgtccta gctagcctg gttcaaaaat gccgaatccc gcttaaatca ccacctggct    540
ggtttgttcg gggttagctc cttggcttgg gctggtcact tggtccacgt tgcgattccc    600
gaagcccggg tcaacacgt tggttgggat aacttcctgt ctactcctcc ccaccccgct     660
ggtttgatgc ctttcttcac cggcaactgg ggcgtgtatg cggcggatcc cgacactgct    720
ggccacattt ttggtacttc tgaaggtgct ggtaccgcaa tcctgacctt cctgggtggt    780
ttccatcccc aaacggaatc tctctggttg acggacattg cccaccacca tttggcgatc    840
gccgtgatct tcatcattgc tggtcacatg tatcgcacca actggggcat ggccacagc    900 atcaaagaaa ttcttaatgc ccataaaggt cccctaaccg gcgcaggcca taccaacctg    960
tacgacacca tcaataactc cctccacttc caactcggct tagccttggc aagcttaggg    1020
gttattactt ccctggtggc gcagcacatg tactccctgc cctcctacgc ctttattgcc    1080
caggaccaca ccacccaggc agccctctac acccatcacc agtacattgc tggattcttg    1140
atggttggtg cttttgccca cggtgccatc ttctttgtcc gggattacga tcccgtggcc    1200
```

-continued

```
aataaagata acgtgctggc ccgcatgctt gaacacaaag aggctctgat ttcccactta   1260
agctgggtgt ccctcttctt gggcttccac acccttggtc tttatgtcca taacgatgtg   1320
gtggtggcct tcggtactcc cgaaaaacaa attctgatcg agcccgtttt tgcccaatgg   1380
attcaagcaa cttccggtaa agctctctat ggctttgatg ttttgctctc caatcctgac   1440
agcattgctt ccaccactgg agccgcttgg ttacccggct ggttggatgc tatcaacagc   1500
ggcaccaact ctctgttctt gaccattggc cctggcgact tcttggttca ccacgcgatc   1560
gccctagggt tgcacaccac tgccctgatt ctaatcaaag gtgctttgga tgcccgtggt   1620
tctaagttga tgccggacaa aaaggacttc ggttactcct tcccctgtga tggccccggc   1680
cgtggcggta cctgcgacat ctctgcttgg gatgccttct acctagccat gttctggatg   1740
ctgaacacct tgggttggtt gaccttctac tggcactgga aacacctcgg tgtttggtgc   1800
ggtaacgttg ctcagttcaa cgaaaactcc acctacctga tgggttggtt ccgggattac   1860
ctctgggcga actctgctca gttaatcaat ggttacaacc cctacggtgt caacaatctg   1920
tcagtttggg cttggatgtt cctttttcgga cacctggtct gggctactgg cttcatgttc   1980
ttgatctctt ggcggggtta ctggcaagag ttgattgaaa ccatcgtttg ggcccacgag   2040
cgcactcctt tggcgaactt ggttcgttgg aaagataagc ccgttgcgtt gtccattgtt   2100
caagcccgtt tggttggttt agcccacttc accgttggtt atgtgctcac ctatgcggca   2160
ttcctaattg cttccacagc cggtaagttc ggttaa                             2196
```

<210> SEQ ID NO 33
<211> LENGTH: 2196
<212> TYPE: DNA
<213> ORGANISM: Synechocystis sp.
<220> FEATURE:
<221> NAME/KEY: misc_feature
<223> OTHER INFORMATION: Y634C mutant polynucleotide

<400> SEQUENCE: 33

```
atggcaacta aatttcctaa atttagccag gatctcgccc aagacccgac tacacggcgt     60
atttggtacg ggattgctac ggcccacgac tttgaaaccc acgatgggat gactgaggag    120
aatctttacc aaaagatttt tgcctcccac tttggacaca tcgccatcat tttcctgtgg    180
acgtctggca cccttttcca cgttgcgtgg caaggtaatt ttgaacaatg gattaaagat    240
cctttaaaca ttcgcccgat cgcccatgcg atttgggacc cccactttgg cgagggagct    300
gtcaatgctt tcacccaagc tggggcttct aacccggtta acattgctta ttccggggtt    360
taccactggt tctacaccat ggtatgacc accaaccaag agctctattc tggtgcggtc    420
ttcctattag tgttagcttc cctgttttta tttgcaggct ggttacacct caaccgaag    480 ttccgtccta gcttagcctg gttcaaaaat gccgaatccc gcttaaatca ccacctggct    540
ggtttgttcg gggttagctc cttggcttgg gctggtcact tggtccacgt tgcgattccc    600
gaagcccggg gtcaacacgt tggttgggat aacttcctgt ctactcctcc caccccgct   660 ggtttgatgc ctttcttcac cggcaactgg ggcgtgtatg cggcggatcc cgacactgct    720
ggccacattt ttggtacttc tgaaggtgct ggtaccgcaa tcctgacctt cctgggtggt    780
ttccatcccc aaacggaatc tctctggttg acggacattg cccaccacca tttggcgatc    840
gccgtgatct tcatcattgc tggtcacatg tatcgcacca ctgggcat tggccacagc    900 atcaaagaaa tcttaatgc ccataaaggt cccctaaccg cgcaggcca taccaacctg    960 tacgacacca tcaataactc cctccacttc caactcggct tagccttggc aagcttaggg   1020
```

```
gttattactt ccctggtggc gcagcacatg tactccctgc cctcctacgc ctttattgcc    1080
caggaccaca ccacccaggc agccctctac acccatcacc agtacattgc tggattcttg    1140
atggttggtg cttttgccca cggtgccatc ttctttgtcc gggattacga tcccgtggcc    1200
aataaagata acgtgctggc ccgcatgctt gaacacaaag aggctctgat tcccacttta    1260
agctgggtgt ccctcttctt gggcttccac acccttggtc tttatgtcca taacgatgtg    1320
gtggtggcct tcggtactcc cgaaaaacaa attctgatcg agcccgtttt tgcccaatgg    1380
attcaagcaa cttccggtaa agctctctat ggctttgatg ttttgctctc caatcctgac    1440
agcattgctt ccaccactgg agccgcttgg ttacccggct ggttggatgc tatcaacagc    1500
ggcaccaact ctctgttctt gaccattggc cctggcgact tcttggttca ccacgcgatc    1560
gccctagggt tgcacaccac tgccctgatt ctaatcaaag gtgctttgga tgcccgtggt    1620
tctaagttga tgccggacaa aaaggacttc ggttactcct tccccgtgtga tggcccccggc   1680 cgtggcggta cctgcgacat ctctgcttgg gatgccttct acctagccat gttctggatg    1740
ctgaacacct tgggttggtt gaccttctac tggcactgga acacctcgg tgtttggagc    1800 ggtaacgttg ctcagttcaa cgaaaactcc acctacctga tgggttggtt ccgggattac    1860
ctctgggcga actctgctca gttaatcaat ggttacaacc cctgcggtgt caacaatctg    1920
tcagtttggg cttggatgtt cctttttcgga cacctggtct gggctactgg cttcatgttc    1980
ttgatctctt ggcggggtta ctggcaagag ttgattgaaa ccatcgtttg ggcccacgag    2040
cgcactcctt tggcgaactt ggttcgttgg aaagataagc ccgttgcgtt gtccattgtt    2100
caagcccgtt tggttggttt agcccacttc accgttggtt atgtgctcac ctatgcggca    2160
ttcctaattg cttccacagc cggtaagttc ggttaa                              2196
```

<210> SEQ ID NO 34
<211> LENGTH: 2196
<212> TYPE: DNA
<213> ORGANISM: Synechocystis sp.
<220> FEATURE:
<221> NAME/KEY: misc_feature
<223> OTHER INFORMATION: D235C mutant polynucleotide

<400> SEQUENCE: 34

```
atggcaacta aatttcctaa atttagccag gatctcgccc aagacccgac tacacggcgt      60
atttggtacg ggattgctac ggcccacgac tttgaaaccc acgatgggat gactgaggag     120
aatctttacc aaaagatttt tgcctcccac tttggacaca tcgccatcat tttcctgtgg     180
acgtctggca ccctttttcca cgttgcgtgg caaggtaatt tgaacaatg gattaaagat     240 cctttaaaca ttcgcccgat cgcccatgcg atttgggacc ccactttggg cgagggagct    300
gtcaatgctt tcacccaagc tggggcttct aacccggtta acattgctta ttccggggtt     360
taccactggt tctacaccat ggtatgacc accaaccaag agctctattc tggtgcggtc     420
ttcctattag tgttagcttc cctgttttta tttgcaggct ggttacacct ccaaccgaag     480
ttccgtccta gctagcctg gttcaaaaat gccgaatccc gcttaaatca ccacctggct     540
ggtttgttcg gggttagctc cttggcttgg gctggtcact tggtccacgt tgcgattccc     600
gaagcccggt gtcaacacgt tggttggat aacttcctgt ctactcctcc cacccccgct     660
ggtttgatgc cttccttcac cggcaactgg ggcgtgtatg cggcgtgtcc gacactgct     720 ggccacatt tttggtacttc tgaaggtgct ggtaccgcaa tcctgacctt cctgggtggt    780
ttccatcccc aaacggaatc tctctggttg acggacattg cccaccacca tttggcgatc   840
```

```
gccgtgatct tcatcattgc tggtcacatg tatcgcacca actggggcat tggccacagc      900
atcaaagaaa ttcttaatgc ccataaaggt ccccctaaccg gcgcaggcca taccaacctg     960
tacgacacca tcaataactc cctccacttc caactcggct tagccttggc aagcttaggg     1020
gttattactt ccctggtggc gcagcacatg tactccctgc cctcctacgc ctttattgcc     1080
caggaccaca ccacccaggc agccctctac acccatcacc agtacattgc tggattcttg     1140
atggttggtg cttttgccca cggtgccatc ttctttgtcc gggattacga tcccgtggcc     1200
aataaagata acgtgctggc ccgcatgctt gaacacaaag aggctctgat ttcccactta     1260
agctgggtgt ccctcttctt gggcttccac acccttggtc tttatgtcca taacgatgtg     1320
gtggtggcct tcggtactcc cgaaaaacaa attctgatcg agcccgtttt tgcccaatgg     1380
attcaagcaa cttccggtaa agctctctat ggctttgatg ttttgctctc caatcctgac     1440
agcattgctt ccaccactgg agccgcttgg ttacccggct ggttggatgc tatcaacagc     1500
ggcaccaact ctctgttctt gaccattggc cctggcgact tcttggttca ccacgcgatc     1560
gccctagggt tgcacaccac tgccctgatt ctaatcaaag gtgctttgga tgcccgtggt     1620
tctaagttga tgccggacaa aaaggacttc ggttactcct tcccctgtga tggccccggc     1680
cgtggcggta cctgcgacat ctctgcttgg gatgccttct acctagccat gttctggatg     1740
ctgaacacct tgggttggtt gaccttctac tggcactgga acacctcgg tgtttggagc      1800 ggtaacgttg ctcagttcaa cgaaaactcc acctacctga tgggttggtt ccgggattac     1860
ctctgggcga actctgctca gttaatcaat ggttacaacc cctacggtgt caacaatctg     1920
tcagtttggg cttggatgtt ccttttcgga cacctggtct gggctactgg cttcatgttc     1980
ttgatctctt ggcggggtta ctggcaagag ttgattgaaa ccatcgtttg ggcccacgag     2040
cgcactcctt tggcgaactt ggttcgttgg aaagataagc ccgttgcgtt gtccattgtt     2100
caagcccgtt tggttggttt agcccacttc accgttggtt atgtgctcac ctatgcggca     2160
ttcctaattg cttccacagc cggtaagttc ggttaa                                2196
```

```
<210> SEQ ID NO 35
<211> LENGTH: 2196
<212> TYPE: DNA
<213> ORGANISM: Synechocystis sp.
<220> FEATURE:
<221> NAME/KEY: misc_feature
<223> OTHER INFORMATION: S246C mutant polynucleotide

<400> SEQUENCE: 35
```

```
atggcaacta aatttcctaa atttagccag gatctcgccc aagacccgac tacacggcgt      60
atttggtacg ggattgctac ggcccacgac tttgaaaccc acgatgggat gactgaggag     120
aatctttacc aaaagatttt tgcctcccac tttggacaca tcgccatcat tttcctgtgg     180
acgtctgcca cccttttcca cgttgcgtgg caaggtaatt tgaacaatg gattaaagat     240 cctttaaaca ttcgcccgat cgccatgcg atttgggacc ccactttggg cgagggagct     300
gtcaatgctt tcacccaagc tggggcttct aacccggtta acattgctta ttccggggtt     360
taccactggt tctacaccat tggtatgacc accaaccaag agctctattc tggtgcggtc     420
ttcctattag tgttagcttc cctgttttta tttgcaggct ggttacacct ccaaccgaag     480
ttccgtccta gcttagcctg gttcaaaaat gccgaatccc gcttaaatca ccacctggct     540
ggtttgttcg gggttagctc cttggcttgg gctggtcact tggtccacgt tgcgattccc     600
gaagcccggg gtcaacacgt tggttgggat aacttcctgt ctactcctcc ccaccccgct     660
```

```
ggtttgatgc ctttcttcac cggcaactgg ggcgtgtatg cggcggatcc cgacactgct    720
ggccacattt ttggttgttc tgaaggtgct ggtaccgcaa tcctgacctt cctgggtggt    780
ttccatcccc aaacggaatc tctctggttg acggacattg cccaccacca tttggcgatc    840
gccgtgatct tcatcattgc tggtcacatg tatcgcacca actggggcat ggccacagc    900 atcaaagaaa ttcttaatgc ccataaaggt cccctaaccg cgcaggcca taccaacctg    960 tacgacacca tcaataactc cctccacttc caactcggct tagccttggc aagcttaggg   1020
gttattactt ccctggtggc gcagcacatg tactccctgc cctcctacgc ctttattgcc   1080
caggaccaca ccacccaggc agccctctac acccatcacc agtacattgc tggattcttg   1140
atggttggtg cttttgccca cggtgccatc ttctttgtcc gggattacga tcccgtggcc   1200
aataaagata acgtgctggc ccgcatgctt gaacacaaag aggctctgat tcccacttac   1260
agctgggtgt ccctcttctt gggcttccac acccttggtc tttatgtcca taacgatgtg   1320
gtggtggcct tcggtactcc cgaaaaacaa attctgatcg agcccgtttt tgcccaatgg   1380
attcaagcaa cttccggtaa agctctctat ggctttgatg ttttgctctc caatcctgac   1440
agcattgctt ccaccactgg agccgcttgg ttacccggct ggttggatgc tatcaacagc   1500
ggcaccaact ctctgttctt gaccattggc cctggcgact tcttggttca ccacgcgatc   1560
gccctagggt tgcacaccac tgccctgatt ctaatcaaag gtgctttgga tgcccgtggt   1620
tctaagttga tgccggacaa aaaggacttc ggttactcct tccctgtga tggccccggc   1680 cgtggcggta cctgcgacat ctctgcttgg gatgccttct acctagccat gttctggatg   1740
ctgaacacct tgggttggtt gaccttctac tggcactgga acacctcgg tgtttggagc   1800 ggtaacgttg tcagttcaa cgaaaactcc acctacctga tgggttggtt ccgggattac   1860
ctctgggcga actctgctca gttaatcaat ggttacaacc cctacggtgt caacaatctg   1920
tcagtttggg cttggatgtt ccttttcgga cacctggtct gggctactgg cttcatgttc   1980
ttgatctctt ggcggggtta ctggcaagag ttgattgaaa ccatcgtttg ggcccacgag   2040
cgcactcctt tggcgaactt ggttcgttgg aaagataagc ccgttgcgtt gtccattgtt   2100
caagcccgtt tggttggttt agcccacttc accgttggtt atgtgctcac ctatgcggca   2160
ttcctaattg cttccacagc cggtaagttc ggttaa                             2196
```

<210> SEQ ID NO 36
<211> LENGTH: 246
<212> TYPE: DNA
<213> ORGANISM: Synechocystis sp.
<220> FEATURE:
<221> NAME/KEY: misc_feature
<223> OTHER INFORMATION: W31C mutant polynucleotide

<400> SEQUENCE: 36

```
atgtcccata gtgtaaaaat ttacgatacc tgtattggtt gtacccaatg cgtccgggct     60
tgccccctcg atgttctaga aatggtgccc tggtgtggtt gtaaagccgc tcagatcgcc    120
tcctcccctc gaaccgagga ttgtgttggc tgcaaacgtt gtgagaccgc ctgtcccaca    180 gacttttaa gtatccgagt ttatttgggt gccgaaacca cccgcagtat gggtttagct    240
tactaa                                                               246
```

<210> SEQ ID NO 37
<211> LENGTH: 2196
<212> TYPE: DNA
<213> ORGANISM: Synechocystis sp.

<220> FEATURE:
<221> NAME/KEY: misc_feature
<223> OTHER INFORMATION: D235C/Y634 mutant polynucleotide

<400> SEQUENCE: 37

```
atggcaacta aatttcctaa atttagccag gatctcgccc aagacccgac tacacggcgt      60
atttggtacg ggattgctac ggcccacgac tttgaaaccc acgatgggat gactgaggag     120
aatctttacc aaaagatttt tgcctccac tttggacaca tcgccatcat tttcctgtgg      180
acgtctggca cccttttcca cgttgcgtgg caaggtaatt tgaacaatg gattaaagat      240
cctttaaaca ttcgcccgat cgcccatgcg atttgggacc ccactttgg cgagggagct      300
gtcaatgctt tcacccaagc tggggcttct aacccggtta acattgctta ttccggggtt     360
taccactggt tctacaccat ggtatgacc accaaccaag agctctattc tggtgcggtc      420
ttcctattag tgttagcttc cctgttttta tttgcaggct ggttacacct ccaaccgaag     480
ttccgtccta gctagcctg gttcaaaaat gccgaatccc gcttaaatca ccacctggct      540
ggtttgttcg ggttagctc cttggcttgg gctggtcact tggtccacgt tgcgattccc     600
gaagcccggg gtcaacacgt tggttgggat aacttcctgt ctactcctcc ccaccccgct    660
ggtttgatgc ctttcttcac cggcaactgg ggcgtgtatg cggcgtgtcc cgacactgct   720
ggccacattt ttggtacttc tgaaggtgct ggtaccgcaa tcctgacctt cctgggtggt   780
ttccatcccc aaacggaatc tctctggttg acggacattg cccaccacca tttggcgatc    840
gccgtgatct tcatcattgc tggtcacatg tatcgcacca ctggggcat ggccacagc     900
atcaaagaaa ttcttaatgc ccataaaggt cccctaaccg gcgcaggcca taccaacctg   960
tacgacacca tcaataactc cctccacttc caactcggct tagccttggc aagcttaggg  1020
gttattactt ccctggtggc gcagcacatg tactccctgc cctcctacgc ctttattgcc  1080
caggaccaca ccacccaggc agccctctac acccatcacc agtacattgc tggattcttg  1140
atggttggtg cttttgccca cggtgccatc ttctttgtcc gggattacga tcccgtggcc  1200
aataaagata acgtgctggc ccgcatgctt gaacacaaag aggctctgat tcccacttta  1260
agctgggtgt ccctcttctt gggcttccac acccttggtc tttatgtcca taacgatgtg  1320
gtggtggcct tcggtactcc cgaaaaacaa attctgatcg agcccgtttt tgcccaatgg  1380
attcaagcaa cttccggtaa agctctctat ggctttgatg ttttgctctc caatcctgac  1440
agcattgctt ccaccactgg agccgcttgg ttacccggct ggttggatgc tatcaacagc  1500
ggcaccaact ctctgttctt gaccattggc cctggcgact tcttggttca ccacgcgatc  1560
gccctagggt tgcacaccac tgccctgatt ctaatcaaag gtgctttgga tgcccgtggt  1620
tctaagttga tgccggacaa aaaggacttc ggttactcct tcccctgtga tggccccggc  1680
cgtggcggta cctgcgacat ctctgcttgg gatgccttct acctagccat gttctggatg  1740
ctgaacacct tgggttggtt gaccttctac tggcactgga acacctcgg tgtttggagc  1800
ggtaacgttg ctcagttcaa cgaaaactcc acctacctga tgggttggtt ccgggattac  1860
ctctgggcga actctgctca gttaatcaat ggttacaacc cctgcgggtgt caacaatctg  1920
tcagtttggg cttggatgtt ccttttcgga cacctggtct gggctactgg cttcatgttc  1980
ttgatctctt ggcggggtta ctggcaagag ttgattgaaa ccatcgtttg ggcccacgag  2040
cgcactcctt tggcgaactt ggttcgttgg aaagataagc ccgttgcgtt gtccattgtt  2100
caagcccgtt tggttggttt agcccacttc accgttggtt atgtgctcac ctatgcggca  2160
ttcctaattg cttccacagc cggtaagttc ggttaa                             2196
```

<210> SEQ ID NO 38
<211> LENGTH: 2196
<212> TYPE: DNA
<213> ORGANISM: Synechocystis sp.
<220> FEATURE:
<221> NAME/KEY: misc_feature
<223> OTHER INFORMATION: S246C/Y634C mutantpolynucleotide

<400> SEQUENCE: 38

| | | | | | |
|---|---|---|---|---|---|
| atggcaacta | aatttcctaa | atttagccag | gatctcgccc | aagacccgac | tacacggcgt | 60 |
| atttggtacg | ggattgctac | ggcccacgac | tttgaaaccc | acgatgggat | gactgaggag | 120 |
| aatctttacc | aaaagatttt | tgcctccac | tttggacaca | tcgccatcat | tttcctgtgg | 180 |
| acgtctggca | ccctttcca | cgttgcgtgg | caaggtaatt | ttgaacaatg | gattaaagat | 240 |
| cctttaaaca | ttcgcccgat | cgcccatgcg | atttgggacc | ccactttgg | cgagggagct | 300 |
| gtcaatgctt | tcacccaagc | tggggcttct | aacccggtta | acattgctta | ttccggggtt | 360 |
| taccactggt | tctacaccat | tggtatgacc | accaaccaag | agctctattc | tggtgcggtc | 420 |
| ttcctattag | tgttagcttc | cctgttttta | tttgcaggct | ggttacacct | ccaaccgaag | 480 |
| ttccgtccta | gcttagcctg | gttcaaaaat | gccgaatccc | gcttaaatca | ccacctggct | 540 |
| ggtttgttcg | gggttagctc | cttggcttgg | gctggtcact | tggtccacgt | tgcgattccc | 600 |
| gaagcccggg | gtcaacacgt | tggttgggat | aacttcctgt | ctactcctcc | ccacccgct | 660 |
| ggtttgatgc | cttctcttcac | cggcaactgg | ggcgtgtatg | cggcggatcc | cgacactgct | 720 |
| ggccacattt | ttggttgttc | tgaaggtgct | ggtaccgcaa | tcctgacctt | cctgggtggt | 780 |
| ttccatcccc | aaacggaatc | tctctggttg | acggacattg | cccaccacca | tttggcgatc | 840 |
| gccgtgatct | tcatcattgc | tggtcacatg | tatcgcacca | actggggcat | ggccacagc | 900 |
| atcaaagaaa | ttcttaatgc | cataaaggt | cccctaaccg | cgcaggcca | taccaacctg | 960 |
| tacgacacca | tcaataactc | cctccacttc | caactcggct | tagccttggc | aagcttaggg | 1020 |
| gttattactt | ccctggtggc | gcagcacatg | tactcctgc | cctcctacgc | ctttattgcc | 1080 |
| caggaccaca | ccacccaggc | agccctctac | acccatcacc | agtacattgc | tggattcttg | 1140 |
| atggttggtg | cttttgccca | cggtgccatc | ttctttgtcc | gggattacga | tcccgtggcc | 1200 |
| aataaagata | acgtgctggc | ccgcatgctt | gaacacaaag | aggctctgat | ttcccactta | 1260 |
| agctgggtgt | ccctcttctt | gggcttccac | acccttggtc | tttatgtcca | taacgatgtg | 1320 |
| gtggtggcct | tcggtactcc | cgaaaaacaa | attctgatcg | agcccgtttt | tgcccaatgg | 1380 |
| attcaagcaa | cttccggtaa | agctctctat | ggctttgatg | ttttgctctc | caatcctgac | 1440 |
| agcattgctt | ccaccactgg | agccgcttgg | ttacccggct | ggttggatgc | tatcaacagc | 1500 |
| ggcaccaact | ctctgttctt | gaccattggc | cctggcgact | tcttggttca | ccacgcgatc | 1560 |
| gccctagggt | tgcacaccac | tgccctgatt | ctaatcaaag | gtgctttgga | tgcccgtggt | 1620 |
| tctaagttga | tgccggacaa | aaaggacttc | ggttactcct | tccctgtga | tggccccggc | 1680 |
| cgtggcggta | cctgcgacat | ctctgcttgg | gatgccttct | acctagccat | gttctggatg | 1740 |
| ctgaacacct | tgggttggtt | gaccttctac | tggcactgga | acacctcgg | tgtttggagc | 1800 |
| ggtaacgttc | tcagttcaa | cgaaaactcc | acctacctga | tgggttggtt | ccggattac | 1860 |
| ctctgggcga | actctgctca | gttaatcaat | ggttacaacc | cctgcggtgt | caacaatctg | 1920 |
| tcagtttggg | cttggatgtt | ccttttcgga | cacctggtct | gggctactgg | cttcatgttc | 1980 |
| ttgatctctt | ggcggggtta | ctggcaagag | ttgattgaaa | ccatcgtttg | ggcccacgag | 2040 |

-continued

```
cgcactcctt tggcgaactt ggttcgttgg aaagataagc ccgttgcgtt gtccattgtt    2100
caagcccgtt tggttggttt agcccacttc accgttggtt atgtgctcac ctatgcggca    2160
ttcctaattg cttccacagc cggtaagttc ggttaa                              2196
```

OPTOELECTRONIC DEVICE AND METHOD OF FABRICATING THE SAME

RELATED APPLICATIONS

This Application is a Continuation-In-Part (CIP) of PCT Patent Application No. PCT/IL2006/000241, filed on Feb. 22, 2006, which claims the benefit of priority from U.S. patent application Ser. No. 60/654,502 filed on Feb. 22, 2005. The contents of the above patent Applications are incorporated herein by reference.

FIELD AND BACKGROUND OF THE INVENTION

The present invention relates to photocatalytic units and, more particularly, to solid supports fabricated with same. The present invention also relates to an optoelectronic device incorporating the photocatalytic units and method of fabricating the same.

Nanoscience is the science of small particles of materials and is one of the most important research frontiers in modern technology. These small particles are of interest from a fundamental point of view since they enable construction of materials and structures of well-defined properties. With the ability to precisely control material properties arise new opportunities for technological and commercial development, and applications of nanoparticles have been shown or proposed in areas as diverse as micro- and nanoelectronics, nanofluidics, coatings and paints and biotechnology.

It is well established that future development of microelectronics, magnetic recording devices and chemical sensors will be achieved by increasing the packing density of device components. Traditionally, microscopic devices have been formed from larger objects, but as these products get smaller, below the micron level, this process becomes increasingly difficult. It is therefore appreciated that the opposite approach is to be employed, essentially, the building of microscopic devices from a molecular level up, primarily via objects of nanometric dimensions.

Solar cells or photovoltaic cells (PVC) are optoelectronic devices in which an incident photonic energy such as sunlight is converted to electrical power. The use of PVC are as alternative source for renewable energy gain importance because of the increasing cost of fossil oil, the adverse effect of pollution on the health and on the environment and the prospect of future depletion of the oil reserves. Current technology uses silicon-based or other types of semiconductor PVCs. PVC are already commercially available and most widely used with an average energy conversion efficiency of 13%. Under research and development are crystalline and thin layer silicon, GaAs and multi-junction devices some of which can reach up to 30% efficiency. Some of the high efficiency PVC are equipped with concentrating mirrors to reduce the size and therefore the cost of the PVC. A construction of an optimal PVC cell in which the efficiency per cost ratio is high is yet to be achieved. For this reason, various types of photoactive materials have been investigated in addition to Si and GaAs. Several inorganic materials such as $CuInSe_2$, $CdTe/Se$, organic and dye synthesized molecules and polymeric films were investigated. Chlorophyll and chlorophyll derivatives were successfully used as sensitizing dyes in PVC [Radziemska, E. Progress in Energy and Combustion Science 2003, 29, 407-424] over the years. These materials are also useful for constructing light emitting devices.

Conventionally, these types of solar cells are fabricated by sandwiching a semiconductor p-n junction between a light transmissive electrode and an additional electrode. When a photon enters into the p-n junction, under an appropriate bias voltage, an electron-hole separation takes place and a photocurrent is generated. Presently known technology uses silicon-based or other types of PVCs. Such devices, however, are costly and their efficiency is far from being satisfactory. For example, commercially available silicon PVC is known to have an average energy conversion efficiency of 13%. It is expected that crystalline and thin layer silicon, GaAs and multi-junction devices which are currently under research and development, will reach efficiency of 24% for silicon and 34% for GaAs. These devices, however, are even more expensive than commercial silicon PVCs. To reduce cost, compromises are made on the size and bulkiness of the device. For example, known in the art are photovoltaic systems which incorporate mirrors to concentrate sunlight on small area of a photovoltaic cell.

Also known, are polymeric and dye-based PVCs. This technology, however, has not yet matured to provide high energy conversion efficiency. Polymeric and dye-based PVCs have reported to provide energy conversion efficiency of 5% or less.

Pigment-protein complexes which are responsible for photosynthetic conversion of light energy to chemical energy may be used as electronic components in a variety of light based devices. Although fabrication of molecular circuits is presently beyond the resolution of conventional patterning techniques such as electron beam lithography, positioning of molecules with sub nanometer precision is routine in nature, and crucial to the operation of biological complexes such as photosynthetic complexes.

Green plants, cyanobacteia and photosynthetic bacteria capture and utilize sunlight by means of molecular electronic complexes, reaction centers that are embedded in their membranes. In oxygenic plants and cyanobacteria, photon capture and conversion of light energy into chemical energy take place in specialized membranes called thylakoids. The thylkoids are located in chloroplast in higher plants or consists of foldings of the cytoplasmic membrane in cyanobacteria. The thylakoids, consisting of stacked membrane disks (called grana) and unstacked membrane disks (called stroma). The thylakoid membrane contains two key photosynthetic components, photosystem I and photosystem II, designated PS I and PS II, respectively. Photosynthesis requires PSII and PSI working in sequence, using water as the source of electrons and $CO_2$ as the terminal electron acceptor.

PS I is a transmembrane multisubunit protein-chlorophyll complex that mediates vectorial light-induced electron transfer from plastocyanin or cytochrome $C_{553}$ to ferredoxin. The nano-size dimension, an energy yield of approximately 58% and the quantum efficiency of almost 1 [K. Brettel, *Biochim. Biophys. Acta* 1997, 1318 322-373] makes the reaction center a promising unit for applications in molecular nano-electronics.

The crystalline structures of PS I from *Synechococus elongatus* and from plant chloroplast were resolved to 2.5 Å at 4.4 Å, respectively [P. Jordan, et al., *Nature* 2001, 411 909-917; A. Ben Shem, et al., *Nature* 2003, 426 630-635]. In cyanobacteria and plants, the complex consists of 12 polypeptides. Some of the polypeptides bind 96 light-harvesting chlorophyll and 22 beta carotenoide molecules. The electron transport chain contains P700, $A_0$, $A_1$, $F_X$, $F_A$ and $F_B$ representing a chlorophyll a dimmer, a monomeric chlorophyll a, two phylloquinones and three [4Fe-4S] iron sulfur centers, respectively. The reaction center core complex is made up of the heterodimeric PsaA and PsaB subunits, containing the primary electron donor, P700, which undergoes light-induced charge separation and transfers an electron through the sequential carriers $A_0$, $A_1$ and $F_X$. The final acceptors $F_A$ and $F_B$ are located on another subunit, PsaC. The redox potential of the primary donor P700 is +0.43 V and that of the final acceptor $F_B$ is −0.53 V producing redox difference of −1.0 V. The charge separation spans about 5 nm of the height of the protein representing the center to center distance between the primary donor (P700) and the final acceptor ($F_B$). The protein complex is 9 nm in height and a diameter of 21 nm and 15 for the trimer and the monomer respectively.

It is recognized that in order to incorporate PS I reaction centers into molecular devices, it is essential to immobilize the PSI reaction centers onto a substrate without their denaturation.

In earlier works, care was taken to non-covalently attach plant PS I [I. Lee, et al, *J. Phys. Chem. B* 2000, 104 2439-2443; R. Das, *Nano Letters* 2004, 4 1079-1083] and bacterial reaction centers [C. Nakamura et al., *Applied Biochemistry and Biotechnology* 2000, 84-6 401-408; S. A. Trammell, et al., *Biosensors & Bioelectronics* 2004, 19 1649-1655] to solid surfaces so as to avoid inactivation of self-assembled monolayers.

Thus, genetic modifications of both a bacterial reaction center [S. A. Trammell, et al., *Biosensors & Bioelectronics* 2004, 19 1649-1655] and a plant PS I [Das, *Nano Letters* 2004, 4 1079-1083] by addition of a 6 histidine tail allows for non-covalent binding to a polymer coated metal surface. The histidine attached bacterial reaction center was shown to produce photocurrent in solution in electrochemical cell. The histidine tagged PS I was shown to be oriented but was not reported to produce either photocurrent or photopotential. In addition, the histidine tagged PS I as taught by Das supra, required stabilization using peptide surfactants in order to attach to solid surfaces. Lee et al., [*J. Phys. Chem. B* 2000] teaches coating a metal surface with organic molecules and adsorbing the PS I non-covalently to the organic layer. In this case, the proteins assumed several orientations. Lee et al., [*Biosensors & Bioelectronics*, 1996, 11-4, 375-387] teaches platinum precipitation on the surface of photosynthetic membranes, assuming formation of direct electrical contact with the acceptor side of PS I, because it can catalyze hydrogen evolution. Additionally, it has been shown that isolated PS I reaction centers can be platinized since after the platinization it produced hydrogen in the light.

However, none of these methods teach covalent attachment of functional PS I reaction centers to a solid surface and certainly not in an oriented manner. PS I reaction centers which are not oriented will cancel each other out, preventing the PS I-immobilized devices to be used in photoelectric devices such as solar batteries or logic gates.

There is thus a widely recognized need for, and it would be highly advantageous to synthesize active PS I reaction centers capable of binding to a solid surface in an oriented manner, thereby to allow fabrication of optoelectronic device devoid the above limitations.

SUMMARY OF THE INVENTION

According to one aspect of the present invention there is provided a modified isolated polypeptide comprising an amino acid sequence of a polypeptide of a photocatalytic unit of a photosynthetic organism, the amino acid sequence being capable of mediating covalent attachment of the photocatalytic unit to a solid surface and maintaining a photocatalytic activity of the photocatalytic unit when attached to the solid surface.

According to another aspect of the present invention there is provided a plurality of isolated polypeptides, comprising an amino acid sequence of a polypeptide of a photocatalytic unit of a photosynthetic organism, the amino acid sequence being capable of mediating covalent attachment of the photocatalytic unit to a solid surface and maintaining a photocatalytic activity of the photocatalytic unit when attached to the solid surface, being capable of orientating at a substantially similar direction with respect to the solid surface.

According to yet another aspect of the present invention there is provided an isolated modified photocatalytic unit comprising the modified polypeptide comprising an amino acid sequence of a polypeptide of a photocatalytic unit of a photosynthetic organism, the amino acid sequence being capable of mediating covalent attachment of the photocatalytic unit to a solid surface and maintaining a photocatalytic activity of the photocatalytic unit when attached to the solid surface.

According to still another aspect of the present invention there is provided membrane preparation comprising the modified photocatalytic unit comprising the modified polypeptide comprising an amino acid sequence of a polypeptide of a photocatalytic unit of a photosynthetic organism, the amino acid sequence being capable of mediating covalent attachment of the photocatalytic unit to a solid surface and maintaining a photocatalytic activity of the photocatalytic unit when attached to the solid surface.

According to an additional aspect of the present invention there is provided an isolated polynucleotide encoding the modified polypeptide comprising an amino acid sequence of a polypeptide of a photocatalytic unit of a photosynthetic organism, the amino acid sequence being capable of mediating covalent attachment of the photocatalytic unit to a solid surface and maintaining a photocatalytic activity of the photocatalytic unit when attached to the solid surface.

According to yet an additional aspect of the present invention there is provided a nucleic acid construct comprising the polynucleotide encoding the modified polypeptide comprising an amino acid sequence of a polypeptide of a photocatalytic unit of a photosynthetic organism, the amino acid sequence being capable of mediating covalent attachment of the photocatalytic unit to a solid surface and maintaining a photocatalytic activity of the photocatalytic unit when attached to the solid surface.

According to still an additional aspect of the present invention there is provided a cell comprising the isolated polynucleotide encoding the modified polypeptide comprising an amino acid sequence of a polypeptide of a photocatalytic unit of a photosynthetic organism, the amino acid sequence being capable of mediating covalent attachment of the photocatalytic unit to a solid surface and maintaining a photocatalytic activity of the photocatalytic unit when attached to the solid surface.

According to a further aspect of the present invention there is provided a device, comprising a solid surface attached to a plurality of modified photocatalytic units comprising the modified polypeptide comprising an amino acid sequence of a polypeptide of a photocatalytic unit of a photosynthetic organism, the amino acid sequence being capable of mediating covalent attachment of the photocatalytic unit to a solid surface and maintaining a photocatalytic activity of the photocatalytic unit when attached to the solid surface.

According to still a further aspect of the present invention there is provided an optoelectronic device comprising at least one layer of photoactive nanoparticles interposed between a first electrode and a second electrode, wherein at least one of the first electrode and the second electrode is light transmissive.

According to still a further aspect of the present invention there is provided an optoelectronic array comprising a plurality of the optoelectronic devices described herein.

According to further features in preferred embodiments of the invention described below, the second electrode is light transmissive and a work function characterizing the second electrode is higher than a work function characterizing the first electrode.

According to still further features in the described preferred embodiments the device further comprises a dielectric layer deposited on the first electrode and having therein a cavity containing the layer(s) of photoactive nanoparticles, wherein the first electrode is exposed at a base of the cavity.

According to still further features in the described preferred embodiments the device further comprises a substrate carrying the first electrode and the dielectric layer. The substrate has thereon two or more electrical contacts, each being in electrical communication with one electrode.

According to still further features in the described preferred embodiments at least a few of the optoelectronic devices share the first electrode. According to still further features in the described preferred embodiments at least a few of the optoelectronic devices share the second electrode.

According to still further features in the described preferred embodiments the plurality of optoelectronic devices comprise: a first conductive layer having a plurality of electrodes each serving as the first electrode; a dielectric layer deposited on the first layer and being formed with a plurality of cavities therein, wherein each cavity of the plurality of cavities is positioned above an electrode of the first layer and comprises one or more layers of photoactive nanoparticles; and a second conductive layer deposited over the cavities and having a plurality of electrodes each serving as the second electrode.

According to still a further aspect of the present invention there is provided a method of fabricating an optoelectronic device, comprising covalently attaching photocatalytic units of photosynthetic organisms to at least one first electrode, thereby providing a layer of photoactive nanoparticles on the least one first electrode, and depositing at least one second electrode on the layer of photoactive nanoparticles.

According to still further features in the described preferred embodiments the method further comprises attaching at least one additional layer of photoactive nanoparticles on the layer of photoactive nanoparticles.

According to further features in preferred embodiments of the invention described below, the method further comprises depositing the at least one first electrode on a substrate.

According to still further features in the described preferred embodiments the method further comprises depositing a dielectric layer on the at least one first electrode and forming a cavity in the dielectric layer so as to expose the at least one first electrode.

According to still further features in the described preferred embodiments the attachment is effected by light induced adsorption.

According to still further features in the described preferred embodiments the deposition of the second electrode comprises sputtering deposition.

According to still further features in the described preferred embodiments the deposition of the second electrode comprises indirect evaporation.

According to still further features in the described preferred embodiments the photoactive nanoparticles comprise conducting solid surfaces covalently attached to photocatalytic units of photosynthetic organisms.

According to further features in preferred embodiments of the invention described below, the photosynthetic organism is a green plant.

According to still further features in the described preferred embodiments, the photosynthetic organism is a cyanobacteria.

According to still further features in the described preferred embodiments, the photocatalytic unit is PS I.

According to still further features in the described preferred embodiments, the photocatalytic unit is a *Synechosystis* sp. PCC 6803 photocatalytic unit.

According to still further features in the described preferred embodiments, the amino acid sequence of the polypeptide of the photocatalytic unit comprises at least one substitution mutation.

According to still further features in the described preferred embodiments, the substitution mutation is on an extramembrane loop of the photocatalytic unit.

According to still further features in the described preferred embodiments, the amino acid sequence of the polypeptide is Psa B.

According to still further features in the described preferred embodiments, the amino acid sequence of the polypeptide is Psa C.

According to still further features in the described preferred embodiments, the psa B comprises a substitution mutation in at least one position demarked by the coordinates D236C, S247C, D480C, S500C, S600C, Y635C.

According to still further features in the described preferred embodiments, the psa C comprises a substitution mutation in at least one position demarked by the coordinates W31C.

According to still further features in the described preferred embodiments, the at least one substitution mutation is cysteine.

According to still further features in the described preferred embodiments, the amino acid sequence is as set forth in SEQ ID NOs: 20, 21, 22, 23, 24, 25, 26, 27, 28 and 29.

According to still further features in the described preferred embodiments, the solid surface is a conducting material.

According to still further features in the described preferred embodiments, the conducting material is a transition metal.

According to still further features in the described preferred embodiments, the transition metal is selected from the group consisting of silver, gold, copper, platinum, nickel aluminum and palladium.

According to still further features in the described preferred embodiments, the modified isolated polypeptide does not comprise metal ions.

According to still further features in the described preferred embodiments, the modified isolated polypeptide is in a monomeric form or a trimeric form.

According to still further features in the described preferred embodiments, the nucleic acid construct further comprises a cis-regulatory element.

According to still further features in the described preferred embodiments, the cis-regulatory element is a promoter.

According to still further features in the described preferred embodiments, the cell is a *Synechocystis* cell.

According to still further features in the described preferred embodiments, the distance between each of the plurality of modified photocatalytic units is between 15-25 nm.

According to still further features in the described preferred embodiments, the plurality of modified photocatalytic units are oriented with respect to the solid surface.

According to still further features in the described preferred embodiments, the device serves as a component in a photodiode.

According to still further features in the described preferred embodiments, the device serves as a component in a phototransistor.

According to still further features in the described preferred embodiments, the device serves as a component in a logic gate.

According to still further features in the described preferred embodiments, the device serves as a component in a solar cell.

According to still further features in the described preferred embodiments, the device serves as a component in an optocoupler.

According to still further features in the described preferred embodiments, the plurality of modified photocatalytic units are directly attached to the solid surface.

According to still further features in the described preferred embodiments, the directly attached is covalently attached.

The present invention successfully addresses the shortcomings of the presently known configurations by providing a Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1E:
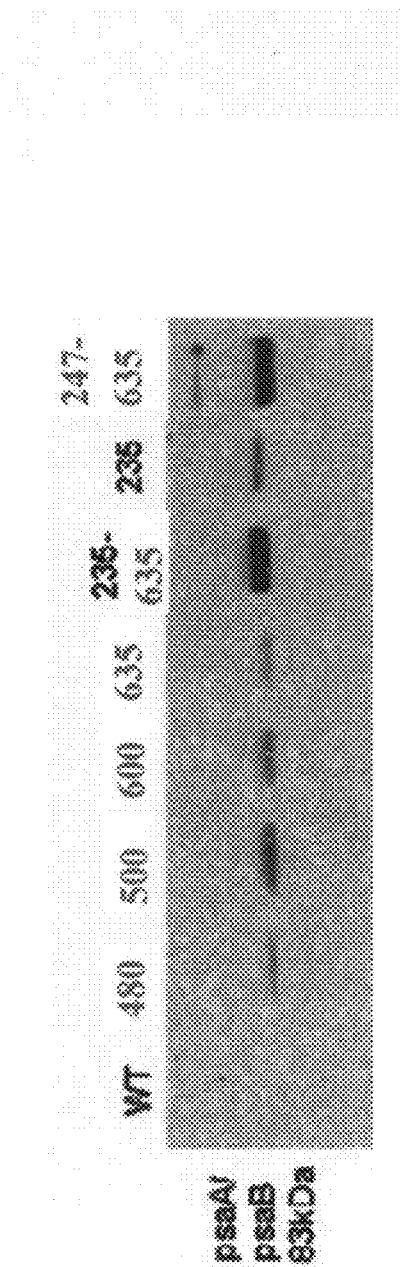

FIGS. 1A-E describe the cysteine mutations in PS I and provide evidence that the cysteine mutations are on the external surface of PS I. FIGS. 1A-C are schemes of the vectors used for induction of mutations in psaB of *Synechocystis* sp. PCC 6803 by homologous recombination. Plasmid pZBL was constructed by insertion of a 1.8 kb fragment of the psaB gene, a kanamycin resistance conferring gene (Kan$^R$) and the 1.1 kb downstream flanking region into the pBluescript vector (FIG. 1B). For selection of a psaB deficient recipient cells a pBLΔB vector was constructed by removal of 1.3 kb of downstream end of psaB and insertion of a Chloramphenicol resistant gene (Cm$^R$) (FIG. 1C). The restriction sites on the genomic DNA are indicated in FIG. 1A. FIG. 1D is a backbone presentation of the structure of PS I with the proposed mutations in "spacefill". The arrow shows the direction of light induced charge transfer. The amino acids in the PsaB subunit that were mutated to cysteines are displayed from left to right as the following: D236C, S247C, D480C, S500C, S600C, Y6354C. The coordinates were taken from PDB file JBO1 and displayed with the aid of RasMole software. FIG. 1E is a photograph of an immunoblot of surface-exposed cysteines on isolated wild type PS I complexes (lane 1) and genetically modified PS I complexes (lanes 2-7).

FIGS. 2A-B are images of two-dimensional spatial arrays of oriented PS I reaction centers on a gold surface. The images were obtained by tapping-mode atomic force microscopy (AFM; 0.3 μm$^2$ area). FIG. 2A is an image of annealed 150 nm gold surface on a silicon slide and FIG. 2B is an image of gold substrate that was incubated in a solution containing PS I monomers of mutant D480C polypeptide (SEQ ID NO: 20).

FIGS. 3A-B are two-dimensional spatial and electric potential maps of oriented PS I reaction centers on gold surfaces. Topographic (FIG. 3A) and electric potential (FIG. 3B) images of the same set of PS I reaction center trimers from mutant D480C (SEQ ID NO: 20) on a Au—Si surface. A light-induced PS I negative electrical potentials of PS I is seen in FIG. 3B. The illumination was provided by a He—Ne laser at 632.8 nm, 5 mW/cm$^2$ where indicated on the image. The negative sign of the potential shown in FIG. 3B is due to the KPFM feedback circuit and is opposite to the actual sign of the CPD.

FIGS. 4A-B are two-dimensional spatial and electric potential maps of oriented PSI reaction centers on gold surface. Topographic (FIG. 4A) and electric potential (FIG. 4B) images of the same set of PS I reaction centers trimers from mutant D480C on a Au—Si surface. A light-induced PS I negative electrical potentials of PS I is seen in FIG. 4B. The scanning directions for each raster of the constructed images were from top to bottom (from light to dark). The illumination was provided by a He—Ne laser at 632.8 nm, 5 mW/cm$^2$. The negative sign of the potential as shown in FIG. 4B is due to the KPFM feedback circuit and is opposite to the actual sign of the CPD.

FIGS. 5A-B are three-dimensional topographic and electric potential images of oriented PS I reaction centers on gold surface. FIG. 5A illustrates an electric potential image of PS I reaction centers monomers on a Au—Si surface. A light-induced PS I negative electrical potential of PS I is seen on turning the illumination by a He—Ne laser at 632.8 nm, 5 mW/cm$^2$ (hv). The scanning directions for each raster of the constructed images were from top to bottom (from dark to light). FIG. 5B illustrates a three dimensional topographic presentation of PS I trimer on Au—Si substrate.

FIGS. 6A-B are spectroscopic measurements of PS I. FIG. 6A illustrates flash induced transient absorption changes of P700 in an isolated PS I mutant (SEQ ID NO: 20). The absorption changes of P700 were monitored at 820 nm ($\Delta A_{820}$) following a saturating laser flash in D480C mutant PS I complexes. FIG. 6B illustrates X-ray absorption spectroscopy of oriented PS I complexes. PS I orientation in self assembled monolayer is determined by total reflection measurements of grazing x-ray fluorescence. PS I was attached through formation of sulfide bond between unique cysteine and tungsten on tungsten-carbon multilayer over silicon substrate. Each graph is an average of 60, 42 s scans in the indicated angle to the x-ray beam normal 25 (—), 45 (Δ), 60 (–) and 90 (O) degrees.

Figure 7:
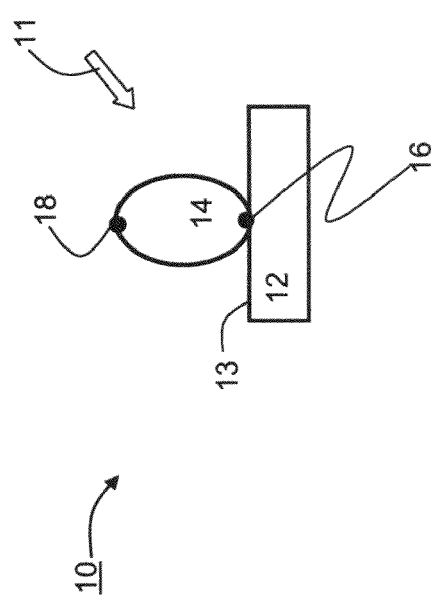

FIG. 7 is a schematic illustration of an optoelectronic device, according to various exemplary embodiments of the present invention.

Figure 8:
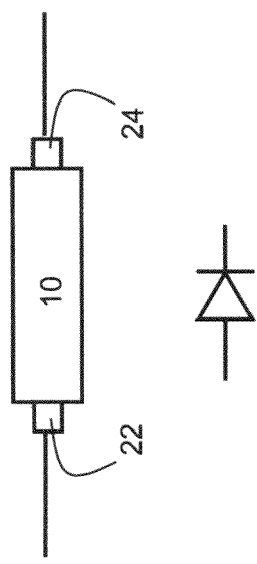

FIG. 8 is schematic illustration of a photodiode device, according to various exemplary embodiments of the present invention.

Figure 9:
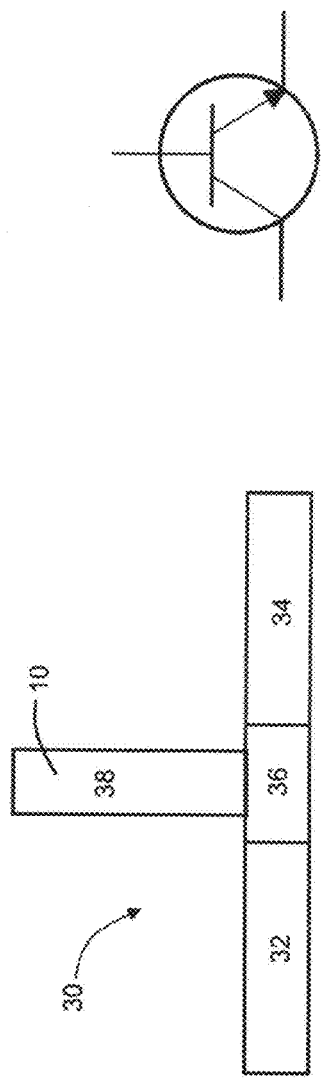

FIG. 9 is a schematic illustration of a phototransistor, according to various exemplary embodiments of the present invention.

Figure 10:
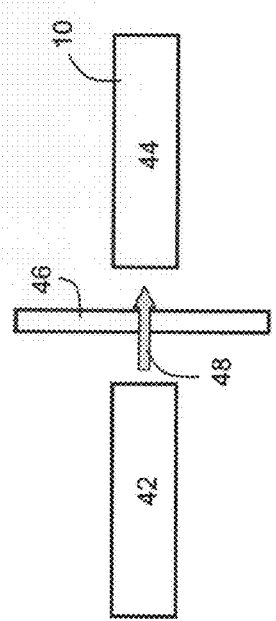

FIG. 10 is a simplified illustration of an optocoupler, according to various exemplary embodiments of the present invention.

FIGS. 11a-b are simplified illustrations of an optoelectronic device, according to various exemplary embodiments of the present invention.

FIG. 12 illustrates an energy-level diagram in the preferred embodiment in which one electrode of the device is made of aluminum and another electrode is made of indium tin oxide.

Figure 13A:
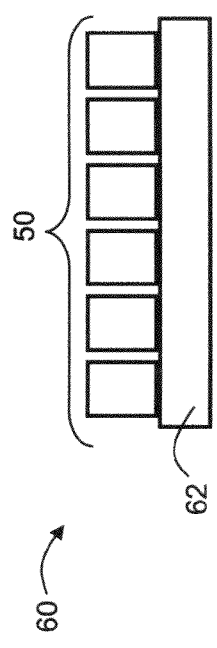
Figure 13B:
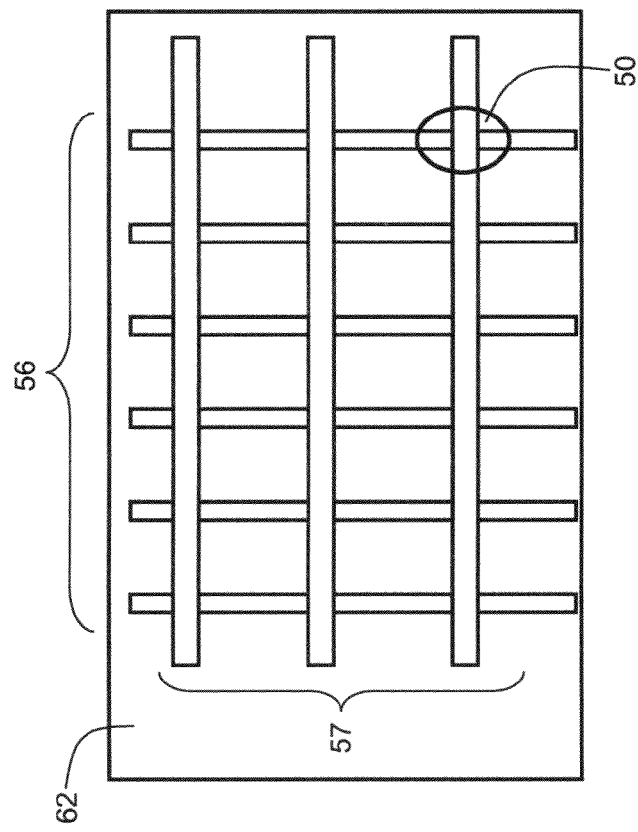

FIGS. 13a-b are schematic illustrations of an optoelectronic array, according to various exemplary embodiments of the present invention.

Figure 14:
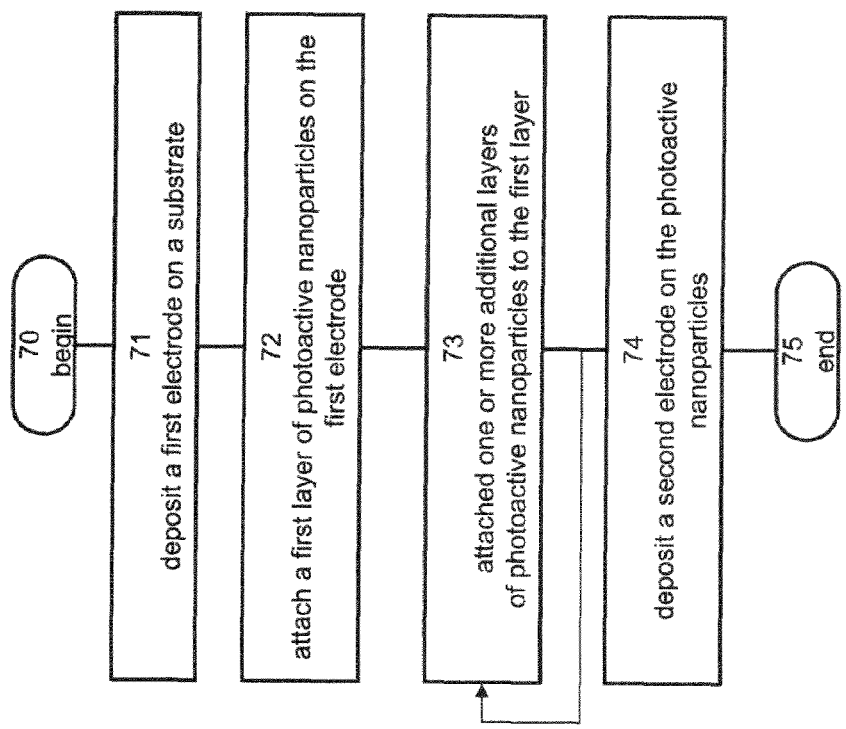

FIG. 14 is a flowchart diagram (FIG. 14) of a method suitable for fabricating an optoelectronic device, according to various exemplary embodiments of the present invention FIGS. 15a-d are schematic process illustrations of various method for fabricating the optoelectronic device, according to various exemplary embodiments of the present invention.

FIGS. 16a-d are schematic process illustrations of various method steps for fabricating the optoelectronic array, according to various exemplary embodiments of the present invention.

FIGS. 17a-c are two-dimensional spatial and electric potential maps of oriented PSI reaction centers on gold surface, in various exemplary embodiments of the invention. FIGS. 17a-b are topographic (FIG. 17a) and electric potential (FIG. 17b) images of the same set of PS I reaction center trimers from mutant D480C on an Au—Si surface. A light-induced PS I negative electrical potentials of PS I is seen in FIG. 17b. The scanning directions for each raster of the constructed images were from top to bottom (from light to dark). The illumination was provided by a He—Ne laser at 632.8 nm, 5 mW/cm2. The negative sign of the potential as shown in the figure is due to the KPFM feedback circuit and is opposite to the actual sign of the CPD50. FIG. 17c shows binding PS I under illumination.

FIG. 18a-d are images obtained by atomic force microscopy of platinized PS I monolayer. FIGS. 18a and 18c are topographic image of PS I (FIG. 18a) an platinized (FIG. 18c). FIGS. 18b and 18d show the respective phase contrast images. The features of the protein are damped by the metal in the phase images.

Figure 19:
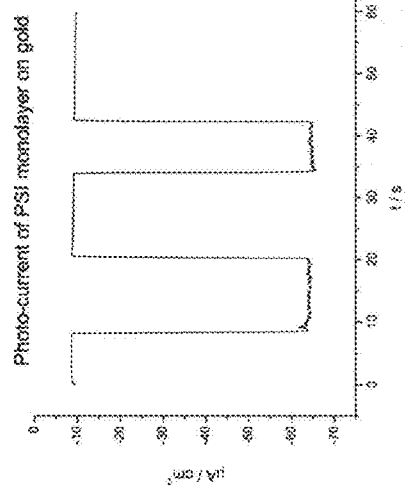

FIG. 19 shows electrochemical measurements of photocurrent in PS I monolayer on gold electrode. The working electrode was illuminated (on and off) from a 150 W slide projector through the glass wall of the cell. The medium contained 0.1 M tris-HCl, pH 7.5 and 0.05 mM methyl viologene.

Figure 20C:
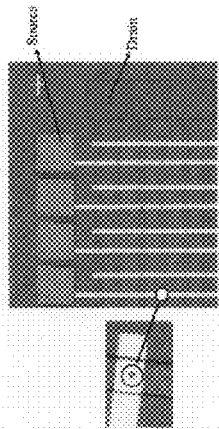
Figure 20B:
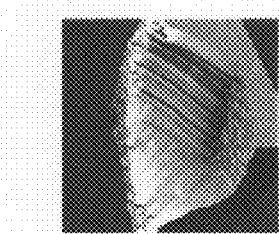
Figure 20A:
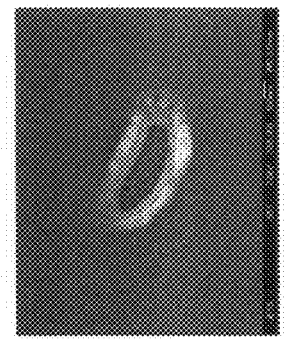

FIGS. 20a-c are images of a prototype optoelectronic array fabricated according to various exemplary embodiments of the present invention. FIG. 20a shows chemically adsorbed layer of PS I molecules (white dots); FIG. 20b is an electron microscopy image of a cavity which exposes a gold electrode;

FIG. 20c is optical microscopy image of the prototype showing an array of optoelectronic devices sandwiched between the bottom gold electrodes ("source") and the top indium tin oxide electrode ("drain").

Figure 21:
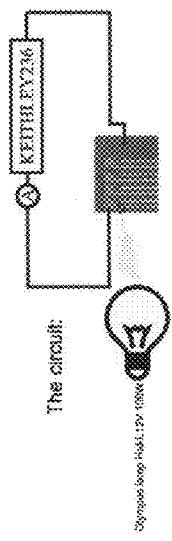

FIG. 21 is a schmatic illustration of the prototype optoelectronic array of FIGS. 20a-c.

Figure 22:
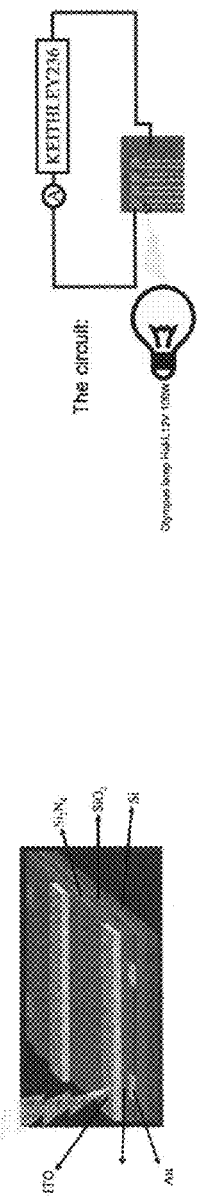

FIG. 22 is a schematic illustration of set-up used for photoconductivity experiments performed using the prototype device of FIGS. 20a-c.

Figure 23:
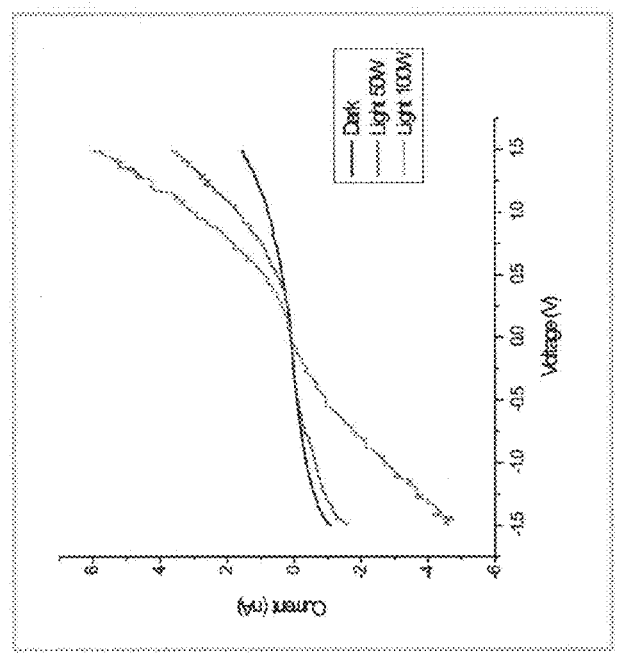

FIG. 23 the photoconductivity I/V data obtained from the experiment illustrated in FIG. 22.

DESCRIPTION OF THE PREFERRED EMBODIMENTS

The present embodiments comprise a modified photocatalytic unit which can be covalently attached to a solid support and maintain activity. Specifically, the present embodiments can be used as electronic components in a variety of different devices, include, without limitation, spatial imaging devices, solar batteries, optical computing and logic gates, optoelectronic switches, photonic A/D converters, thin film photovoltaic structures and the like.

Before explaining at least one embodiment of the invention in detail, it is to be understood that the invention is not limited in its application to the details of construction and the arrangement of the components set forth in the following description, illustrated in the drawings or exemplified by the Examples. The invention is capable of other embodiments or of being practiced or carried out in various ways. Also, it is to be understood that the phraseology and terminology employed herein is for the purpose of description and should not be regarded as limiting.

Photosynthesis is the biological process that converts electromagnetic energy into chemical energy through light and dark reactions. In oxygenic plants and cyanobacteria, photon capture and conversion of light energy into chemical energy take place in specialized membranes called thylakoids. The thylkoids are located in chloroplast in higher plants or consists of foldings of the cytoplasmic membrane in cyanobacteria.

PS I is a transmembrane multisubunit protein-chlorophyll complex that mediates vectorial light-induced electron transfer from plastocyanin or cytochrome $C_{553}$ to ferredoxin. The nano-size dimension, an energy yield of approximately 58% and the high quantum efficiency makes the reaction center a promising unit for applications in molecular nano-electronics. However, in order to incorporate PS I reaction centers into molecular devices, it is essential to immobilize the PS I reaction centers onto a substrate without their denaturation. In addition, an oriented attachment of the PS I reaction centers is imperative so that the induced electrical charges will not cancel each other out.

While reducing the present invention to practice, the present inventors discovered that polypeptides in photocatalytic units may be genetically modified such that they comprise functional groups for covalent binding to a solid surface whilst still retaining activity.

As illustrated in the Examples section which follows, utilizing publicly available structural data on the 3D structure of PS I, the present inventors mutated amino acids in the Psa B polypeptide and Psa C polypeptide of the PS I in the extra membrane loops facing the cytoplasmic side of the bacterial membrane to cysteines in order to ensure formation of sulfide bonds (between the PS I unit and a metal surface). The various mutations were selected near the P700 to secure close proximity between the reaction center and the gold electrode in order to facilitate efficient electric junction (Example 1). The present inventors also showed that by substituting an identical amino acid for cysteine in a plurality of photocatalytic units, the attachment to a solid support will be oriented and the PS I units would form a monolayer on the solid support (Example 2). The precise orientation of the photocatalytic units on the solid support may be adjusted by selecting a particular amino acid to be substituted by the cysteine residue.

PS I units modified according to the above were capable of forming oriented monolayers on gold surfaces as detected by atomic force microscopy—FIGS. 2A-B. The mutant PS I units were functionally active following attachment to a gold surface as demonstrated by their ability to produce a clear light-induced electric potential as measured by Kelvin probe force microscopy (KPFM)—FIGS. 3A-B and by their ability to transfer electrons as measured by single turnover spectroscopy [FIGS. 6A-B].

Trammel et al., [*Biosensors & Bioelectronics* 2004, 19 1649-1655] teaches a modification to a bacterial reaction center comprising a 6 histidine tail. In sharp contrast to the present invention, the mutated PS Is could not covalently bind to a metal surface.

Das [*Nano Letters* 2004, 4 1079-1083] teaches a modification to a plant reaction center comprising a 6 histidine tail. As well as not covalently binding to a metal surface, in sharp contrast to the present invention, the mutated PS Is required stabilization with peptide surfactants in order to attach to a solid surface.

Lee et al., [*J. Phys. Chem. B* 2000] teaches coating a metal surface with organic molecules and adsorbing the PS I non-covalently to the organic layer. In contrast to the present invention, the PS I proteins assumed several orientations and as such were functionally inactive.

Lee et al., [*Biosensors & Bioelectronics*, 1996, 11-4, 375-387] teaches platinum precipitation on the surface of photosynthetic membranes, thereby making direct electrical contact with the acceptor side of PS I, where it can catalyze hydrogen evolution. The potential capacity to drive photocurrent through an external circuit was not demonstrated in these studies. Similarly to Trammel et al and Das, Lee et al does not teach covalent attachment of bacterial reaction center and PS I, respectively to a solid surface. In sharp contrast to Trammell, et al., and Das, the PS I modified proteins of the present invention need not be modified to comprise metal ions since they bind to a metal surface by virtue of the introduced cysteinyl residues located at the extra-membrane loops in PS I.

Thus, according to one aspect of the present invention there is provided a modified isolated polypeptide comprising an amino acid sequence of a polypeptide of a photocatalytic unit of a photosynthetic organism, the amino acid sequence being capable of mediating covalent attachment of the photocatalytic unit to a solid surface and maintaining a photocatalytic activity of the photocatalytic unit when attached to the solid surface.

As used herein, the phrase "photocatalytic unit" refers to a complex of at least one polypeptide and other small molecules (e.g. chlorophyll and pigment molecules), which when integrated together work as a functional unit converting light energy to chemical energy. As mentioned herein above, the photocatalytic units of the present invention are present in photosynthetic organisms (i.e. organisms that convert light energy into chemical energy). Examples of photosynthetic organisms include, but are not limited to green plants, cyanobacteria, red algae, purple and green bacteria.

Thus, examples of photocatalytic units which can be used in accordance with this aspect of the present invention include biological photocatalytic units such as PS I and PS II, bacterial light-sensitive proteins, bacterial light-sensitive proteins, bacteriorhodopsin, photocatalytic microorganisms, pigments (e.g., proflavine and rhodopsin), organic dyes and algae. Preferably, the photocatalytic unit of the present invention is photosystem I (PS I).

PS I is a protein-chlorophyll complex, present in green plants and cyanobacteria, that is part of the photosynthetic machinery within the thylakoid membrane. It is ellipsoidal in shape and has dimensions of about 9 by 15 nanometers.

As used herein the term "about" refers to ±10%.

The PS I complex typically comprises chlorophyll molecules which serve as antennae which absorb photons and transfer the photon energy to P700, where this energy is captured and utilized to drive photochemical reactions. In addition to the P700 and the antenna chlorophylls, the PSI complex contains a number of electron acceptors. An electron released from P700 is transferred to a terminal acceptor at the reducing end of PSI through intermediate acceptors, and the electron is transported across the thylakoid membrane.

Examples of PS I polypeptides are listed below in Table 1 together with their source organisms.

TABLE 1

| Source Organism | Protein accession number |
| --- | --- |
| *Amphidinium carterae* | CAC34545 |
| *Juniperus chinensis* | CAC87929 |
| *Cedrus libani* | CAC87143 |
| *Spathiphyllum* sp. SM328 | CAC87924 |
| *Persea americana* | CAC87920 |
| *Zamia pumila* | CAC87935 |
| *Ophioglossum petiolatum* | CAC87936 |
| *Taxus brevifolia* | CAC87934 |
| *Afrocarpus gracilior* | CAC87933 |
| *Pinus parviflora* | CAC87932 |
| *Picea spinulosa* | CAC87931 |
| *Phyllocladus trichomanoides* | CAC87930 |
| *Serenoa repens* | CAC87923 |
| *Saururus cernuus* | CAC87922 |
| *Platanus racemosa* | CAC87921 |
| *Pachysandra terminalis* | CAC87919 |
| *Nymphaea* sp. cv. Paul Harriot | CAC87918 |
| *Nuphar lutea* | CAC87917 |
| *Nelumbo nucifera* | CAC87916 |
| *Acer palmatum* | CAD23045 |
| *Cupressus arizonica* | CAC87928 |
| *Cryptomeria japonica* | CAC87927 |
| *Abies alba*] | CAC87926 |
| *Gnetum gnemon* | CAC87925 |
| *Magnolia grandiflora* | CAC87915 |
| *Liquidambar styraciflua* | CAC87914 |
| *Lilium brownii* | CAC87913 |
| *Isomeris arborea* | CAC87912 |
| *Fagus grandifolia* | CAC87911 |
| *Eupomatia laurina* | CAC87910 |
| *Enkianthus chinensis* | CAC87909 |
| *Coptis laciniata* | CAC87908 |
| *Chloranthus spicatus* | CAC87907 |
| *Calycanthus occidentalis* | CAC87906 |
| *Austrobaileya scandens*] | CAC87905 |
| *Amborella trichopoda* | CAC87904 |
| *Acorus calamus* | CAC87142 |

According to a preferred embodiment of this aspect of the present invention, the PS I is derived from cyanobacteria and more specifically from *Synechosystis* sp. PCC 6803.

In cyanobacteria, the PS I complex consists of 12 polypeptides, some of which bind 96 light-harvesting chlorophyll and 22 beta carotenoid molecules. The electron transport chain contain P700, $A_0$, $A_1$, $F_X$, $F_A$ and $F_B$ representing a chlorophyll a dimmer, a monomeric chlorophyll a, two phylloquinones and three [4Fe-4S] iron sulfur centers, respectively. The reaction center core complex is made up of the heterodimeric PsaA and PsaB subunits, containing the primary electron donor, P700, which undergoes light-induced charge separation and transfers an electron through the sequential carriers $A_0$, $A_1$ and $F_X$. The final acceptors $F_A$ and $F_B$ are located on another subunit, PsaC.

PS Is derived from cyanobacteria are more structurally stable than those derived from plant and bacterial reaction centers. This is due to the fact that all chlorophyll molecules and carotenoids are integrated into the core subunit complexes in cyanobacteria while in plant and other bacterial reaction centers the antenna chlorophylls are bound to chlorophyll-protein complexes that are attached to the core subunits. Thus, unlike PS Is derived from other organisms such as plants and other bacteria., those derived from cyanobacteria do not require peptide surfactants for stabilization [R. Das et al., *Nano Letters* 2004, 4 1079-1083] during attachment to a solid surface.

As used herein, the term "isolated" refers to the modified photocatalytic polypeptide that has been at least partially removed from its natural site of synthesis (e.g., photosynthetic organism). Typically, the photocatalytic polypeptide is not isolated from other members of the photocatalytic unit (i.e. chlorophyll and pigment) so that the photocatalytic unit remains functional. Preferably the polypeptide is substantially free from other substances (e.g., other cells, proteins, nucleic acids, etc.) that are present in its in-vivo location.

As mentioned, the photocatalytic unit of this aspect of the present invention comprises the modified polypeptide.

The term "polypeptide" as used herein refers to a polypeptide which may be synthesized by recombinant DNA technology.

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 2 and 3 below list naturally occurring amino acids (Table 2) and non-conventional or modified amino acids (Table 3) which can be used with the present invention.

TABLE 2

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 3

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α ethylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |

TABLE 3-continued

| Non-conventional amino acid | Code | Non-conventional amino acid | Code |
|---|---|---|---|
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α ethylhistidine | Mhis | L-α-methylhomophenylalanine | Mhphe |
| L-α thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α ethylvaline | Mtrp | L-α-methyltyrosine | Mtyr |
| L-α-methylleucine | Mval nbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl hylamino)cyclopropane | Nmbc | | |

As used herein, the phrase "modified polypeptide" refers to a polypeptide comprising a modification as compared to the wild-type polypeptide. Typically, the modification is an amino acid modification. Any modification to the sequence is envisaged according to this aspect of the present invention so long as the polypeptide is capable of covalent attachment to a solid surface and retains a photocatalytic activity. Examples of modifications include a deletion, an insertion, a substitution and a biologically active polypeptide fragment thereof. Insertions or deletions are typically in the range of about 1 to 5 amino acids.

The site of modification is selected according to the suggested 3D structure of the photocatalytic unit. Evidence relating to the 3D structure of photocatalytic units may be derived from X-ray crystallography studies or using protein modeling software. The crystalline structure of PS I from *Synechococus elongatus* and from plants chloroplast has been resolved to 2.5 Å at 4.4 Å, respectively [P. Jordan, et al., *Nature* 2001, 411 909-917; A. Ben Shem, F. Frolow, N. Nelson, *Nature* 2003, 426 630-635].

The amino acid to be replaced or the site of insertion is typically on the external surface of the photocatalytic unit (e.g. on an extra membrane loop). Preferably, the amino acids to be replaced or the site of insertion is in a position which does not cause steric hindrance. Also it is preferred that the mutations are positioned near the P700 of the photocatalytic unit to secure close proximity between the reaction center and the solid surface in order to facilitate an efficient electric junction.

According to a preferred embodiment of this aspect of the present invention, the modification is a substitution (i.e. replacement) comprising a functional group side chain which is capable of mediating binding to the solid surface. Particularly preferred coordinates for mutation of PS I from *Synechocystis* sp. PCC 6803 in PsaB include single mutations D236C, S247C, D480C, S500C, S600C, and Y635C or double mutations D236C/Y635C and S247C/Y635C. In PsaC, a particularly preferred site for a mutation is W31C. In addition, a triple mutation may be generated in the photocatalytic units (e.g. PsaC//PsaB W31C//D236C/Y635C).

Preferably, the wild type amino acid which is substituted is not essential for the activity of the photocatalytic unit. Guidance in determining which amino acids are functionally redundant may be found by comparing the sequence of the photocatalytic unit with that of homologous known protein molecules and minimizing the number of amino acid sequence changes made in regions of high homology.

In one embodiment, conservative amino acid substitutions are made at one or more predicted, non-essential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In another embodiment, non-conservative amino acid substitutions may be made since the mutations are preferably designed to enable oriented covalent attachment of the protein to metal. By selecting mutant cells that can grow photoautotrophically, undamaged PS I cells may be ensured.

Preferably, the amino acids at the coordinates described hereinabove are replaced with an amino acid which is capable of binding to a metal surface—e.g. amino acids that comprise a thiol group such as cysteine.

In a preferred embodiment of this aspect of the present invention, the sequences of the polypeptides are as set forth in SEQ ID NOs: 20, 21, 22, 23, 24, 25, 26, 27, 28 and 29.

Recombinant techniques are preferably used to generate the polypeptides of the present invention since photocatalytic units typically comprise more than one polypeptide and other molecules (e.g. pigment molecules and chlorophyll) integrated into a complex. In addition, these techniques are better suited for generation of relatively long polypeptides (e.g., longer than 20 amino acids) and large amounts thereof. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

The polypeptides of the present invention may be modified by standard techniques, such as site-directed mutagenesis (oligonucleotide-mediated mutagenesis) and PCR-mediated mutagenesis. Thus a polynucleotide encoding a polypeptide of a photocatalytic unit may be mutated. Following mutagenesis the photocatalytic units can be expressed in an appropriate cell system.

Oligonucleotide-mediated mutagenesis is a technique which is well known in the art as described by Adelman et al., DNA, 2: 183 (1983). Briefly, a polynucleotide encoding a polypeptide of a photocatalytic unit (e.g. PsaB gene) is altered by hybridizing an oligonucleotide encoding the desired mutation to a polynucleotide template, where the template is the single-stranded form of the plasmid containing the unaltered or native polynucleotide sequence of the polypeptide of the photocatalytic unit. After hybridization, a DNA polymerase (e.g. Klenow fragment of DNA polymerase I) is used to synthesize an entire second complementary strand of the template that will thus incorporate the oligonucleotide primer, and will code for the selected alteration in the photocatalytic unit polynucleotide, thus producing a heteroduplex molecule.

This heteroduplex molecule is then transformed into a suitable host cell, usually a prokaryote such as *E. coli* JM101. After the cells are grown, they may be plated onto agarose plates and screened identify the bacterial colonies that contain the mutated DNA. The mutated region is then removed and placed in an appropriate vector for protein production, generally an expression vector of the type typically employed for transformation of an appropriate host.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded polynucleotide template molecule. The oligonucleotides are readily synthesized using techniques known in the art such as that described by Crea et al., Proc. Natl. Acad. Sci. USA, 75: 5765 (1978).

The polynucleotide template can only be generated by those vectors that are either derived from bacteriophage M13 vectors (the commercially available M13 mp18 and M13 mp19 vectors are suitable), or those vectors that contain a single-stranded phage origin of replication as described by Viera et al. Meth. Enzymol., 153: 3 (1987). Thus, the polynucleotide that is to be mutated must be inserted into one of these vectors to generate single-stranded template. Production of the single-stranded template is described in Sections 4.21-4.41 of Sambrook et al., Molecular Cloning: A Laboratory Manual (Cold Spring Harbor Laboratory Press, N.Y. 1989)

Mutants with more than one amino acid to be substituted may also be generated using site directed mutagenesis.

An exemplary method for mutating PS I according to the teachings of the present invention, using site-directed mutagenesis is described in Example 1 herein below.

PCR mutagenesis and cassette mutagenesis are also techniques that are suitable for modifying polypeptides of photocatalytic units—See Sambrook and Russell (2001, Molecular Cloning, A Laboratory Approach, Cold Spring Harbor Press, Cold Spring Harbor, N.Y.) and Ausubel et al. (2002, Current Protocols in Molecular Biology, John Wiley & Sons, NY).

Suitable hosts for the expression of the mutated photocatalytic sequences include any host that is capable of synthesizing a functional photocatalytic unit. Thus the host must be capable of incorporating pigment, chlorophyll molecules and the like into the unit. Examples of suitable hosts include, but are not limited to green plant cell cultures, green plants and photosynthetic bacteria. In a preferred embodiment of this aspect of the present invention, the host is *Synechocystis* bacteria.

According to a particularly preferred embodiment of the present invention, the mutated DNA is cloned by insertion into the host genome. This is particularly suitable when the host cell are photosynthetic bacteria. This method is affected by including in the vector a DNA sequence that is complementary to a sequence found in the photosynthetic genomic DNA. Transfection of photosynthetic bacteria with this vector results in homologous recombination with the genome and insertion of the photocatalytic poypeptide DNA.

An exemplary method for the transformation by homologous recombination of *Synechocystis* sp. PCC 6803 with a mutated psaB gene is described in Example 1 below. Essentially, Wild-type *Synechocystis* cells, light-activated heterotrophically grown (LAHG: grown in the dark except for 10 minutes of light at photon flux density of 40 micromol $m_{-2}s_{-1}$ every 24 h) on BG-11 plates supplemented with 5 mM glucose, 10 mM TES-KOH, pH 8 (N-tris[Hydroxymethyl]-methyl-2-aminoethanesulfonate) and thiosulfate (3 g/l), were transformed with the plasmid pZBL cloned with the mutated psaB gene. A scheme for homologous recombination is depicted in FIG. 1A. The cells were transformed with the resultant plasmids, then selected and segregated for a few generations on 5-20 mg/ml kanamycin. Selection of transformants and segregation was performed under kanamycin pressure.

Alternatively a polynucleotide encoding a modified polypeptide of the present invention may be ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above). Examples of polynucleotide sequences which may be used according to the teachings of the present invention are as set forth in SEQ ID NOs: 30, 31, 32, 33, 34, 35, 36, 37 and 38.

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

As mentioned hereinabove, polynucleotide sequences of the present invention may be inserted into expression vectors (i.e., a nucleic acid construct) to enable expression of the recombinant polypeptide. The expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

In bacterial systems, a number of expression vectors can be advantageously selected depending upon the use intended for the polypeptide expressed. For example, when large quantities of polypeptides are desired, vectors that direct the expression of high levels of the protein product, possibly as a fusion with a hydrophobic signal sequence, which directs the expressed product into the periplasm of the bacteria or the culture medium where the protein product is readily purified may be desired. Certain fusion protein engineered with a specific cleavage site to aid in recovery of the polypeptide may also be desirable. Such vectors adaptable to such manipulation include, but are not limited to, the pET series of *E. coli* expression vectors [Studier et al., Methods in Enzymol. 185:60-89 (1990)].

In cases where plant expression vectors are used, the expression of the polypeptide coding sequence can be driven by a number of promoters. For example, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] can be used. Alternatively, plant promoters can be used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VII, pp 421-463 (1988)].

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Expression and cloning vectors should contain a selection gene, also termed a selectable marker. This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media.

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Following culturing under suitable conditions, the photocatalytic units are preferably isolated from the cells. An exemplary method for removing photocatalytic units from photosynthetic organisms is described in Example 2 of the Examples section hereinbelow. The present invention also envisages using any other methods of purification and isolation so long as the photocatalytic unit remains functional. The photocatalytic units may be isolated as polymers e.g. trimers or as single monomers. The photocatalytic units may be fully isolated or part of a membrane preparation. Methods of preparing membrane extracts are well known in the art. For example, Qoronfleh et al., [J Biomed Biotechnol. 2003; 2003 (4): 249-255] teach a method for selective enrichment of membrane proteins by partition phase separation. Various kits are also commercially available for the preparation of membrane extracts such as from Sigma-Aldrich (ProteoPrep™ Membrane Extraction Kit).

Thus, according to another aspect of the present invention, there is provided an isolated modified photocatalytic unit comprising the modified polypeptide of the present invention. According to this aspect of the present invention, the term "isolated" refers to photocatalytic unit that has been at least partially removed from its natural site of synthesis (e.g., photosynthetic organism). Preferably the photocatalytic unit is substantially free from substances (e.g., other cells, proteins, nucleic acids, etc.) that are present in its in-vivo location.

The activity of the photocatalytic units may be tested following isolation as described hereinbelow.

Following isolation, the modified photocatalytic units of the present invention may be attached to a solid surface by covalent or non-covalent bonding (electrostatic). As used herein the term "covalent bond" refers to the linkage of two atoms by the sharing of two electrons, one contributed by each of the atoms. Preferably the photocatalytic unit is bonded directly to a solid surface (i.e. does not comprise any linker molecules nor is it coated with metal ions).

Selection of a solid surface depends on the modification of the photocatalytic unit. Thus, if the modification comprises a cysteine substitution, as exemplified hereinbelow, the solid surface is preferably a conducting material, such as a transition metal. Examples of transition metals which may be used according to this aspect of the present invention include, but are not limited to silver, gold, copper, platinum, nickel, aluminum and palladium.

The modified photocatalytic unit of the present embodiments can be covalently attached to a solid surface by directly reacting the substituting residue with a hydrophilic surface of a solid substrate. For example, in the preferred embodiment is which the substituting residue is cysteine, the attachment can be done by incubating the modified photocatalytic unit with gold or other metals surfaces for a period sufficient to form a sulfide bond. Other attachment methods are also contemplated. An exemplary method for covalently attaching a cysteine substituted photocatalytic unit is described in Example 2 of the Examples section herein below.

According to this aspect of the present invention, the modified photocatalytic unit retains photocatalytic activity following attachment to a solid surface.

Herein, the phrase "photocatalytic activity" refers to the conversion of light energy to chemical energy. Preferably, the modified photocatalytic units retain at least 20%, more preferably at least 30%, more preferably at least 40%, more preferably at least 50%, more preferably at least 60%, more preferably at least 70%, more preferably at least 80%, more preferably at least 90%, e.g., about 100% the activity of the wild type photocatalytic unit in its in-vivo environment. The present invention also envisages that the photocatalytic unit of the present invention comprises an activity greater than that of wild type photocatalytic unit in its in-vivo environment.

In order for the modified photocatalytic units of the present invention to comprise photocatalytic activity following attachment to a solid support, the photocatalytic units must be attached in an oriented manner so that they will not neutralize each others charge. As described in Example 3, a modified polypeptide of the present invention enables photocatalytic unit binding to a solid support such that a light-induced positive potential developed. The induced potential is a result of a negative charge displacement away from the gold side of PS I. The present inventors hypothesized that by substituting an identical amino acid for cysteine in a plurality of photocatalytic units, the attachment to a solid support will be oriented and the photocatalytic units would form a monolayer on the solid support.

The precise orientation of the photocatalytic units on the solid support may be adjusted by selecting a particular amino acid to be substituted by the cysteine residue.

Methods of measuring photocatalytic activity on surfaces fabricated therewith include measuring the photovoltage properties of the fabricated surfaces. The photovoltage properties may be measured for example by Kelvin probe force microscopy (KPFM). As illustrated in the KPFM images presented in FIGS. 3A and 3B, the photocatalytic units of the present invention demonstrate a clear light-induced electric potential. Specifically, a light-induced positive potential of +0.498±0.02 V developed where peaks ascribed to PS I complexes were observed in the topographic trace. The reversible nature of the light-induced electric potential was also demonstrated by observing a change in the potential when the illumination was turned off (FIGS. 4A-B).

Photocatalytic activity may also be measured by analyzing the electron transfer in the photocatalytic complexes. Electron transfer may be measured by analyzing flash-induced absorption changes as measured by single turnover spectroscopy. As illustrated in FIGS. 6A-B, the difference in the rate of charge recombination between that of the wild type and the mutant indicates that the cysteine substitution according to the teachings of the present invention did not alter the mode of action of light-induced electron transfer.

Reference is now made to FIG. 7, which is a schematic illustration of an optoelectronic device 10, according to various exemplary embodiments of the present invention. Device 10 comprises a solid support 12 and a plurality of isolated photocatalytic units 14 attached to a surface 13 of support 12. Isolated photocatalytic units 14 are preferably modified so as to facilitate covalent attachment of units 14 to surface 13, while maintaining the photocatalytic activity as further detailed hereinabove.

Being compose in part of photocatalytic units 14, optoelectronic device 10 facilitates light induced electron transfer. Upon excitation by light 11, an electron transfer occurs from a donor site 16, across multiple intermediate steps to an acceptor site 18, within a period of time which can be from several hundreds of picoseconds to a few microseconds, depending on the type of photocatalytic units. The frequency of light which induces the electron transfer depends on the photosynthetic organisms from which units 14 are obtained. For example, when photocatalytic units of green plants or green bacteria are employed, device 10 is sensitive to green light having wavelength of from about 400 nm to about 750 nm, when photocatalytic units of cyanobacteria are employed, device 10 is sensitive to cyan light having wavelength of from about 400 nm to about 500 nm, when photocatalytic units of red algae are employed, device 10 is sensitive to red light having wavelength of from about 650 nm to about 700 nm and when photocatalytic units of purple bacteria are employed, device 10 is sensitive to purple light having wavelength of from about 400 nm to about 850 nm.

Optoelectronic device 10 can be used in the field of micro- and sub-microelectronic circuitry and devices including, but not limited to spatial imaging devices, solar batteries, optical computing and logic gates, optoelectronic switches, diodes, photonic A/D converters, and thin film "flexible" photovoltaic structures.

Reference is now made to FIG. 8, which is a schematic illustration of a photodiode device 20, according to various exemplary embodiments of the present invention. One skilled in the art will recognize that several components appearing in FIG. 7 have been omitted from FIG. 8 for clarity of presentation. Photodiode device 20 comprises optoelectric device 10, and two electrical contacts 22 and 24 being in electrical communication with donor site 16 and acceptor site 18, respectively. Electrical communication with donor site 16 can be established, for example, by connecting a conducting material to support 12 or surface 13. The acceptor site can be covalently bound by formation of sulfide bond between the modified polypeptides of the present invention (e.g. W31C in PsaC subunit of PS I) and the top deposited metal electrode. Platinized photocatalytic units at the acceptor side can make a metal to metal electrical connection with a top electrode deposited by evaporation of thin metal electrode. Deposition of conducting polymer on top of the photocatalytic monolayer or the platinized photocatalytic monolayer can serve as a top electrode. A symbolic illustration of the photodiode is illustrated at the bottom of FIG. 8.

In use, the photocatalytic units are irradiated by light hence being excited to efficient charge separation of high quantum efficiency, which is typically above 95%. Contacts 22 and 24 tap off the electrical current caused by the charge separation. Depending on the voltage applied between contacts 22 and 24, photodiode device 20 can be used either as a photovoltaic device, or as a reversed bias photodiode.

Specifically, in the absence of external voltage, photodiode device 20 enacts a photovoltaic device which produces current when irradiated by light. Such device can serve as a component in, e.g., a solar cell.

When reverse bias is applied between contacts 22 and 24, photodiode device 20 maintains high resistance to electric current flowing from contact 24 to contact 22 as long as photodiode device 20 is not irradiated by light which excites the photocatalytic units. Upon irradiation by light at the appropriate wavelength, the resistance is significantly reduced. Such device can serve as a component in, e.g., a light detector.

Optoelectronic device 10 can also serve as a solar cell, when no bias voltage is applied. Upon irradiation of the photocatalytic units, the charge-separated state results in internal voltage between donor site 16 and acceptor site 18. The internal voltage can be tapped off via electrical contacts at donor site 16 and acceptor site 18. If the current circuit is closed externally, the current flow is maintained through repeated light-driven charge separation in the solar cell.

The generated polarized charge-separated state of device 10 can also be utilized for in a molecular transistor. Specifically, device 10 can serve as a light-charged capacitor enacting a gate electrode which modifies the density of charge carriers in a channel connected thereto.

Reference is now made to FIG. 9, which is a schematic illustration of a phototransistor 30, according to various exemplary embodiments of the present invention. Phototransistor 30 comprises a source electrode 32, a drain electrode 34, a channel 36 and a light responsive gate electrode 38. Gate electrode 38 preferably comprises optoelectronic device 10. Channel 36 preferably has semiconducting properties such that the density of charge carriers can be varied.

In the absence of light, channel 36 does not contain any free charge carriers and is essentially an insulator. Upon exposure to light, the photocatalytic units of device 10 generate a polarized charge-separated state and the electric field caused thereby attracts electrons (or more generally, charge carriers) from source electrode 32 and drain electrode 34, so that channel 36 becomes conducting. Thus, phototransistor 30 serves as an amplifier or a switching device where the light controls the current flowing from source electrode 32 and drain electrode 34.

The electrodes can be made of any conducting material, such as, but not limited to, gold. The inter-electrode spacing determines the channel length. The electrodes can be deposited on a semiconductor surface to form the source-channel-drain structure. The gate electrode can be formed from the isolated photocatalytic units of the present embodiments as further detailed hereinabove. A symbolic illustration of the phototransistor is illustrated at the right had side of FIG. 9.

As will be appreciated by one ordinarily skilled in the art, phototransistor 30 can operate while gate electrode 38 is left an open circuit because the gating is induced by photons impinging on electrode 38. Phototransistor 30 can be used as a logical element whereby the phototransistor can be switched to an "on" state by the incident light. In addition, phototransistor 30 can be used as the backbone of an image sensor with large patterning possible due to a strong variation of the drain current with the spatial position of the incident light beam. Several phototransistors, each operating at a different wavelength as further detailed hereinabove can be assembled to allow sensitivity of the image sensor to color images. The charge storage capability of the structure with further modifications known to one skilled in the art of conventional semiconductors can be exploited for memory related applications.

Photodiode 20 and/or phototransistor 30 can be integrated in many electronic circuitries. In particular, such devices can be used as building blocks which can be assembled on a surface structure to form a composite electronic assembly. For example, two or more photodiodes or phototransistors can be assembled on a surface structure to form a logic gate, a combination of logic gates or a microprocessor.

Reference is now made to FIG. 10 which is a simplified illustration of an optocoupler 40, according to various exemplary embodiments of the present invention. Optocoupler 40 is particularly useful for transferring signals from one element to another without establishing a direct electrical contact between the elements, e.g., due to voltage level mismatch. For example, optocoupler 40 can be used to establish contact free communication between a microprocessor operating at low voltage level and a gated switching device operating at high voltage level.

According to a preferred embodiment of the present invention optocoupler 40 comprises an optical transmitter 42 and an optical receiver 44. Transmitter 42 can be any light source, such as, but not limited to, a light emitting diode (LED). Receiver 44 preferably comprises optoelectronic device 10, and can be, for example, a photodiode (e.g., photodiode 20) or a phototransistor (e.g., phototransistor 30). Transmitter 42 is selected such that the radiation emitted thereby is at sufficient energy to induce charge separation between donor site 16 and acceptor site 18 of device 10.

Transmitter 42 and receiver 44 are kept at optical communication but electrically decoupled. For example, transmitter 42 and receiver 44 can be separated by a transparent barrier 46 which allows the passage of light but prevents any electrical current flow thereacross. Transmitter 42 and receiver 44 preferably oppose each other such that the radiation emitted from transmitter 42 strikes receiver 44.

Triggered by an electrical signal, transmitter 42 emits light 48 which passes through barrier 46 and strikes receiver 44. In turn, receiver 44 generates an electrical signal which can be tapped off via suitable electrical contacts as further detailed hereinabove. Thus optocoupler 40 successfully transmits to its output (receiver 44) an electrical signal applied at its input (transmitter 42), devoid of any electrical contact between the input and the output.

Reference is now made to FIGS. 11a-b, which are simplified illustrations of an optoelectronic device 50, according to various exemplary embodiments of the present invention.

In its simplest configuration, device 50 comprises one or more layers 52 of photoactive nanoparticles 54. Nanoparticles 54 are interposed between two electrodes 56 and 57. In the representative example shown in FIG. 11, electrode 57 is light transmissive. Electrode 56 can be light transmissive, light reflective or light absorptive.

As used herein, "a photoactive nanoparticle" refers to a particle which changes its electric dipole when irradiated by light. A photoactive nanoparticle can be, for example, a non-polarized nanoparticle which becomes electrically polarized when irradiated by light, or a nanoparticle characterized by a certain charge separation and which, in response to light, changes (typically increases) its charge separation.

In various exemplary embodiments of the invention nanoparticles 54 comprise photocatalytic units of a photosynthetic organism. For example, nanoparticles 54 can comprise surface 13 covalently attached to photocatalytic units 14, e.g., PS I, as further detailed hereinabove.

In use, electrode 57 is irradiated by light 11 which penetrates electrode 57 to impinge on layers 52. Each photoactive nanoparticle absorbs the energy of the light resulting in an electric dipole directed from electrode 56 to electrode 57 or vice versa. A potential difference is thus generated between electrodes 56 and 57. Electrical current caused by the potential difference can then be tapped off by electrical contacts as further detailed hereinabove. Thus, layers 56 and 57 serve as electron and hole injection contacts and device 50 generates a photocurrent in response to light.

In various exemplary embodiments of the invention the work functions of electrodes 56 and 57 differ. Preferably, the work function of electrode 56 is lower than the work function of electrode 57. The work function of a substance is defined as the minimal energy required for removing an electron from the substance into the vacuum. According to a preferred embodiment of the present invention, layer 56 is a low work function electrode.

As used herein, the term "low work-function" refers to a work-function of 4.5 eV or less, more preferably 4 eV or less.

Suitable low work function materials include, without limitation, alkaline metals, Group 2A, or alkaline earth metals, and Group III metals including rare earth metals and the actinide group metals. Also contemplated are the Group IB metals, metals in Groups IV, V and VI and the Group VIII transition metals. More specific examples of low work function materials, include, without limitation, lithium, magnesium, calcium, aluminum, indium, copper, silver, tin, lead, bismuth, tellurium and antimony.

According to a preferred embodiment of the present invention aluminum, layer 57 is a high work function electrode.

As used herein, the term "high work-function" refers to a work-function of 4.5 eV or more, more preferably 5 eV or more.

Suitable high work function materials include materials having any one of $InSnO_2$, $SnO_2$ and zinc oxide (ZnO) metal alloys. Other than these alloys, oxides of Sn and Zn may also be contained in the material of electrode 57.

FIG. 12 illustrates an energy-level diagram in the preferred embodiment in which electrode 56 is made of aluminum and electrode 57 is made of ITO. The internal electric field generated between the electrodes is sufficiently high to generate electric field that higher than the electron-cation pair excitonic energy.

According to a preferred embodiment of the present invention device 50 comprises a dielectric layer 64 deposited on electrode 56. Dielectric layer has a cavity 66 which exposes electrode 56. In this embodiment, layer(s) 52 are preferably placed in cavity 66 such that the photoactive nanoparticles contact electrode 56 at the base of the cavity and electrode 57 at the top of the cavity. Device 50 preferably comprises a substrate 62 which serves for carrying electrode 56 and layer 64. Two or more electrical contacts 58 are preferably attached to or formed on substrate 62. Contacts 58 are in electrical communication with electrodes 56 and 57 so as to tap off the electrical current of device 50.

In various exemplary embodiments of the invention the sizes of the above electronic devices (including, without limitation, the optoelectronic device, solar cell, photodiode, phototransistor, logic gate and optocoupler) are in the sub millimeter range. Preferably, the size of the electronic devices is from about 0.1 nm to about 100 μm, more preferably, from about 0.1 nm to about 1 μm.

Reference is now made to FIGS. 13*a-b*, which are schematic illustrations of an optoelectronic array 60, according to various exemplary embodiments of the present invention. Optoelectronic array 60 comprises several optoelectronic devices similar to device 50 arranged array-wise on a substrate 62, for example, a silicon substrate or the like. The advantage of using an optoelectronic array is that such configuration can facilitates up-scaling of the physical dimensions of the optoelectronic device to amplify the photovoltaic signal. It was found by the Inventors of the present invention that the dimension of such optoelectronic array can be from several microns to a few centimeters.

The electric configuration between the optoelectronic devices of array 60 depends on the desired output. For current output, the preferred electric configuration is serial, whereas for voltage output a parallel configuration is more preferred. The arrangement of the optoelectronic devices on substrate 62 is preferably such that several optoelectronic devices share the same electrodes. This can be achieved in any geometrical arrangement. For example, referring to FIG. 13*b*, two conductive layers and a dielectric layer separating one layer from the other can be deposited on substrate 62. One conductive layer can include electrodes of the type of, e.g., electrode 56, and another conductive layer can include electrodes of the type of, e.g., electrode 57. The electrodes of the conductive layers are preferably arranged in orthogonal or any other no-parallel directions. The photoactive particles of device 50 are introduced into cavities formed in the dielectric layer at the intersections between the electrodes of one layer and the electrodes of the other layer, such that each such intersection defines one optoelectronic device. A preferred process for fabricating array 60 is provided hereinunder with reference to FIG. 16*a-d*.

Reference is now made to FIGS. 14 and 15*a-d* which are a flowchart diagram (FIG. 14) and schematic process illustrations (FIGS. 15*a-d*) of a method suitable for fabricating an optoelectronic device, according to various exemplary embodiments of the present invention.

It is to be understood that, unless otherwise defined, the method steps described hereinbelow can be executed either contemporaneously or sequentially in many combinations or orders of execution. Additionally, one or more method steps described below are optional and may not be executed.

The method begins at step 70 and optionally and preferably continues to step 71 in which a first electrode is deposited on a substrate. FIG. 15*a* illustrate first electrode 56 deposited on a substrate 62. The first electrode, as stated, is preferably an electron-injection electrode which can be light transmissive, light reflective or light absorptive as desired. Step 71 can be executed by evaporation followed by photolithography and etching. For example, gold metal can be evaporated on a substrate silicon dioxide layer. The gold layer can then patterned by photolithography according to the desired shape of the first electrode. Subsequently, the electrode can be shaped by etching.

The method continues to step 72 in which photocatalytic units are covalently attached to the first electrode to provide a first layer of photoactive nanoparticles as further detailed hereinabove. The top side of the photoactive nanoparticles preferably comprises a conducting moiety to allow attachment of other photoactive nanoparticles.

The method then continues to step 73 in which one or more layers of the photoactive nanoparticles are attached to the first layer electrode (see FIG. 15*b*), to provide a plurality of layers of photoactive nanoparticles. Step 73 can be repeated one or more time, depending on the number of photoactive nanoparticle layers of the device.

Step 72 preferably comprises fabrication of a cavity 66, e.g., by forming a cavity through a dielectric layer 64 on top of first electrode 56 and substrate 62. The dielectric layer can be made of any dielectric material suitable for the process by which the cavity is formed. For example, a layer of silicon nitride can be deposited on top of the first electrode, e.g., using Chemical Vapor Deposition (CVD), physical vapor deposition (PVD), or atomic layer deposition (ALD). The cavity can then be formed in the dielectric layer (silicon nitride, in the present example) by photolithography followed by etching. In any event, cavity 66 is formed such that first electrode 56 is exposed on the base of the cavity, to allow adsorption of the photoactive nanoparticles on the first electrode.

The preferred adsorption technique depends on the type of photoactive nanoparticles. In various exemplary embodiments of the invention light induced adsorption is employed. When the nanoparticles comprise photocatalytic units having a modified polypeptide, the nanoparticles attach to the first electrode via the amino acids at the modified site. For example, thiolated PS I nanoparticles can be attached via their thiol moiety to form a stable oriented self assembled monolayer (SAM). Light induced adsorption can be used to adsorb the PS I nanoparticles into a dense layer.

Chemical bonding to the second electrode of the device can be improved by photoreducing $Pt^{4+}$ ions in solution by PS I monolayer. Such a procedure was earlier used for platinization of PS I in suspension [Millsaps, J. F.; Bruce, B. D.; Lee, J. W.; Greenbaum, E. Photochemistry and Photobiology 2001, 73, 630-635]. The procedure results in local deposition of Pt at the electron donor end of the protein. A fresh incubation of the platinized monolayer with cycteine mutants of PS I results in formation of sulfide bond between the cystiene in the PS I and the platized top of the monolayer to form a second oriented SAM. These cycles are preferably repeated so as to form of an oriented multilayer inside the cavity (see FIG. 15*c*).

Figure 15B:
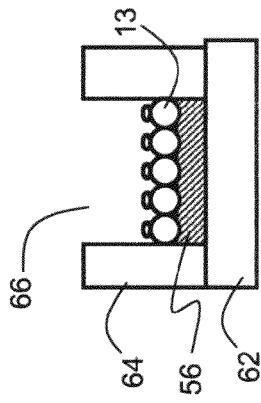
Figure 15D:
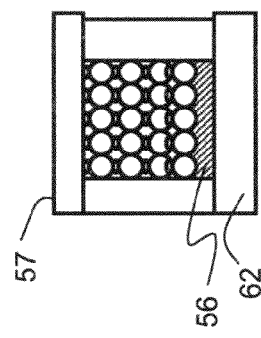
Figure 15A:
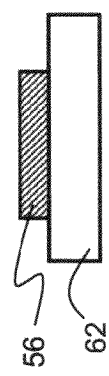
Figure 15C:
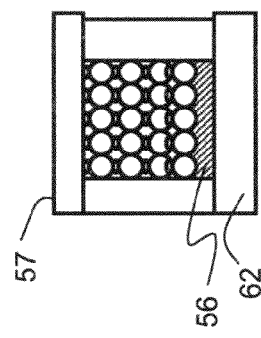

The method continues to step 74 in which the second electrode is deposited on the layer(s) of photoactive nanoparticles (see FIG. 15*d*). The second electrode, as stated, is preferably a hole-injection light transmissive electrode and it can be any electrode as long as it is capable of functioning as an anode so as to inject holes into the layers of nanoparticles. Preferably, the second electrode comprises ITO which can be deposited by sputtering, electron beam vapor deposition, ion plating, indirect evaporation process etc. In various exemplary embodiments of the invention ITO clusters are deposited on the nanoparticles with relatively very low momentum and temperature, so as to prevent or minimize the destruction of the nanoparticles.

The method ends at step 75.

Figures 16A, 16B, 16C, 16D:
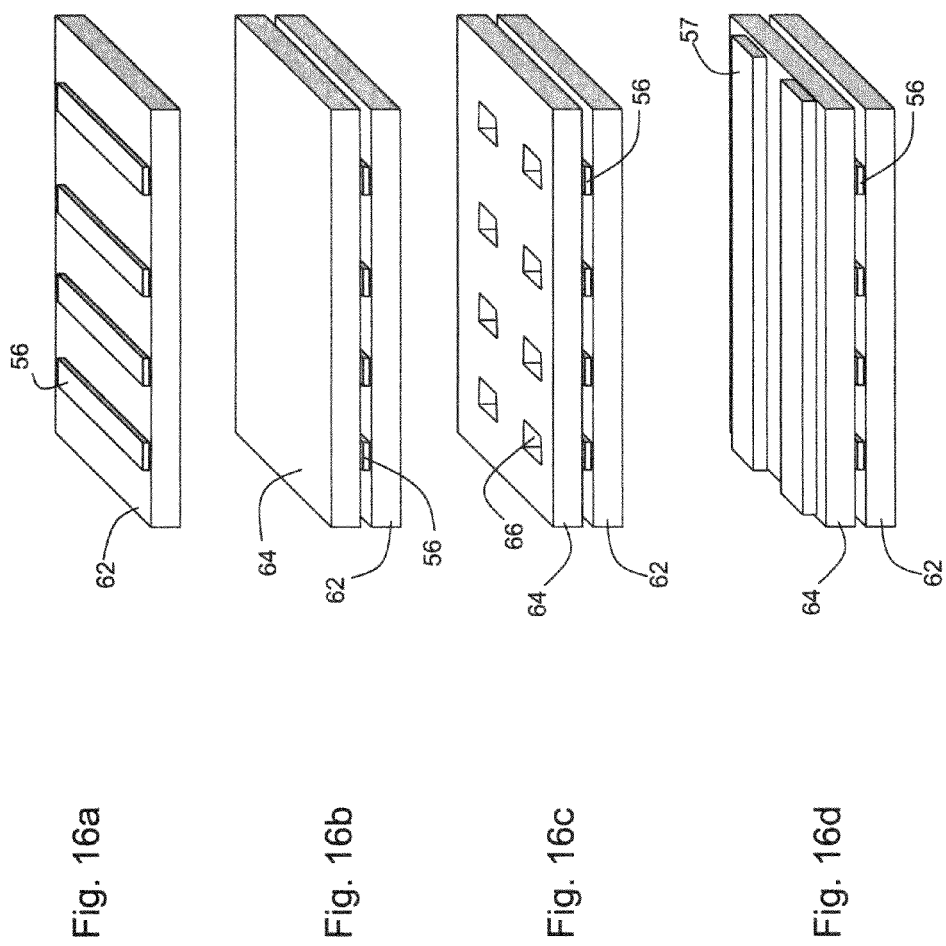

Reference is now made to FIGS. 16*a-d* which are schematic illustrations of a preferred process for an optoelectronic array, according to various exemplary embodiments of the present invention. With reference to FIG. 16*a*, a plurality of electrodes of the type of, e.g., electrode 56, is deposited on substrate 62. The technique for depositing the electrodes can be similar to the technique described above. For example, a conductive layer can be evaporated on the substrate and, photolithography followed by etching can be employed to form the electrodes on the evaporated layer. In the simplified illustration shown in FIG. 16a, electrodes 56 are conveniently shaped as a plurality of parallel stripes, but it is not intended to exclude any other shape for the electrodes.

With reference to FIGS. 16b-c, dielectric layer 64 is deposited on top of electrodes 56 and a plurality of cavities 66 are formed in dielectric layer 64 by photolithography followed by etching to expose electrode 56 as further detailed hereinabove.

Once the cavities are formed, the nanoparticles can be introduced into the cavities as further detailed hereinabove. A plurality of electrodes of the type of, e.g., electrode 57, is then deposited on layer 64 so as to contact the nanoparticle in cavities 66. Electrodes 57 are illustrated in FIG. 16d as a plurality of parallel stripes, substantially orthogonal to electrodes 56. Other shapes for electrodes 57 are also contemplated, provided the nanoparticles in the cavities interconnect electrodes 56 and 57.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Synthesis of *Synechocystis* sp. PCC 6803 psaB Mutants

The robust PS I reaction center from the cyanobacteria *Synechosystis* sp. PCC 6803 was selected to ascertain whether genetic modifications could assist in attachment of the reaction center to a solid support. The main reason for the structural stability of this PS I is due to the fact that all chlorophyll molecules and carotenoids are integrated into the core subunits complex while in plant and other bacterial reaction centers the antenna chlorophylls are bound to chlorophyll-protein complexes that are attached to the core subunits.

Selection of the amino acids to be modified to cysteines for covalent attachment of the PS I to the gold surface was based on the knowledge of the atomic structure of the PS I. Thus, amino acids in the extra membrane loops facing the cytoplasmic side of the bacterial membrane which do not have stereo hindrance when placed on a solid surface were mutated to cysteines in order to ensure formation of sulfide bonds. The various mutations were selected near the P700 to secure close proximity between the reaction center and the gold electrode in order to facilitate efficient electric junction.

Methods and Materials

Introduction of mutations in psaB of *Synechocystis* sp. PCC 6803 by homologous recombination: Site-directed mutagenesis in the psaB gene was effected by homologous recombination. A 1.8 kb psaB gene fragment and a 1.1 kb downstream flanking region were inserted into the pBluescript II KS vector (see scheme in FIGS. 1A-C). A 1.27 kb kanamycin resistance conferring gene (Kan$^R$) was excised from pUC4K and inserted at the EcoRI site at the beginning of the flanking to construct vector pZBL as previously described [Zeng et al., Biochim. Biophys. Acta 2002, 1556 254-264]. An overlapping extension PCR [Ho et al., Gene 1989, 77 51-59] was used for construction of an extended fragment 1400 bp, containing the mutations, and vectors pZBL D480C, pZL S500C, pZBL-S600C, pZBL Y635C, and pZBL D236C and pZBL-S247C, were constructed by fragment exchange at restriction sites Sph I-Hpa I and Sph I-Sac I, respectively.

The primers used to generate the polypeptides of the present invention are presented herein below in Table 4.

TABLE 4

| SEQ ID NO: | Sequences (5'→3') | Mutations | Plasmids |
|---|---|---|---|
| | psaB | | |
| SEQ ID NO: 1 | GTGTATGCGGCG<u>TGT</u>CCCGACACTGCTGGC | D235C | PZBL-D235C |

TABLE 4-continued

| SEQ ID NO: | Sequences (5'→3') | Mutations | Plasmids |
|---|---|---|---|
| SEQ ID NO: 2 | AGCAGTGTCGGGACACGCCGCATACACGCC | D235C | pZBL-D235C |
| SEQ ID NO: 3 | CACATTTTGGTTGTTCTGAAGGTGCTGGT | S246C | pZBL-S246C |
| SEQ ID NO: 4 | AGCACCTTCAGAACAACCAAAATGTGGCC | S246C | pZBL-S246C |
| SEQ ID NO: 5 | CTCTCCAATCCTTGCAGCATTGCTTCCACC | D479C | pZBL-D479C |
| SEQ ID NO: 6 | GGAAGCAATGCTGCAAGGATTGGAGAGCAA | D479C | pZBL-D479C |
| SEQ ID NO: 7 | GATGCTATCAACTGCGGCACCAACTCTCTG | S499C | pBL-S499C |
| SEQ ID NO: 8 | AGAGTTGGTGCCGCAGTTGATAGCATCCAA | S499C | pZBL-S499C |
| SEQ ID NO: 9 | CTCGGTGTTTGGTGCGGTAACGTTGCTCAG | S599G | pZBL-S599C |
| SEQ ID NO: 10 | AGCAACGTTACCGCACCAAACACCGAGGTG | S599C | pZBL-S599C |
| SEQ ID NO: 11 | GGTTACAACCCCTGCGGTGTCAACAATCTG | Y634C | pZBL-Y634C |
| SEQ ID NO: 12 | ATTGTTGACACCGCAGGGGTTGTAACCATT | Y634C | pZBL-Y634C |
| SEQ ID NO: 13 | GTGTATGCGGCGTGTCCCGACACTGCTGGC GGTTACAACCCCTGCGGTGTCAACAATCTG | D235C/ Y634C | pZBL-D235C/ Y634C |
| SEQ ID NO: 14 | AGCAGTGTCGGGACACGCCGCATACACGCC ATTGTTGACACCGCAGGGGTTGTAACCATT | D235C/ Y634C | pZBL-D235C/ Y634C |
| SEQ ID NO: 15 | CACATTTTGGTTGTTCTGAAGGTGCTGGT GGTTACAACCCCTGCGGTGTCAACAATCTG | S246C/ Y634C | pZBL-S246C/ Y634C |
| SEQ ID NO: 16 | AGCACCTTCAGAACAACCAAAATGTGGCC ATTGTTGACACCGCAGGGGTTGTAACCATT | S246C/ Y634C | pZBL-S246C/ Y634C |
| psa C | | | |
| SEQ ID NO: 17 | GAAATGGTGCCCTGGTGTGGTTGTAAAGCC | F31C | P61-2.4-F31C |
| SEQ ID NO: 18 | AGCGGCTTTACAACCACACCAGGGCACCAT | RW31C | P61-2.4-R3LC |
| SEQ ID NO: 19 His-taq C-term. | AGATCTTTAGTGGTGGTGGTGGTGGTGGTAA GCTAAACCCAT | His-taq C-term | P61-2.4-His-taq C-term |

Table 4 continued

In addition, a single mutation at W31C was also inserted in PsaC and two double mutations (D236C/Y635C and S247C/Y635C) were inserted in PsaB using the same techniques described above.

For selection of psaB deficient recipient cells, a pBLΔB vector was constructed by excision of 1.3 kb from the downstream end of psaB (from SphI to EcoRI from pZBL) and insertion of a 1.3 kb Chloramphenicol resistant confering gene (Cm$^R$) at these sites (FIG. 1C). Wild type *Synechocystis* cells were transformed with pPLΔB, and the transformants grown under "light adapted heterotrophic" conditions [Zeng et al., *Biochim. Biophys. Acta* 2002, 1556 254-264] to express the D480C mutant polypeptide (SEQ ID NO: 20), S500C mutant polypeptide (SEQ ID NO: 21), S600C mutant polypeptide (SEQ ID NO: 22), Y635C mutant polypeptide (SEQ ID NO: 23), D236C mutant polypeptide (SEQ ID NO: 24), S247C mutant polypeptide (SEQ ID NO: 25) and W31C mutant polypeptide (SEQ ID NO: 26).

Isolation of thylakoid membranes and PS I complexes: The *Synechocystis* cells were broken in a French pressure cell at 500 p.s.i. and thylakoids were isolated by differential centrifugation. PS I was solublilized by the detergent n-dodecyl β-D-maltoside and purified on DEAE-cellulose columns and on a sucrose gradient [Nechushtai, R., Muster, P., Binder, A., Liveanu, V., and Nelson, N. (1983) *Proc. Natl. Acad. Sci. USA* 80, 1179-1183]. The analysis of subunit composition by SDS polyacrylamide gel electrophoresis and Western blotting were performed as previously described [Laemmli, U. K. (1970) *Nature* 227, 680-685; Tindall, K. R. and Kunkel, T. A. (1988) *Biochemistry* 27, 6008-6013]. Protein in the membranes was determined after solubilization in 1% SDS as described [Lowry, O. H., Rosenbrough, N. L., Farr, A. L., and Randall, R. J. (1951) *J. Biol. Chem.* 193, 265-275]. Chlorophyll concentration and P700 chemical- and photo-oxidation were determined according to a published method [Arnon, D. I. (1949) *Plant Physiol.* 24, 1-15]. The detailed isolation procedure and analysis are summarized in [Gong et al., *Journal of Biological Chemistry* 2003, 278 19141-19150]. The analysis confirmed the isolation product is purified protein chlorophyll complex of PS I.

Surface-exposed cysteines on PS I were probed by biotin-maleimide which specifically reacts with the sulfhydryl groups. Biotin-labeled PS I complexes were dissociated and separated by sodium dodecyl sulfate polyacrylamide gel electrophoresis. For immunoblot detection, protein samples were transferred from the gel to nitrocellulose and reacted with peroxidase-conjugated avidin, then developed with enhanced chemiluminescence reagents as previously described [Sun et al., *Methods in Enzymology*, Academic Press, 1998, p. pp. 124-139].

Results

As illustrated in FIG. 1E, all modified purifed PS I units comprised surface-exposed cysteines. Although, the non-modified protein contains 9 free cysteines none of them were found to be exposed to the external surface when tested with the surface active reagent biotin-maleimide.

Example 2

Fabrication of Oriented Monolayers

Methods and Materials

Fabrication: The fabrication of orientated monolayers was carried out by directly reacting the cysteine in the mutant PS I with a fresh, clean, hydrophilic gold surface to form an Au-sulfide bond. A flat gold surface was prepared by evaporation of 5 nm of Cr and 150 nm of gold on a glass or silicon wafers. These surfaces were annealed at 350° C. for 1 h under vacuum. A buffered solution containing 1 mg chlorophyll of PS I in 1 ml was layered on top of the metal surface for incubation. Following a two hour incubation of either mutant or native PS I at room temperature, the unattached proteins were thoroughly washed with distilled water several times. The surface was dried with ultrapure nitrogen and observed using atomic force microscopy (AFM).

Atomic Force Microscopy (AFM): All measurements were made with a commercial AFM (Nanoscope® IIIa Multy-Mode™ with Extender™ Electronics Module, Veeco Instruments). The topography measurements were conducted in tapping mode at a cantilever resonance frequency of 300 kHz.

Results

PS I mutants self-assembled on the gold surfaces following annealing and remained covalently attached to the gold surface following the two hour incubation. Native PS I which were incubated in a similar manner were washed away from the gold surface. FIG. 2B illustrates atomic force microscopy images obtained by a scan of a 0.3 µm$^2$ area of the gold surface on the glass wafer, to which a monomer, of PS I cysteine mutant D480C was attached through sulfide bonds. FIG. 2B clearly shows a monolayer of particles 15-21 nm in diameter and 9 nm high. This is the expected size of PS I as obtained by crystallography. These particles are seen over the lightly granulated surface. FIG. 2A illustrates a scan of the annealed untreated naked gold surface, the annealed gold granules are 150 nm in diameter and 5 nm high.

Example 3

Photovoltage Properties of the PS I Mutant Fabricated Surfaces

The photovoltage of single PS I trimer and monomer complexes of cysteine mutant D480C in the monolayer was measured by Kelvin probe force microscopy (KPFM).

Materials and Methods

The KPFM setup is based on a commercial AFM (modified NanoScope® IIIa MultiMode, Veeco, USA) operating in tapping mode. The electrostatic force is measured in the so-called 'lift mode'. Essentially, after the topography is measured the tip is retracted from the sample surface to a fixed height. The oscillation of the tip induced by the piezo is stopped and an AC bias is applied to the cantilever at the same frequency used before for the topography measurements in the tapping mode. The CPD is extracted in the conventional way by nullifying the output signal of a lock-in amplifier which measures the electrostatic force at the first resonance frequency [Vatel et al., *Journal of Applied Physics* 1995, 772358-2362]. AFM topography and the corresponding KPFM electric potential were recorded in sequential scans at a scan rate of 1 Hz; 512 lines were scanned in two segments over the sample area to form two-dimensional image. A helium-neon laser ($\lambda$=632.8 nm, 5 mW/cm$^2$) was switched on for the first segment of the scan and off for the second.

Results

As illustrated in FIGS. 3A and 3B, the KPFM images demonstrate a clear light-induced electric potential in mutant PS I complexes. A light-induced positive potential of +0.498±0.02 V (see Table 1 hereinbelow) developed where peaks ascribed to PS I complexes were observed in the topographic trace (FIGS. 3A and 3B).

These results clearly indicate that all mutant PS I complexes bound to the gold surface were functionally active and oriented in the same direction. The induced potential is a result of a negative charge displacement away from the gold side of PS I as shown in FIG. 1D.

The measured change in contact potential difference (CPD) under illumination is in a good agreement with a simple calculation of the potential change ($\Delta\Phi$) resulting from an induced dipole layer of a height d, at an angle $\theta$ with respect to the surface normal given by: $\Delta\phi = Nqd \cos\theta/\epsilon$, where N is the area density of the dipole layer, q is the elementary charge, and $\epsilon$ is the layer dielectric constant. Using N of $2.2\times10^{11}$ cm$^{-2}$ for the trimmer, d=5 nm, $\epsilon$=2, and $\theta$=90° we obtain $\Delta\Phi$=0.41 Volt. The discrepancy between the expected +1 V and the calculated 0.41 V is partially resolved because the angle of the dipoles in the layer is not known, and also the dielectric constant is an ill-defined property since the dipole layer is not a bulk entity. Moreover, as the reaction centers were relatively far from each other the measured CPD under illumination was much less then the real CPD. Due to the long-range electrostatic forces, the measured CPD at a point on the surface below the tip apex is a weighted average of the surface potential in the vicinity of the tip. The effect of the tip electrostatic averaging has been calculated in the past using different algorithms [Y. Rosenwaks et al., *Physical Review B* 2004, 70 085320-085327]. Based on these calculations it is estimated that a more accurate quantity of the CPD (under illumination) is around a factor of two larger then the measured one. A similar light induced potential was measured in plant PS I placed on mercaptoethanol coated gold [R. Lee et al., *J. Phys. Chem. B* 2000, 104 2439-2443]. In these experiments, The PS I was insulated from the gold by the mercaptoethanol in a loosely bound monolayer and only 70% of the complexes assumed the same orientation. The gold surface work function also increased by approximately +0.125 V during illumination. Partial charge transfer to the vicinity of the photo-oxidized P700 which is located at the interface of PS I and the metal is expected to result in a more negative substrate. The charge transfer is indicative of efficient electronic coupling between the gold and PS I. There was however, very little change in the CPD when untreated gold surface was illuminated. It can also be seen that the PS I complexes had a slightly more positive potential (CPD of +0.2 V) than the gold substrate in the dark (FIG. 3B). This potential might have resulted from excitation of PS I by the AFM feedback laser that was not completely masked by the cantilever used in the KPFM setup. Such background excitation might cause an under estimation of the light minus dark CPD change in PS I.

The reversible nature of the light-induced electric potential was demonstrated by observing a change in the potential when the illumination was turned off. The results are provided in Table 5 herein below. The values represent an average potential of 24 individual PS I complexes measured either in the light or in the dark.

TABLE 5

| PS I/Potential | Dark (V) | Light (V) | Light to dark (V) | Dark to light (V) |
|---|---|---|---|---|
| monomer | −0.193 ± 0.0005 | +0.118 ± 0.0010 | +0.311 ± 0.0010 | — |
| monomer | −0.353 ± 0.0002 | +0.004 ± 0.0006 | — | +0.356 ± 0.001 |
| trimer | +0.870 ± 0.003 | +1.220 ± 0.0200 | +0.358 ± 0.0014 | — |
| trimer | +0.717 ± 0.003 | +1.215 ± 0.0200 | — | +0.498 ± 0.020 |

The measurements were started either in the light and then light was turned off (light to dark) or started in dark and then illumination was turned on (dark to light).

As detailed in Table 5, the illuminated trimers of PS I cysteine mutants in the monolayer developed a CPD of +1.220±0.02 V that decreased to +0.870±0.003 V when light was turned off (see FIG. 4B).

The substrate potential did not change when the light was turned off. Under the applied bias potential in the experiments charges could not move quickly to the balk gold substrate from the vicinity of PS I. Therefore, the light minus dark CPD (SPV) was smaller when the light was turned off compared to the difference on turning light on (Table 5). The average light minus dark potential difference of multiple PS I complexes was +0.358±0.014 V. There was no change in the contact potential where the gold surface was exposed. The photopotential could be reproduced multiple times repeatedly on the same sample or on a sample that was stored for over a month.

The PS I monomers of the cysteine mutant D480C readily formed self-assembled oriented monolayers. The average distance between the monomers (FIG. 2B) and the trimers (FIG. 5B) in the monolayers was 15 nm and 25 nm, respectively. The small monomers were more densely packed than the trimers in the monolayer yet, they could be resolved by the AFM measurements with the high resolution cantilever tip (FIG. 2B). However, neither the topography nor the CPD measurements were sensitive enough to resolve the individual monomers. Therefore, the CPD obtained by KPFM measurements in the dark of the PS I monomer monolayer describes a continuum (FIG. 5A). Similar images were observed when the topography was determined by the same setup (not shown). Yet, following light illumination, the CPD increased. An average of measurements of CPD at multiple locations on the monolayer in dark and in the light gave light-induced CPD of +0.356±0.001V (Table 5). A smaller light-induced CPD of +0.311±0.001 V was observed when the change was determined on turning off the illuminated monolayer.

Example 4

Self Assembly of other Cysteine Mutants of the Present Invention

Self assembly of oriented PS I was also obtained with three other mutants in which amino acids S500C, S600C, Y635C located at the exposed extra-membrane loops were modified to cysteines (see FIG. 1D). Both monomers and trimers of PS I of these mutants formed monolayers that generated light-induced CPD of similar magnitude to the one measured in monolayers fabricated by mutant D480C. Therefore, a functional oriented monolayer of PS I depends on formation of a sulfide bond between a cysteine located at the extra-membrane loop of the complex and is not confined to a specific location.

Example 5

Kinetic Analysis of Charge Recombination in PS I

To characterize the effects of the mutations on the electron transfer in the PS I complexes, flash-induced absorption changes were measured by single turnover spectroscopy.

Materials and Methods

Spectroscopic measurements: Measurements of P700 photooxidation at 700 nm and at 820 nm in thylakoids and PS I used a modified flash photolysis setup as earlier described described [Gong et al., *Journal of Biological Chemistry* 2003, 278 19141-19150]. The samples contained 25 mM Tris, pH 8, 10 mM sodium ascorbate, 10 µM phenazine methosulfate and 60 µg chlorophyll/ml PS I complexes. Absorption change transients were analyzed by fitting with a multiexponential decay using Marquardt least-squares algorithm programs (KaleidaGraph 3.5 from Synergy Software, Reading, Pa.).

Results

Light-induced oxidation of P700 causes a decrease in absorption at 700 nm or an increase in absorption at 820 nm. The flash-induced transient $\Delta A820$ (and at $\Delta A700$ nm, not shown) decay in PS I protein isolated from mutants D480C showed a similar result as in wild type, with a back reaction of 4.5 ms halftime, which may be ascribed to the reduction of $P700^+$ by the electron transfer mediator phenasine mehtosulfate (FIG. 6A). Similar results were obtained for S500C and S600C PS I complex. The results indicated that electrons are mediated to $F_A/F_B$ in the mutated PS I. If there was a disturbance in the mediation to $F_A/F_B$ and the reduction of $P700^+$ would be a result of reduction from a carrier that is located prior to $F_A/F_B$, the rate of recombination would be faster than 4.5 ms. Indeed, mutant S600C absorption decay was resolved into two components of 4.5 ms (85%) and 0.5 ms (15%) indicating that part of the electron transfer only reached $F_x$ resulting in charge recombination between $P700^+$ and $F_x^-$ [K. Brettel, Biochim. Biophys. Acta 1997, 1318 322-373]. The similarity of the rate of charge recombination between that of the wild type and the mutant indicates that site-directed mutagenesis does not alter the mode of action of light-induced electron transfer. These results are in agreement with the fact that the mutants could grow autotrophically in continuous light.

Example 6

Determination of Orientation by X-ray Fluorescence

Materials and Methods

X-ray absorption measurements: X-ray absorption and fluorescence was collected at undulator beam line Sector 18 ID-D, the BioCAT facility at the Advanced Photon Source, Argonne National Laboratories, Argonne, Ill. The beam was fed through double Si(III) crystal monochromator while harmonic rejection was attained by using a harmonic rejection mirror. Focused beam size was 100 µm by 150 µm with flux of $10^{14}$ photons/sec in $10^{-4}$ DE/E bandwidth. The incident X-ray beam intensity Io was monitored by $N_2$ gas filled ion chamber and X-ray fluorescence was monitored by the multilayer array detector. The Fe K-edge were scanned between X-ray energies of 7000 eV and 7900 eV. To minimize radiation damage 60 s scans were taken at each angle on the samples of PS I at 100K.

Results

PS I orientation in self assembled monolayer was determined by total reflection measurements of grazing x-ray fluorescence. PSI was attached through formation of sulfide bonds between unique cysteine and tungsten on tungsten-carbon multilayer over silicon substrates. Each graph is an average of 60, 42 s scans in the indicated angle to the x-ray beam normal 25, 45, 60 and 90 degrees. As illustrated in FIG. 6B, x-ray fluorescence k-edge changed as a function of the change in the angle relative to the polarized x-ray beam. Such a change was expected when PS I and the iron-sulfur cluster are oriented relative to the plane of the silicon substrate. Each of the three [4Fe-4S] iron-sulfur clusters form distorted cubes that are located at the center and along both sides of the pseudo-$C_2$ symmetry axis of PS I [P. Jordan, et al., *Nature* 2001, 411 909-917]. Therefore, the absorption extinction of a polarized x-ray beam is expected to change as a function of the angle of the PS I pseudo symmetry axis to the polarize beam. Indeed, the orientation of the iron-sulfur clusters was earlier determined in partially oriented thylakoid membranes by electron paramagnetic resonance [R. C. Prince, *Biochimica et Biophysica Acta* (BBA) *Bioenergetics* 1980, 592 323-337].

Conclusions

It was demonstrated for the first time in this work that selection of a robust reaction center PS I from cyanobacteria together with a rational design of mutations based on the crystallographic structure enable the fabrication of oriented monolayers on conducting metal surface. Direct binding of the protein complex to the metal electrode through formation of sulfide bond between unique cysteines induced by mutation secured the stability, orientation, function and an efficient electronic junction. The dry membrane protein in the monolayer retained it capacity to generate photo-potential of approximately +1 V. The photodiode properties, the nanometer scale dimension, the high quantum yield and the almost 60% energy conversion efficiency makes reaction centers intriguing nano-technological devices for applications in molecular electronics and biotechnology.

Example 7

PS I Based Photoactive Nanoparticles

In accordance with preferred embodiments of the present invention, photoactive PSI nanoparticles were incorporated in a solid state template. Robust PS I reaction centers from the cyanobacteria *Synechosystis* sp. PCC 6803 was found to be stable when covalently bound to metal. The main reason for the structural stability of this PS I is due to the fact that all chlorophyll molecules and carotenoids were integrated into the core subunits complex, while in plant and bacterial reaction centers the antenna chlorophylls are bound to chlorophyll-protein complexes that are attached to the core subunits. No peptide surfactants were required for stabilization.

The selection of the amino acids that were modified to cysteines for covalent attachment of the PS I to the gold surface consisted a second factor that insured structural and functional stability of the self-assembled oriented PS I. Amino acids in the extra membrane loops facing the cytoplasmic side of the bacterial membrane (D480C, S500C, Y635C) that do not have stereo hindrance when placed on a solid surface were mutated to cysteines in order to insure formation of sulfide bond.

The mutations did not modify the photochemical properties and the subunit composition of the isolated PS I. Oriented monolayers were fabricated by directly reacting the cysteine in the mutant PS I with a fresh, clean, hydrophilic gold surface to form an Au-sulfide bond.

The orientation and the photoactivity of the monolayers was measured by Kelvin probe force microscopy (KPFM) of single PS I trimer complexes of cysteine mutant in the monolayer.

FIGS. 17*a-b* are two-dimensional spatial (FIG. 17*a*) and electric potential (FIG. 17*b*) maps of the oriented monolayers. The images are of the same set of PS I reaction center trimers from mutant D480C on an Au—Si surface. FIG 17*c* shows binding PS I under illumination. The scanning directions for each raster of the constructed images were from top to bottom (from light to dark). The illumination was provided by a He—Ne laser at 632.8 nm, 5 mW/cm2. The images show a dense monolayer of particles 15-21 nm in diameter and 9 nm in height, which is the expected size of PS I as obtained by crystallography. Light induced potential enhanced the affinity to the metal resulting in aformation of a denser monolayer.

The KPFM image demonstrates a clear, light-induced electric potential in PS I. The light-induced positive potential of +1 V was developed where peaks ascribed to PS I complexes were observed. These results indicate that all PS I complexes bound to the gold surface were functionally active and oriented in the same direction. The induced potential is a result of a negative charge displacement away from the gold side of PS I. The reversible nature of the light-induced electric potential was demonstrated in an experiment in which a change in the potential was observed when the illumination was turned off. The average light minus dark potential difference of multiple PS I complexes was also approximately 1 V. The photopotential was reproduced a plurality of times and repeatedly on the same sample or on a sample that was stored for over a month.

Example 8

Vectorially Oriented Layers of Photoactive Nanoparticles

In accordance with preferred embodiments of the present invention, construct made of vectorially oriented layers of PS I, was prepared. The PS I layers were electronically connected in a serial fashion. The prepared construct has many advantages. It can increase the absorption cross section, increase electronic output and reduce the risk of shortcut between the top and bottom electrode. It was already demonstrated [Millsaps, supra] that metallic platinum can be precipitated at the site of electron emergence from the PS I reaction center.

The platinization process

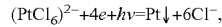

$$(PtCl_6)^{2-} + 4e + h\nu = Pt\downarrow + 6Cl^-,$$

occurs at pH 7 and room temperature. The source of electrons for reduction is the reducing electrons from the light-activated PSI reaction center itself.

Pt was precipitated on the reducing end of PS I assembled as an oriented monolayer on gold surface. AFM images of the monolayer show that the size of the PS I slightly increased as a result of platinization (FIGS. 18*a* and 18*c*). The phase contrast image however shows metal on top of each of the PS I (FIGS. 18*b* and 18*d*). XPS analysis of monolayers indicated 305 Pt atoms per PS I in the platinized monolayer compared to none in the monolayer of the untreated PS I. The calculation is based on the finding of a ratio 1/50 Pt/C assuming 16,800 carbon atoms per PS I.

Formation of vectorially oriented multilayers of PS I on a solid gold surface was performed by sequential binding and platinization of PS I. The initial monolayer was fabricated by formation of sulfide bonds between the metal surface and the unique cysteines in the mutant PS I. The washed monolayer was placed in $(PtCl_6)^{2-}$ solution and illuminated until the platization of the PS I. The platinized monolayer was washed and incubated again in a solution of cysteine mutants of PS I for binding by a formation of sulfide bond with the platinum patches on top of the PS I complexes. This process was repeated several times and the formation of new layer of PS I and its platinization was monitored by AFM and changes in the phase contrast. The thickness of the monolayers was determined by ellipsometry, the Pt content by XIPS and the function by determination of the photo-potential with KPFM microscopy. The platinization enabled vectorially oriented monolayers and good electronic coupling between in the serially assembled photosystems.

Electrochemical measurements of photocurrent generated by the PS I monolayer were done in a three electrode configuration. A working electrode, Pt counter electrode, and a Ag/AgCl, 1 M KCl reference. The working electrode was illuminated with a 150 W incandescent slid projector. The potential at the working electrode was set at between –0.4 and 0.04 V versus Ag/AgCl electrode.

The medium contained 0.1 M tris-HCl, pH 7.5 and 0.05 mM metyl viologene for mediation of electrons between PS I and the electrode. High photocurrent of 0.065 mA/Cm$^2$ was measured with the PS I monolayer on gold electrode (FIG. 19). Similar results were obtained with the platized PS I monolayer.

Due to the direct binding of PS I in accordance with the teachings of the present embodiments, the obtained photocurrent is 2,160 fold larger than a photocurrent of 30 nA/Cm$^2$ obtained with oriented monolayer of bacterial reaction center [Trammell, supra].

Example 9

A Vertical Prototype Device

A vertical prototype device was fabricated according to the teaching of the present embodiments. The physical dimensions of the prototype device were up scaled to amplify the photovoltaic signal. For photovoltaic measurements a multi cell array architecture was adopted. This multifunction architecture allowed to explore and measure the photoelectric properties of single cells (the intersection between vertical and horizontal lines), and measure of the output photo-voltage and current signals of multiple cells and arrays arranged in series or parallel configurations. This flexibility is achieved by changing the electrical connections between the pads that are connecting the cells via a probe station setup.

The fabrication process began by evaporation of 100-200 nm of gold metal on top of a silicon dioxide layer (silicon wafer). The gold metal served as the bottom electrode of the device. The shape of the electrode was defined by photolithography and produced by wet I/I$^-$ etching (FIGS. 20$a$-$c$). Subsequently, a dielectric platform layer was formed by depositing 50 nm of Si$_3$N$_4$ were on top of the gold electrode using CVD. A square cavity, reaching the gold electrode, was formed in the Si$_3$N$_4$ platform by electron beam lithography followed by etching.

The PSI SAM were then introduced into the formed cavities and ITO electrodes were deposited by sputtering technique to encapsulate the PSI within the cavities. The thus fabricated prototype is illustrated in FIG. 21. The sputtering was by a special technique developed by Prof. David Cahen (Weizmann Institute, Israel). In accordance with this technique, ITO clusters were deposited on the SAM with relatively very low momentum and temperature. Such conditions prevented the destruction of the SAM. The top electrode was then defined by photolithography and wet etching.

FIG. 22 illustrates the set-up used for the photoconductivity experiments of the prototype device. The measurements of the device were performed using Desert-cryogenics probestation attached to a Keithley low current source measure unit. A white light source of output powers 50 and 100 Watts (giving 1 kW/m$^2$ at the sample which is similar to solar irradiance) was used to initiate the photoconductivity process FIG. 23 shows measurements of the current as a function of the voltage (I/V). As shown the I/V measurements in dark revealed a two back-to back diode properties. The lack of photovoltage signal can be explained by the low internal electric field between the contacts (the work function difference between ITO and Au is relatively small), and due to the effects of the interface between the sputtered ITO and the PSI layer. I/V measurements under illumination gave a clear photoconductivity effect with an average output current of 0.3A/Cm$^2$. These results demonstrate photoactivity, low Schottky barrier and good electronic coupling through the junctions of the two electrodes.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An isolated polypeptide comprising an amino acid sequence as set forth in SEQ ID NO: 20.

2. An isolated photocatalytic unit comprising the isolated polypeptide of claim 1.

3. A membrane preparation comprising the photocatalytic unit of claim 2.

4. The isolated photocatalytic unit of claim 2, being in a monomeric or trimeric form.

* * * * *